US010369167B2

(12) United States Patent
Pang et al.

(10) Patent No.: US 10,369,167 B2
(45) Date of Patent: Aug. 6, 2019

(54) CONTINUOUSLY EXPRESSED THERAPEUTIC RNAS FOR TARGETED PROTEIN BINDING AND METHODS FOR THEIR USE

(71) Applicant: CITY OF HOPE, Duarte, CA (US)

(72) Inventors: Ka Ming Pang, Arcadia, CA (US); John J. Rossi, Azusa, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/800,836

(22) Filed: Nov. 1, 2017

(65) Prior Publication Data
US 2018/0125878 A1   May 10, 2018

Related U.S. Application Data

(60) Provisional application No. 62/415,919, filed on Nov. 1, 2016.

(51) Int. Cl.
| | |
|---|---|
| *C07H 21/04* | (2006.01) |
| *A61K 31/7105* | (2006.01) |
| *A61K 9/00* | (2006.01) |
| *A61P 31/18* | (2006.01) |
| *C12N 15/115* | (2010.01) |
| *C12N 15/113* | (2010.01) |

(52) U.S. Cl.
CPC ........ *A61K 31/7105* (2013.01); *A61K 9/0019* (2013.01); *A61P 31/18* (2018.01); *C12N 15/115* (2013.01); *C12N 15/1132* (2013.01); *C12N 2310/14* (2013.01); *C12N 2310/141* (2013.01); *C12N 2310/16* (2013.01); *C12N 2310/3519* (2013.01); *C12N 2310/531* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,977,089 A | 11/1999 | Arimilli et al. | |
| 6,005,087 A | 12/1999 | Cook et al. | |
| 6,031,086 A | 2/2000 | Switzer | |
| 6,127,533 A | 10/2000 | Cook et al. | |
| 6,225,460 B1 | 5/2001 | Bischofberger et al. | |
| 6,399,754 B1 | 6/2002 | Cook | |
| 6,403,779 B1 | 6/2002 | Kawasaki et al. | |
| 2004/0067503 A1 | 4/2004 | Tan et al. | |
| 2006/0105975 A1* | 5/2006 | Pendergrast | C12N 15/111 514/44 A |

OTHER PUBLICATIONS

Lu et al. Journal of Virology, Dec. 2004, p. 12868-12876.*
Held, Daniel M., et al. "HIV-1 inactivation by nucleic acid aptamers." Front Biosci 11 (2006): 89-112.*
Boden et al. NAS 2004 1154-1158.*
Aagaard, L., et al., "Engineering and Optimization of the Mir-106b-Cluster for Ectopic Expression of Multiplexed Anti-HIV RNAs," Gene Ther. 15(23):1536-1549 (2008).
Adachi, A., et al., "Production of Acquired Immunodeficiency Syndrome-Associated Retrovirus in Human and Nonhuman Cells Transfected with an Infectious Molecular Clone," J. Virol. 59(2):284-291 (1986).
Anderson, J. S., et al., "Preintegration HIV-1 Inhibition by a Combination Lentiviral Vector Containing a Chimeric TRIM5α Protein, a CCR5 shRNA, and a TAR Decoy," Mol. Ther. 17(12):2103-2114 (2009).
Arhel, N., et al., "Host Proteins Involved in HIV Infection: New Therapeutic Targets," Biochimica et Biophysica Acta 1802:313-321 (2010).
Asparuhova, M. B., et al., "Development and Characterization of a Triple Combination Gene Therapy Vector Inhibiting HIV-1 Multiplication," J. Gene Med. 10:1059-1070 (2008).
Bertrand, E., et al., "The Expression Cassette Determines the Functional Activity of Ribozymes in Mammalian Cells by Controlling Their Intracellular Localization," RNA 3:75-88 (1997).
Castanotto, D., et al., "CRM1 Mediates Nuclear-Cytoplasmic Shuttling of Mature MicroRNAs," PNAS 106(51):21655-21659 (2009).
Cherepanov, P., et al., "High-Level Expression of Active HIV-1 Integrase from a Synthetic Gene in Human Cells," FASEB J. 14:1389-1399 (2000).
Cherepanov, P., et al., "HIV-1 Integrase Forms Stable Tetramers and Associates with LEDGF/p75 Protein in Human Cells," J. Biol. Chem. 278(1):372-381 (2003).
Choi, Y. S., et al., "The RNA Aptamer Disrupts Protein—Protein Interaction Between β-Catenin and Nuclear Factor-κB p50 and Regulates the Expression of C-Reactive Protein," FEBS Letters 583:1415-1421(2009).
Chung, J., et al., "Optimized Lentiviral Vectors for HIV Gene Therapy: Multiplexed Expression of Small RNAs and Inclusion of MGMT$^{P140K}$ Drug Resistance Gene," Mol. Ther. 22(5):952-963 (2014).
Digiusto, D. L., et al., "RNA-Based Gene Therapy for HIV with Lentiviral Vector-Modified CD34(+) Cells in Patients Undergoing Transplantation for AIDS-Related Lymphoma," Sci. Transl. Med. 2(36):36ra43 (2010).

(Continued)

*Primary Examiner* — Kimberly Chong
(74) *Attorney, Agent, or Firm* — Perkins Coie LLP; Lara J. Dueppen

(57) ABSTRACT

An RNA composition comprising an RNA aptamer and an shRNA molecule and/or an miRNA molecule are provided. The RNA composition may include an aptamer component that binds an enzymatic protein within a target cell and an shRNA and/or an miRNA component that facilitates trafficking of the aptamer within the target cell, such as, trafficking from the nucleus into the cytoplasm. The RNA aptamer and the shRNA and/or the miRNA component of the composition can be a fusion or independent molecules.

13 Claims, 26 Drawing Sheets
Specification includes a Sequence Listing.

(56) References Cited

OTHER PUBLICATIONS

Digiusto, D. L., " Stem Cell Gene Therapy for HIV: Strategies to Inhibit Viral Entry and Replication," Curr. HIV/AIDS Rep. 12:79-87 (2015).
Ditzler, M. A., et al., "Broad-Spectrum Aptamer Inhibitors of HIV Reverse Transcriptase Closely Mimic Natural Substrates," Nucl. Acids Res. 39(18):8237-8247 (2011).
Duclair, S., et al., "High-Affinity RNA Aptamers Against the HIV-1 Protease Inhibit Both In Vitro Protease Activity and Late Events of Viral Replication," Mol. Ther. Nucl. Acids 4:e228 (2015).
Ellington, A. D., et al., "Selection In Vitro of Single-Stranded DNA Molecules that Fold into Specific Ligand-Binding Structures," Nature 355:850-852 (1992).
Feng, Y., et al., "A Comprehensive Analysis of Precursor MicroRNA Cleavage by Human Dicer," RNA 18:2083-2092 (2012).
Gartner, S., et al., "The Role of Mononuclear Phagocytes in HTLV-III/LAV Infection," Science 233:215-219 (1986).
Good, P.D., et al., "Expression of Small, Therapeutic RNAs in Human Cell Nuclei," Gene Ther. 4:45-54 (1997).
Jenkins, T. M., et al., "A Soluble Active Mutant of HIV-1 Integrase: Involvement of Both the Core and Carboxyl-Terminal Domains in Multimerization," J. Biol. Chem. 271(13):7712-7718 (1996).
Kruspe, S., et al., "Aptamers as Drug Delivery Vehicles," Chem. Med. Chem. 9:1998-2011 (2014).
Lange, M. J., et al., "Robust Suppression of HIV Replication by Intracellularly Expressed Reverse Transcriptase Aptamers is Independent of Ribozyme Processing," Mol. Ther. 20(12):2304-2314 (2012).
Lee, N. S., et al., "Functional and Intracellular Localization Properties of U6 Promoter-Expressed siRNAs, shRNAs, and Chimeric VA1 shRNAs in Mammalian Cells," RNA 14:1823-1833 (2008).
Lee, S. J., et al., "Selective Nuclear Export Mechanism of Small RNAs," Curr. Opin. Struct. Biol. 21:101-108 (2011).
Leibman, R. S., et al., "Engineering T Cells to Functionally Cure HIV-1 Infection," Mol. Ther. 23(7):1149-1159 (2015).
Li, M.J., et al., "Lentiviral Vector Delivery of Recombinant Small Interfering RNA Expression Cassettes," Methods Enzymol. 392:218-226 (2005).
Li, M.J., et al., "Long-Term Inhibition of HIV-1 Infection in Primary Hematopoietic Cells by Lentiviral Vector Delivery of a Triple Combination of Anti-HIV shRNA, Anti-CCR5 Ribozyme, and a Nucleolar-Localizing TAR Decoy," Mol. Ther. 12(5):900-909 (2005).
Llano, M., et al., "Identification and Characterization of the Chromatin-Binding Domains of the HIV-1 Integrase Interactor LEDGF/p75," J. Mol. Biol. 360:760-773 (2006).
Mi, J., et al., "H1 RNA Polymerase III Promoter-Driven Expression of an RNA Aptamer Leads to High-Level Inhibition of Intracellular Protein Activity," Nucl. Acids Res. 34(12):3577-3584 (2006).
Morner, A., et al., "Primary Human Immunodeficiency Virus Type 2 (HIV-2) Isolates, Like HIV-1 Isolates, Frequently Use CCR5 but Show Promiscuity in Coreceptor Usage," J. Virol. 73(3):2343-2349 (1999).

Okada, C., et al., "A High-Resolution Structure of the Pre-microRNA Nuclear Export Machinery," Science 326:1275-1279 (2009).
Paul, C. P., et al., "Localized Expression of Small RNA Inhibitors in Human Cells," Mol. Ther. 7(2):237-247 (2003).
Pernet, O., et al., "Stem Cell-Based Therapies for HIV/AIDS," Adv. Drug. Deliv. Rev. 103:187-201 (2016).
Ramalingam, D., et al., "RNA Aptamers Directed to Human Immunodeficiency Virus Type 1 Gag Polyprotein Bind to the Matrix and Nucleocapsid Domains and Inhibit Virus Production," J. Virol. 85(1):305-314 (2011).
Salamanca, H. H., et al., "Inhibiting Heat Shock Factor 1 in Human Cancer Cells with a Potent RNA Aptamer," PLoS One 9(5):e96330 (2014).
Shum, K.T., et al., "Aptamer-Based Therapeutics: New Approaches to Combat Human Viral Diseases," Pharmaceuticals 6:1507-1542 (2013).
Summa, V., et al., "Discovery of Raltegravir, a Potent, Selective Orally Bioavailable HIV-Integrase Inhibitor for the Treatment of HIV-AIDS Infection," J. Med. Chem. 51:5843-5855 (2008).
Temesgen, Z., et al., "Raltegravir: First in Class HIV Integrase Inhibitor," Therapeutics and Clinical Risk Management 4(2):493-500 (2008).
Tuerk, C., et al., "Systematic Evolution of Ligands by Exponential Enrichment: RNA Ligands to Bacteriophage T4 DNA Polymerase," Science 249:505-510 (1990).
Whatley, A. S., et al., "Potent Inhibition of HIV-1 Reverse Transcriptase and Replication by Nonpseudoknot, "UCAA-Motif" RNA Aptamers," Mol. Ther. Nucl. Acids 2:e71 (2013).
Winter, J., "Loop-miRs: Active MicroRNAs Generated From Single-Stranded Loop Regions," Nucl. Acids Res. 41(10):5503-5512 (2013).
Yam, P. Y., et al., "Design of HIV Vectors for Efficient Gene Delivery into Human Hematopoietic Cells," Mol. Ther. 5(4):479-484 (2002).
Zheng, Y., et al., "Host Protein Ku70 Binds and Protects HIV-1 Integrase from Proteasomal Degradation and is Required for HIV Replication," J. Biol. Chem. 286(20):17722-17735 (2011).
Zheng, Y., et al., "Posttranslational Modifications of HIV-1 Integrase by Various Cellular Proteins During Viral Replication," Viruses 5:1787-1801 (2013).
Zhou, J., et al., "Selection, Characterization and Application of New RNA HIV gp 120 Aptamers for Facile Delivery of Dicer Substrate siRNAs into HIV Infected Cells," Nucl. Acids Res. 37(9):3094-3109 (2009).
Zhou, J., et al., "Cell-Specific RNA Aptamer Against Human CCR5 Specifically Targets HIV-1 Susceptible and Inhibits HIV-1 Infectivity," Chem. Biol. 22(3):379-390 (2015).
Zhou, J., et al., "Aptamers as Targeted Therapeutics: Current Potential and Challenges," Nat. Rev. Drug Discov. 16:181-202 (2017).
Zuker, M., "Mfold Web Server for Nucleic Acid Folding and Hybridization Prediction," Nucl. Acids Res. 31(13):3406-3415 (2003).

* cited by examiner

```
S1R4    GAAG--GTTAAGA----GTTGATGTTCACACTTCGT--  30
S4R3    TATGTCGTCGAGG----GTTGG-GT--GCGCTGTGTT-  30
S1R5    --AGGAGCCAAGCC--CGTAAACAAACGGCGTTA----  30
S4R2    ------ACCTGGCC--CCGAAAAATTTCGGGTTGAGCT  30
S1R1    CGTATGGGTGAGCC--CGTTAAGAT-TGCGCGT-----  30
S3R2    CGTATGGGTGAGCC--CGTTAAGAT-TGCGCGT-----  30
S4R1    CGTATGGGTGAGCC--CGTTAAGAT-TGCGCGT-----  30
S4R4    CGGATGGGTGAGCC--CGTTAAGAT-TGCGCGT-----  30
S3R5    CGGATGGGTGAGCC--CGTTAAGAT-TGCGCGT-----  30
S1R2    CGTA-GGGTGAGCC--CGTTAGTATATGCGCT------  29
S1R3    CATA-GG-TAAGCC--CGTTTATAGGTGCGCTTG----  30
S3R6    --GCCAATGGGGAC--CGTCC-TATTTGGGATGTC---  30
S3R1    --CCTAGACGCGCTGCCGTGGA-GGAGGAGGTT-----  30
S3R4    --TATCGCAGCTTTTGCGCCGATGGAGGAGGT------  30
S3R3    --CGTCG-TATGCTG-CGCC-ATGGGGTGGACTG----  29
```

*FIG. 2B*

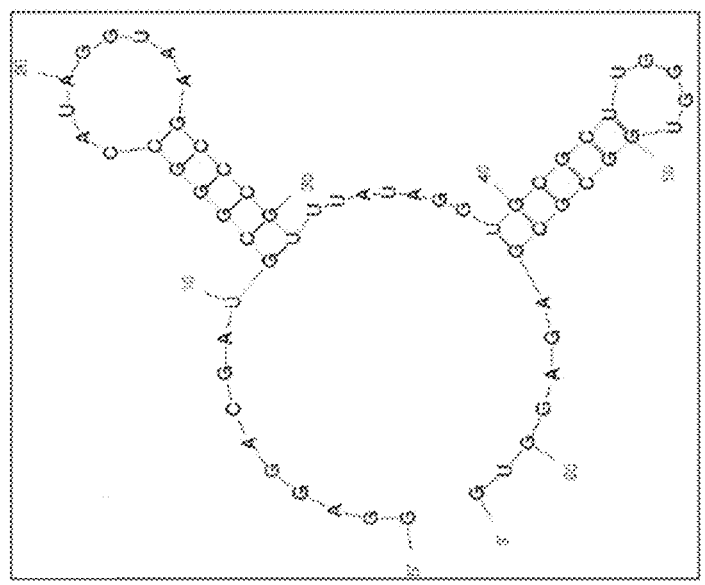
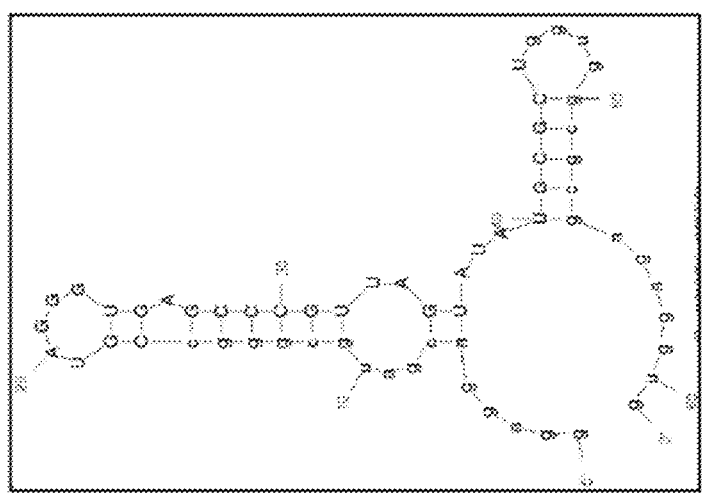
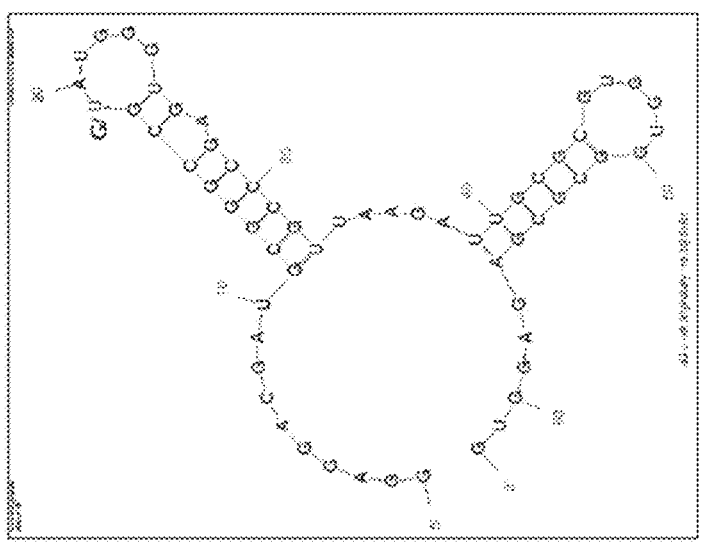
FIG. 3A  S1R1, S3R2, S4R1, S3R5, S4R4
FIG. 3B  S1R2
FIG. 3C  S1R3

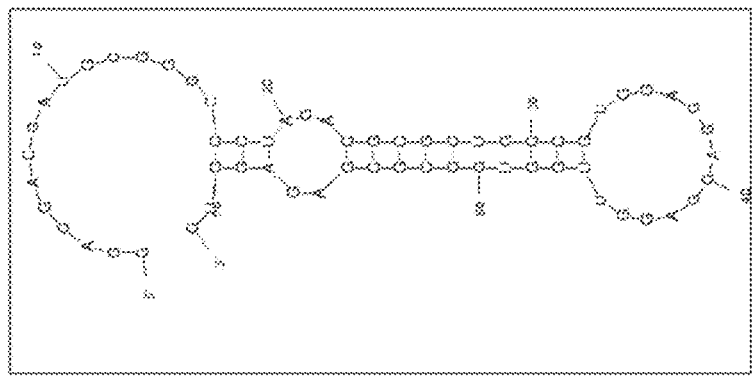
FIG. 3F S3R1
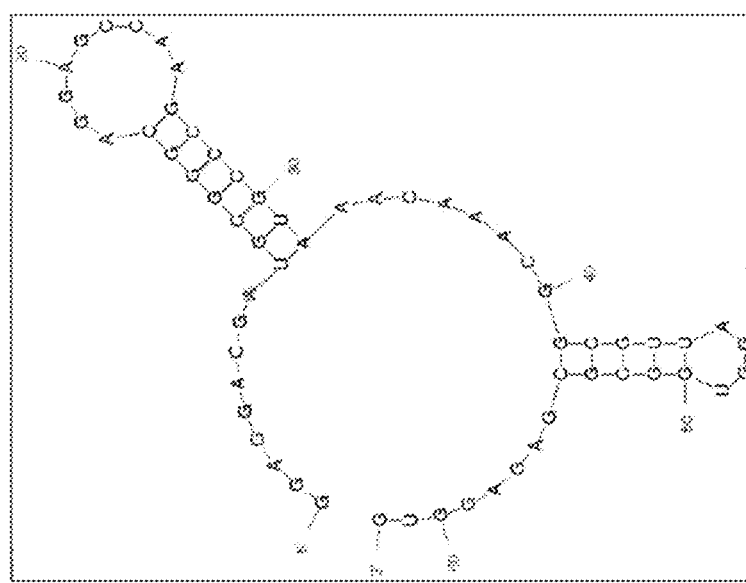
FIG. 3E S1R5
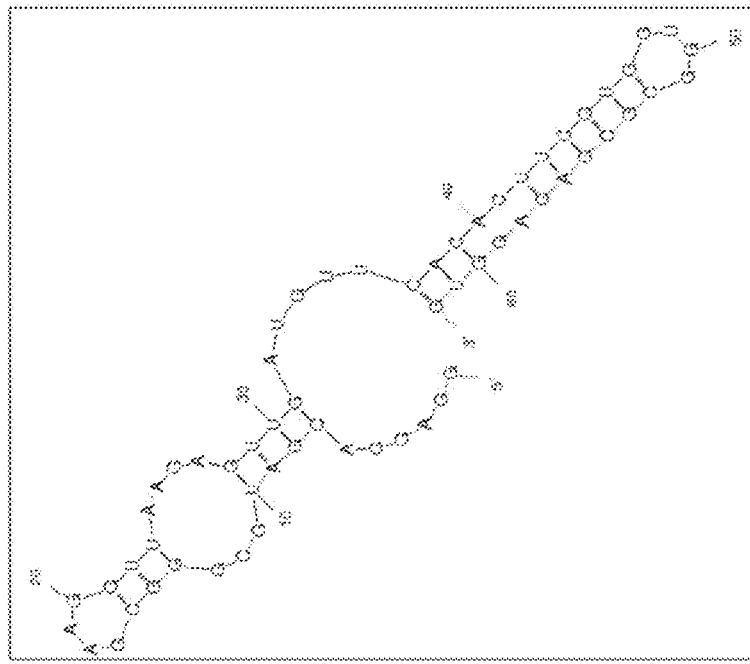
FIG. 3D S1R4

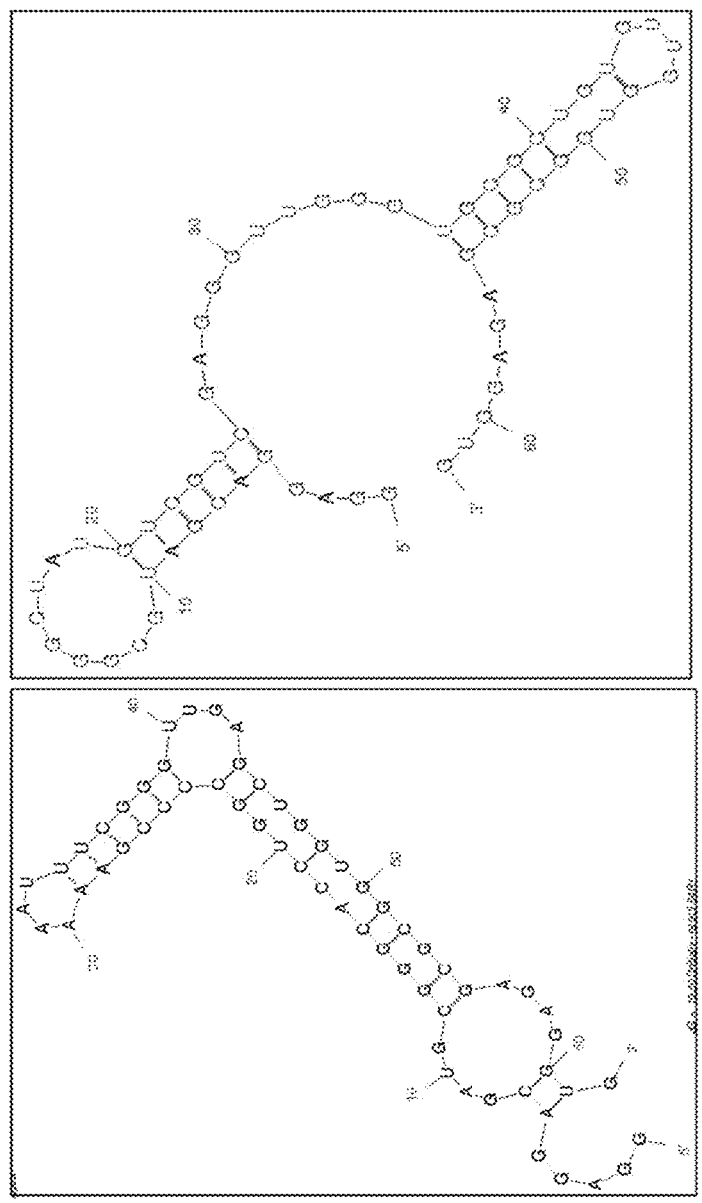
FIG. 3J  S4R2
FIG. 3K  S4R3

SEQUENCE LISTING

<160> NUMBER OF SEQ ID NOS: 40

<210> SEQ ID NO 1
<211> LENGTH: 30
<212> TYPE: DNA
<213> ORGANISM: Artificial Sequence
<220> FEATURE:
<223> OTHER INFORMATION: aptamer

<400> SEQUENCE: 1
cgtatgggtg agcccgttaa gattgcgcgt        30

<210> SEQ ID NO 2
<211> LENGTH: 30
<212> TYPE: DNA
<213> ORGANISM: Artificial Sequence
<220> FEATURE:
<223> OTHER INFORMATION: aptamer

<400> SEQUENCE: 2
acctggcccc gaaaaatttc gggttgagct        30

<210> SEQ ID NO 3
<211> LENGTH: 29
<212> TYPE: DNA
<213> ORGANISM: Artificial Sequence
<220> FEATURE:
<223> OTHER INFORMATION: aptamer

<400> SEQUENCE: 3
ccaatgggga ccgtcctatt tgggatgtc        29

<210> SEQ ID NO 4
<211> LENGTH: 30
<212> TYPE: DNA
<213> ORGANISM: Artificial Sequence
<220> FEATURE:
<223> OTHER INFORMATION: aptamer

<400> SEQUENCE: 4
tatcgcagct tttgcgccga tggaggaggt        30

<210> SEQ ID NO 5
<211> LENGTH: 29
<212> TYPE: DNA
<213> ORGANISM: Artificial Sequence
<220> FEATURE:
<223> OTHER INFORMATION: aptamer

<400> SEQUENCE: 5
cgtcgtatgc tgcgccatgg ggtggactg        29

<210> SEQ ID NO 6
<211> LENGTH: 80
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (35)..(64)
<223> OTHER INFORMATION: n is a, c, g, or t

```
<400> SEQUENCE: 6
taatacgact cactataggg aggacgatgc gggcnnnnnn nnnnnnnnnn nnnnnnnnnn    60
nnnnggtggc gcgagaggtg                                              80

<210> SEQ ID NO 7
<211> LENGTH: 32
<212> TYPE: DNA
<213> ORGANISM: Artificial Sequence
<220> FEATURE:
<223> OTHER INFORMATION: forward primer

<400> SEQUENCE: 7
taatacgact cactataggg aggacgatgc gg                                32

<210> SEQ ID NO 8
<211> LENGTH: 16
<212> TYPE: DNA
<213> ORGANISM: Artificial Sequence
<220> FEATURE:
<223> OTHER INFORMATION: reverse primer

<400> SEQUENCE: 8
cacctctcgc gccacc                                                  16

<210> SEQ ID NO 9
<211> LENGTH: 57
<212> TYPE: DNA
<213> ORGANISM: Artificial Sequence
<220> FEATURE:
<223> OTHER INFORMATION: JRO450 oligonucleotide

<400> SEQUENCE: 9
caccgcttac gctgagtact tcgaaattga agcttgtttc gaagtactca gcgtaag     57

<210> SEQ ID NO 10
<211> LENGTH: 57
<212> TYPE: DNA
<213> ORGANISM: Artificial Sequence
<220> FEATURE:
<223> OTHER INFORMATION: JRO451 oligonucleotide

<400> SEQUENCE: 10
aaaacttacg ctgagtactt cgaaacaagc ttcaatttcg aagtactcag cgtaagc     57

<210> SEQ ID NO 11
<211> LENGTH: 58
<212> TYPE: DNA
<213> ORGANISM: Artificial Sequence
<220> FEATURE:
<223> OTHER INFORMATION: JRO535 oligonucleotide

<400> SEQUENCE: 11
caccgcggag acagcgacga agagcattga agcttgtgct cttcgtcgct gtctccgc    58

<210> SEQ ID NO 12
<211> LENGTH: 58
<212> TYPE: DNA
<213> ORGANISM: Artificial Sequence
<220> FEATURE:
<223> OTHER INFORMATION: JRO536 oligonucleotide

<400> SEQUENCE: 12
aaaagcggag acagcgacga agagcacaag cttcaatgct cttcgtcgct gtctccgc    58
```

<210> SEQ ID NO 13
<211> LENGTH: 54
<212> TYPE: DNA
<213> ORGANISM: Artificial Sequence
<220> FEATURE:
<223> OTHER INFORMATION: JRO500 oligonucleotide

<400> SEQUENCE: 13
caccgatgcg ggccgtatgg gtgagcccgt taagattgcg cgtggtggcg cgag          54

<210> SEQ ID NO 14
<211> LENGTH: 54
<212> TYPE: DNA
<213> ORGANISM: Artificial Sequence
<220> FEATURE:
<223> OTHER INFORMATION: JRO501 oligonucleotide

<400> SEQUENCE: 14
aaaactcgcg ccaccacgcg caatcttaac gggctcaccc atacggcccg catc          54

<210> SEQ ID NO 15
<211> LENGTH: 56
<212> TYPE: DNA
<213> ORGANISM: Artificial Sequence
<220> FEATURE:
<223> OTHER INFORMATION: JRO502 oligonucleotide

<400> SEQUENCE: 15
caccgcgggc cctagacgcg ctgccgtgga ggaggaggtt ggtggcgcga gaggtg        56

<210> SEQ ID NO 16
<211> LENGTH: 56
<212> TYPE: DNA
<213> ORGANISM: Artificial Sequence
<220> FEATURE:
<223> OTHER INFORMATION: JRO503 oligonucleotide

<400> SEQUENCE: 16
aaaacacctc tcgcgccacc aacctcctcc tccacggcag cgcgtctagg gcccgc        56

<210> SEQ ID NO 17
<211> LENGTH: 60
<212> TYPE: DNA
<213> ORGANISM: Artificial Sequence
<220> FEATURE:
<223> OTHER INFORMATION: JRO504 oligonucleotide

<400> SEQUENCE: 17
caccgggagg acgatgcggg ccgtcgtatg ctgcgccatg gggtggactg ggtggcgcga    60

<210> SEQ ID NO 18
<211> LENGTH: 60
<212> TYPE: DNA
<213> ORGANISM: Artificial Sequence
<220> FEATURE:
<223> OTHER INFORMATION: JRO505 oligonucleotide

<400> SEQUENCE: 18
aaaatcgcgc cacccagtcc accccatggc gcagcatacg acggcccgca tcgtcctccc    60

<210> SEQ ID NO 19
<211> LENGTH: 100
<212> TYPE: DNA
<213> ORGANISM: Artificial Sequence
<220> FEATURE:
<223> OTHER INFORMATION: JRO452 oligonucleotide

```
<400> SEQUENCE: 19
caccgcttac gctgagtact tcgaaatatg cgggccgtat gggtgagccc gttaagattg      60
cgcgtggtgg cgcgagaggt ttcgaagtac tcagcgtaag                           100

<210> SEQ ID NO 20
<211> LENGTH: 100
<212> TYPE: DNA
<213> ORGANISM: Artificial Sequence
<220> FEATURE:
<223> OTHER INFORMATION: JRO453 oligonucleotide

<400> SEQUENCE: 20
aaaacttacg ctgagtactt cgaaacctct cgcgccacca cgcgcaatct taacgggctc      60
acccatacgg cccgcatatt tcgaagtact cagcgtaagc                           100

<210> SEQ ID NO 21
<211> LENGTH: 99
<212> TYPE: DNA
<213> ORGANISM: Artificial Sequence
<220> FEATURE:
<223> OTHER INFORMATION: JRO478 oligonucleotide

<400> SEQUENCE: 21
caccgcttac gctgagtact tcgaatgcgg gccctagacg cgctgccgtg gaggaggagg      60
ttggtggcgc gagaggtggt tcgaagtact cagcgtaag                            99

<210> SEQ ID NO 22
<211> LENGTH: 80
<212> TYPE: DNA
<213> ORGANISM: Artificial Sequence
<220> FEATURE:
<223> OTHER INFORMATION: JRO479 oligonucleotide

<400> SEQUENCE: 22
aaaacttacg ctgagtactt cgaaccacct ctcgcgccac caacctcctc ctccacggca      60
gcgcgtctag ggcccgcatt                                                80

<210> SEQ ID NO 23
<211> LENGTH: 106
<212> TYPE: DNA
<213> ORGANISM: Artificial Sequence
<220> FEATURE:
<223> OTHER INFORMATION: JRO480 oligonucleotide

<400> SEQUENCE: 23
caccgcttac gctgagtact tcgaaacaag gaggacgatg cgggccgtcg tatgctgcgc      60
catggggtgg actgggtggc gcgaagttcg aagtactcag cgtaag                    106

<210> SEQ ID NO 24
<211> LENGTH: 106
<212> TYPE: DNA
<213> ORGANISM: Artificial Sequence
<220> FEATURE:
<223> OTHER INFORMATION: JRO481 oligonucleotide

<400> SEQUENCE: 24
aaaacttacg ctgagtactt cgaacttcgc gccacccagt ccaccccatg gcgcagcata      60
cgacggcccg catcgtcctc cttgtttcga agtactcagc gtaagc                    106

<210> SEQ ID NO 25
```

<211> LENGTH: 107
<212> TYPE: DNA
<213> ORGANISM: Artificial Sequence
<220> FEATURE:
<223> OTHER INFORMATION: JRO531 oligonucleotide

<400> SEQUENCE: 25

```
caccgcttac gctgagtact tcgaaggagg acgatgcggg ctatcgcagc tctcgcgccg      60
atggaggagg tggtggcgcg agaggtgttc gaagtactca gcgtaag                  107
```

<210> SEQ ID NO 26
<211> LENGTH: 107
<212> TYPE: DNA
<213> ORGANISM: Artificial Sequence
<220> FEATURE:
<223> OTHER INFORMATION: JRO531 oligonucleotide

<400> SEQUENCE: 26

```
aaaacttacg ctgagtactt cgaacacctc tcgcgccacc acctcctcca tcggcgcgag     60
agctgcgata gcccgcatcg tcctccttcg aagtactcag cgtaagc                  107
```

<210> SEQ ID NO 27
<211> LENGTH: 95
<212> TYPE: DNA
<213> ORGANISM: Artificial Sequence
<220> FEATURE:
<223> OTHER INFORMATION: JRO482 oligonucleotide

<400> SEQUENCE: 27

```
caccgcttac gctgagtact tcgaatcggg cgccaatggg gaccgtccta tttgggatgt    60
cggtggcgcg aaatgttcga agtactcagc gtaag                               95
```

<210> SEQ ID NO 28
<211> LENGTH: 95
<212> TYPE: DNA
<213> ORGANISM: Artificial Sequence
<220> FEATURE:
<223> OTHER INFORMATION: JRO483 oligonucleotide

<400> SEQUENCE: 28

```
aaaacttacg ctgagtactt cgaacatttc gcgccaccga catcccaaat aggacggtcc    60
ccattggcgc ccgattcgaa gtactcagcg taagc                               95
```

<210> SEQ ID NO 29
<211> LENGTH: 109
<212> TYPE: DNA
<213> ORGANISM: Artificial Sequence
<220> FEATURE:
<223> OTHER INFORMATION: JRO484 oligonucleotide

<400> SEQUENCE: 29

```
caccgcttac gctgagtact tcgaatggag gacgatgcgg gcacctggcc ccgaaaaatt    60
tcgggttgag ctggtggcgc gagaggtggt tcgaagtact cagcgtaag               109
```

<210> SEQ ID NO 30
<211> LENGTH: 109
<212> TYPE: DNA
<213> ORGANISM: Artificial Sequence
<220> FEATURE:
<223> OTHER INFORMATION: JRO485 oligonucleotide

<400> SEQUENCE: 30

```
aaaacttacg ctgagtactt cgaaccacct ctcgcgccac cagctcaacc cgaaatttt     60
```

```
cggggccagg tgcccgcatc gtcctccatt cgaagtactc agcgtaagc              109
```

<210> SEQ ID NO 31
<211> LENGTH: 109
<212> TYPE: DNA
<213> ORGANISM: Artificial Sequence
<220> FEATURE:
<223> OTHER INFORMATION: JRO529 oligonucleotide

<400> SEQUENCE: 31

```
caccgcggag acagcgacga agagcataag gaggacgatg cgggccgtcg tatgctgcgc   60 catgggtgg actgggtggc gcagagagc tcttcgtcgc tgtctccgc                109
```

<210> SEQ ID NO 32
<211> LENGTH: 109
<212> TYPE: DNA
<213> ORGANISM: Artificial Sequence
<220> FEATURE:
<223> OTHER INFORMATION: JRO530 oligonucleotide

<400> SEQUENCE: 32

```
aaaagcggag acagcgacga agagctctct cgcgccaccc agtccacccc atggcgcagc   60
atacgacggc ccgcatcgtc ctccttatgc tcttcgtcgc tgtctccgc              109
```

<210> SEQ ID NO 33
<211> LENGTH: 78
<212> TYPE: DNA
<213> ORGANISM: Artificial Sequence
<220> FEATURE:
<223> OTHER INFORMATION: JRO469 oligonucleotide

<400> SEQUENCE: 33

```
taatacgact cactataggg aggacgatgc gggccgtatg ggtgagcccg ttaagattgc   60
gcgtggtggc gcgagagg                                                 78
```

<210> SEQ ID NO 34
<211> LENGTH: 78
<212> TYPE: DNA
<213> ORGANISM: Artificial Sequence
<220> FEATURE:
<223> OTHER INFORMATION: JRO493 oligonucleotide

<400> SEQUENCE: 34

```
cctctcgcgc caccacgcgc aatcttaacg ggctcaccca tacggcccgc atcgtcctcc   60
ctatagtgag tcgtatta                                                 78
```

<210> SEQ ID NO 35
<211> LENGTH: 115
<212> TYPE: DNA
<213> ORGANISM: Artificial Sequence
<220> FEATURE:
<223> OTHER INFORMATION: JRO512 oligonucleotide

<400> SEQUENCE: 35

```
taatacgact cactataggg cttacgctga gtacttcgaa atatgcgggc cgtatgggtg   60
agcccgttaa gattgcgcgt ggtggcgcga gaggtttcga agtactcagc gtaag       115
```

<210> SEQ ID NO 36
<211> LENGTH: 115
<212> TYPE: DNA
<213> ORGANISM: Artificial Sequence
<220> FEATURE:

```
<223> OTHER INFORMATION: JR0514 oligonucleotide

<400> SEQUENCE: 36
cttacgctga gtacttcgaa acctctcgcg ccaccacgcg caatcttaac gggctcaccc      60
atacggcccg catatttcga agtactcagc gtaagcccta tagtgagtcg tatta          115

<210> SEQ ID NO 37
<211> LENGTH: 78
<212> TYPE: DNA
<213> ORGANISM: Artificial Sequence
<220> FEATURE:
<223> OTHER INFORMATION: JR0527 oligonucleotide

<400> SEQUENCE: 37
taatacgact cactataggg aggacgatgc gggccgtcgt atgctgcgcc atggggtgga      60
ctgggtggcg cgagagag                                                   78

<210> SEQ ID NO 38
<211> LENGTH: 78
<212> TYPE: DNA
<213> ORGANISM: Artificial Sequence
<220> FEATURE:
<223> OTHER INFORMATION: JR0528 oligonucleotide

<400> SEQUENCE: 38
ctctctcgcg ccacccagtc cacccatgg cgcagcatac gacggcccgc atcgtcctcc       60
ctatagtgag tcgtatta                                                   78

<210> SEQ ID NO 39
<211> LENGTH: 22
<212> TYPE: DNA
<213> ORGANISM: Artificial Sequence
<220> FEATURE:
<223> OTHER INFORMATION: JR0541 oligonucleotide

<400> SEQUENCE: 39
cttacgctga gtacttcgaa at                                              22

<210> SEQ ID NO 40
<211> LENGTH: 20
<212> TYPE: DNA
<213> ORGANISM: Artificial Sequence
<220> FEATURE:
<223> OTHER INFORMATION: JR0456 oligonucleotide

<400> SEQUENCE: 40
tcttaacggg ctcacccata                                                 20
```

CONTINUOUSLY EXPRESSED THERAPEUTIC RNAS FOR TARGETED PROTEIN BINDING AND METHODS FOR THEIR USE

PRIORITY CLAIM

This application claims the benefit of U.S. Provisional Patent Application No. 62/415,919, filed Nov. 1, 2016, which is incorporated herein by reference in its entirety, including drawings, as if fully set forth herein.

STATEMENT OF GOVERNMENT INTEREST

The present invention was made with government support under Grant Nos. P30CA033572, AI029329 and AI042552 awarded by the National Institutes of Health. The Government has certain rights in the invention.

BACKGROUND

Human immunodeficiency virus (HIV), the cause of acquired immunodeficiency syndrome (AIDS), is estimated to affect 36.7 million people worldwide. Approximately 2 million people worldwide become newly infected with HIV each year. HIV rapidly evolves by altering expression of certain viral components making HIV difficult to treat, and to date, nearly impossible to cure. The current standard of treatment uses a combinatorial approach referred to as anti-HIV therapy (ART). While ART reduces overall levels of the HIV in a patient, ART is not curative. Patients undergoing ART endure high costs for treatment and are at risk for suffering from side effects associated with this lifelong therapy.

Gene therapy, a treatment successfully used for other diseases, has been studied as an alternative treatment to ART. One of the major challenges in treating HIV with gene therapy involves its rapidly evolving genome. By altering gene sequences, HIV evades certain treatments to become drug resistant. Early attempts of treating HIV using combinatorial gene therapy included both RNA and protein based strategies that were effective in cell culture and animal models (Li, et al., 2005; Asparuhova, et al., 2008; Anderson, et al., 2009; Chung, et al., 2014). However, these strategies may not be sufficient to reduce HIV, or cure HIV/AIDS, in a patient.

Ribonucleic acid (RNA) aptamers (RNA aptamers and aptamers) are short, single-stranded RNA molecules that fold into stable three-dimensional shapes and are useful for binding to certain structural features of target molecules. RNA aptamers having high affinity and specificity for target molecules, such as proteins, have previously been selected from complex libraries using the Selective Enrichment of Ligands by Exponential Enrichment (SELEX) protocol (Tuerk and Gold, 1990; Ellington and Szostak, 1992). Most therapeutic RNA aptamers are exogenously administered to cells that express a target molecule (e.g., a target cell) by binding to extracellular domains of certain cell surface proteins. These have been used to inhibit a function of the target molecule or as vehicles to deliver a therapeutic agent to the target cell. RNA aptamers having high binding affinity for some HIV specific molecules (e.g., reverse transcriptase (RT or Rev), glycoprotein120 (gp120), group specific antigen (Gag) and protease) have also been identified and isolated (Zhou, et al., 2009; Famalingam, et al., 2011; Ditzler, et al., 2011; Whatley, et al., 2013; Shum, Zhou and Rossi, 2013; Duclair, et al., 2015).

Traditionally, RNA aptamers are transcribed from a DNA polymerase III (Pol III) promoter, such as a U6 promoter, and include defined start and termination sites. This allows for precise prediction of the length and structure of the expressed RNA aptamers. However, when expressed from the Pol III promoter, RNA transcripts corresponding to the aptamers lack an intrinsic nuclear export signal (e.g., a 5' cap and a polyA tail). As such, intrinsic Pol III transcripts are present in the nucleus, rather than the cytoplasm. While the nuclear export signal can be added to the DNA sequence encoding the aptamer, the signal may alter the structure of the aptamer and interfere with the aptamer's desired function, such as binding to certain structural features of target molecules. In this way, nuclear export signals may not be useful for certain RNA aptamers. As such, intrinsic Pol III transcripts have limited use for RNA aptamers designed to target cytoplasmic proteins. Accordingly, expression of functional aptamers in HIV-infected cells remains a major hurdle for successful application of gene therapy, having long-term stability, to HIV patients.

Thus, it is of importance to develop alternative methods for expressing functional target-specific aptamers that may be applied to a successful combinatorial anti-HIV gene therapy therapeutic approach.

SUMMARY

In some embodiments, RNA compositions are provided. In particular, RNA compositions comprising RNA aptamers that bind target molecules, such as cytoplasmic proteins, are provided. The cytoplasmic proteins can include an enzymatic protein. The RNA molecule that is used as an aptamer in accordance with the embodiments described herein may include a nucleotide sequence of CGTATGGGTGAGC-CCGTTAAGATTGCGCGT (SEQ ID NO:1). In certain embodiments, the RNA molecule may include one of the following nucleotide sequences:

```
                                    (SEQ ID NO: 2)
       ACCTGGCCCCGAAAAATTTCGGGTTGAGCT, (SEQ ID NO: 3)
       CCAATGGGGACCGTCCTATTTGGGATGTC, (SEQ ID NO: 4)
       TATCGCAGCTTTTGCGCCGATGGAGGAGGT,
       or (SEQ ID NO: 5)
       CGTCGTATGCTGCGCCATGGGGTGGACTG.
```

In some embodiments, the RNA aptamer may be expressed with another RNA molecule, such as an shRNA or an miRNA. In these embodiments, the RNA aptamer may be located within a structure of the shRNA, such as a stem-loop structure, or within the miRNA, such as a terminal loop. The co-expressed RNA aptamer may also be fused to the shRNA molecule or the miRNA molecule. The shRNA molecule or the miRNA may transport the enzymatic protein aptamer to a desired location within the cell. In other embodiments, the shRNA is an anti-HIV shRNA, such as an anti-HIV Tat-Rev shRNA, or the miRNA is an anti-HIV miRNA, such as an anti-HIV Tat-Rev miRNA. In some embodiments, the RNA aptamer binds to and inhibits activity of the enzymatic protein, such as an integrase and reverse transcriptase (RT). In these embodiments, the integrase is an HIV integrase. In other embodiments, the integrase is a reverse transcriptase (RT). In further embodiments, the RNA aptamer may be fused to an additional therapeutic agent. In additional embodiments, the RNA aptamer is part of a pharmaceutical composition which further comprises a pharmaceutical carrier.

In some embodiments, methods for delivering a therapeutic agent to an HIV-infected cell are provided. Such methods may include a step of contacting the HIV-infected cell with an RNA composition. The RNA composition may include an RNA aptamer and a therapeutic agent component. In some embodiments the RNA aptamer component includes an RNA molecule that specifically binds an enzymatic protein expressed by non-host DNA or non-host RNA, resulting in inhibition of activity of the enzymatic protein—such as those described herein. The step of binding the enzymatic protein with the RNA aptamer may be accomplished by administering the RNA composition to a subject intravenously (i.v.). The therapeutic agent component may include an shRNA molecule.

In other embodiments, methods for treating HIV are provided. Such a method may include a step of administering a therapeutically effective amount of an RNA aptamer and an shRNA molecule, or an miRNA molecule, wherein the RNA aptamer comprises an RNA molecule that specifically binds an enzymatic protein, and wherein the RNA aptamer inhibits activity of the enzymatic protein. The RNA molecule that is used as an aptamer in accordance with the embodiments described herein may include a nucleotide sequence of CGTATGGGTGAGCCCGTTAAGATT-GCGCGT (SEQ ID NO:1). In certain embodiments, the RNA molecule may include one of the following nucleotide sequences:

```
                                        (SEQ ID NO: 2)
ACCTGGCCCCGAAAAATTTCGGGTTGAGCT, (SEQ ID NO: 3)
CCAATGGGGACCGTCCTATTTGGGATGTC, (SEQ ID NO: 4)
TATCGCAGCTTTTGCGCCGATGGAGGAGGT,
or (SEQ ID NO: 5)
CGTCGTATGCTGCGCCATGGGGTGGACTG.
```

In some embodiments, the RNA aptamers may be part of a pharmaceutical composition for use in the methods of treating HIV. Said pharmaceutical compositions may further comprise a pharmaceutically acceptable carrier.

In further embodiments, methods for selecting an RNA aptamer having an affinity for a target molecule are provided. Such methods may include a step of generating a plurality of DNA molecules from an oligonucleotide library using suitable library generating technique. For example, in one embodiment, the step of generating a plurality of DNA molecules from an oligonucleotide library may be accomplished by using a T4 polymerase. In certain embodiments, the oligonucleotides of the library may include a 5' T7 promoter sequence, a variable middle region, and a 3' constant region. These methods may also include additional steps, such as, generating a plurality of RNA molecules from the plurality of DNA molecules, contacting the plurality of RNA molecules with a first target molecule in a solution having a first sodium chloride concentration and a first tRNA concentration, contacting the plurality of RNA molecules with a second target molecule in a solution having a second sodium chloride concentration and a second tRNA concentration, contacting the plurality of RNA molecules with a third target molecule, determining a sequence of one or more RNA molecules of the plurality that contacted the third target molecule, and identifying an RNA aptamer from the plurality of RNA molecules. In these steps, the variable middle region may include 30 or more nucleotides, the first sodium chloride concentration may fall within a range of 50 mM-100 mM, inclusive, the second sodium chloride concentration may fall within a range of 75 mM-150 mM, inclusive, the first tRNA concentration may fall within a range of 0 ug to 40 ug, inclusive, and the second tRNA concentration may fall within a range of 40 ug to 80 ug, inclusive. In addition, the concentration of the plurality of RNA molecules may be greater when contacting the first target molecule compared to the third target molecule.

BRIEF DESCRIPTION OF THE DRAWINGS

Many aspects of the present technology can be better understood with reference to the following drawings. Emphasis is placed on illustrating clearly the principles of the present technology.

FIGS. 1A-E illustrate multiple tagged integrase for SELEX according to some embodiments. (A) Codon optimization increased yield of active and inactive FLAG-IN. This Western blot shows expression levels of FLAG tagged original (wt), codon optimized active (D64) and codon optimized inactive (V64) integrase (IN) from transiently transfected HEK293 cells. The yield of codon optimized FLAG-IN was lower than FLAG-mCherry positive control. (B) FLAG-IN (D64) transiently expressed in HEK293 cells was purified by anti-FLAG M2 affinity gel (Sigma). Approximately 74% (compare lane 2 to lane 1) of FLAG-IN expressed from HEK293 cells was purified. (C) 10% of FLAG-IN purified from two 150 cm plates of HEK 293 cells was not detected by coomassie staining. 0.5 μg of purified HIS-IN and MBP-IN was added for comparison. (D) Schematic of multi-tagged SELEX strategy. (E) Typical change of aptamers binding during enrichment cycles. "*" marks the sample after one round of enrichment using HEK293 expressed FLAG-IN. High percentage binding at first two cycles may represent a high level of non-specific binding to HIS and MBP tags. Alternate high and low binding at later cycles may represent populations having higher binding affinity to MBP-IN than HIS-IN.

FIGS. 3A-3K illustrate the predicted secondary structures of the 15 most abundant aptamers according to some embodiments. The structure in panel A is shared between the most number of aptamers. S1R1 and S3R5 differ by a single base at (position 19) at the loop of the first stem-loop structure.

DETAILED DESCRIPTION

Figure 1B:
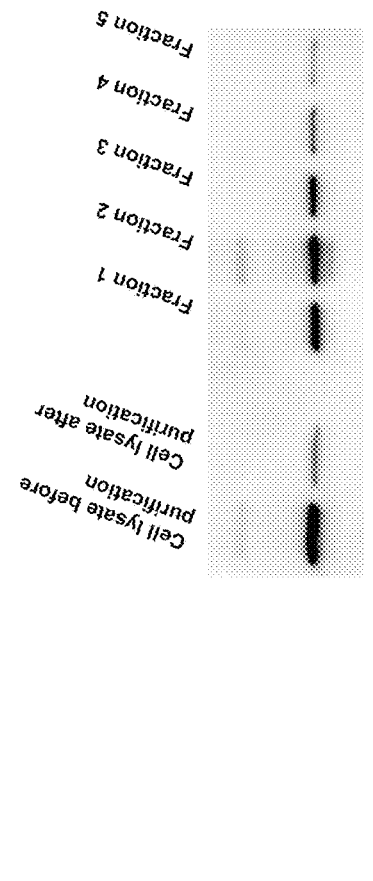

RNA compositions, aptamer fusions, systems for aptamer expression and selection as well as methods for their use are provided herein. According to the embodiments described herein, the RNA compositions including an aptamer may be used alone or in combination with therapeutic or diagnostic agents and molecules for treatment, diagnosis and monitoring of a subject in need thereof, for example, one infected with HIV. In some embodiments, the aptamers may be used in combination with an shRNA as a fusion, such as an aptamer-shRNA fusion, or as independent molecules, an anti-HIV lentivirus vector that transduces target cells to express a combination of a ribozyme, and an RNA decoy, ART therapy, and other treatments. In some embodiments, the aptamers may be used in combination with an miRNA as a fusion, such as an aptamer-miRNA fusion, or as independent molecules, an anti-HIV lentivirus vector that transduces target cells to express a combination of a ribozyme, and an RNA decoy, ART therapy, and other treatments. In certain embodiments, the aptamers are RNA aptamers.

In accordance with the present technology, aptamers may be expressed and selected using the multi-tag SELEX method described herein. As described in further detail below, multi-tag SELEX may select aptamers that bind to target molecules having low solubility and/or stability, such as certain proteins, including integrase. In some embodiments, the target molecules may be located outside of the nucleus, such as in the cytoplasm. The cytoplasmic protein may be an enzyme, such as a hydrolase, an isomerase, a ligase, a lyase, an oxidoreductase, or a transferase. In these embodiments, the aptamer may bind to the cytoplasmic protein, such as an enzyme, and inhibit its activity. For example, the aptamer may bind to integrase and inhibits integrase-mediated insertion of HIV DNA into the host genome. In these embodiments, aptamers may be incorporated into a molecule for transport out of the nucleus. For example, aptamers may be incorporated into an shRNA molecule (e.g., aptamer-shRNA fusions) at the terminal loop or into an miRNA molecule (e.g., aptamer-miRNA fusions), and processed by Dicer (e.g., an enzyme which cleaves the RNA aptamer from the shRNA or the miRNA). Once cleaved, the aptamer may fold into a three dimensional structure and bind a target molecule, such as the cytoplasmic protein. In these embodiments, the aptamer and the RNA aptamer become independent molecules. In some embodiments, the aptamer-shRNA fusions and/or the aptamer-miRNA fusions may be stably expressed. In other embodiments, the aptamer-shRNA fusions and/or the aptamer-miRNA fusions may be combined with additional therapeutic strategies in a combinatorial therapeutic approach. For example, the aptamer-shRNA and/or the aptamer-miRNA fusions may be combined with one or more additional shRNAs and/or miRNAs, such as an anti-HIV Tat-Rev shRNA or an anti-HIV Tat-Rev miRNA.

Further, the RNA compositions, the aptamer-shRNA fusions, and/or the aptamer-miRNA fusions may be expressed by one or more cells in need of treatment for a condition or disease, for imaging cells, or for monitoring a condition or disease in vivo. Specific delivery of genetic material encoding these aptamer-shRNA fusions and/or the aptamer-miRNA fusions to one or more target cells provides a persistent expression of the therapeutic aptamers for gene therapy. In this way, aptamer-shRNA fusion and/or the aptamer-miRNA fusion technology can be combined with other gene therapy strategies to treat the condition or disease.

Aptamer Component

In some embodiments, the RNA compositions, aptamer-shRNA fusions and/or the aptamer-miRNA fusions include an aptamer component for targeting particular molecules, such as proteins. These aptamers may be used for treating diseases, conditions, ailments, or other afflictions (also referred to herein as "diseases") associated with the target molecule. An "aptamer" is any suitable small molecule, such as a nucleic acid or a peptide molecule that binds specifically to a target, such as a small molecule, protein, nucleic acid, cell, tissue or organism. Aptamers that target specific proteins, such as cytoplasmic proteins, can be employed as therapeutic molecules thereby reducing off-target effects or other unwanted side effects of other therapeutic strategies, such as ART.

In some embodiments, the aptamer component is a nucleic acid aptamer. Such aptamers with binding affinities in nanomolar range have been utilized for flexible applications ranging from diagnostic to therapeutic assay formats (Zhou, et al., 2009). The nucleic acid that forms the nucleic acid aptamer may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid aptamer can be replaced with a hydrocarbon linker or a polyether linker provided that the binding affinity and selectivity of the nucleic acid aptamer is not substantially reduced by the substitution.

Nucleic acids in accordance with the embodiments described herein may include nucleotides entirely of the types found in naturally occurring nucleic acids, or may instead include one or more nucleotide analogs or have a structure that otherwise differs from that of a naturally occurring nucleic acid. U.S. Pat. Nos. 6,403,779, 6,399,754, 6,225,460, 6,127,533, 6,031,086, 6,005,087, 5,977,089, disclose a wide variety of specific nucleotide analogs and modifications that may be used, and are hereby incorporated by reference as if fully set forth herein. Also see Crooke, S. Antisense Drug Technology: Principles, Strategies, and Applications (1st ed), Marcel Dekker; ISBN: 0824705661; 1st edition (2001), which is also hereby incorporated by reference as if fully set forth herein. For example, 2'-modifications include halo, alkoxy and allyloxy groups. In some embodiments, the 2'-OH group is replaced by a group selected from H, OR, R, halo, SH, SR, $NH_2$, NHR, $NR_2$ or CN, wherein R is C1-C6 alkyl, alkenyl, or alkynyl, and halo is F, Cl, Br, or I. Examples of modified linkages include phosphorothioate and 5'-N-phosphoramidite linkages.

Nucleic acids having a variety of different nucleotide analogs, modified backbones, or non-naturally occurring internucleoside linkages can be utilized in accordance with the embodiments described herein. Nucleic acids may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. The nucleotide analogs or other modification(s) may be located at any position(s) of a nucleic acid such that the function of the nucleic acid is not substantially affected. To give but one example, modifications may be located at any position of an aptamer component such that the ability of the aptamer to specifically bind to the target is not substantially affected. The modified region may be at the 5'-end and/or the 3'-end of one or both strands. For example, modified nucleic acid aptamers in which approximately 1-5 residues at the 5' and/or 3' end of either of both strands are nucleotide analogs and/or have a backbone modification have been employed. The modification may be a 5' or 3' terminal modification.

Selection of aptamers may be accomplished by any suitable method known in the art, including SELEX (Systemic Evolution of Ligands by Exponential enrichment). In some embodiments, multi-tag SELEX may be used in accordance with the present technology. Contrary to the SELEX process, which has been established as a general technique for aptamer selection, multi-tag SELEX described herein selects for aptamers that target proteins having low solubility and/or stability, such as cytoplasmic proteins and others. Each multi-tag SELEX experiment includes its own challenges and is not guaranteed to work for all targets. Similar to SELEX, multi-tag SELEX is not predictable nor is it standardized for use with any target. Instead, the multi-tag SELEX process must be optimized and customized for each particular target molecule.

Many factors are important for successful aptamer selection. For example, the target molecule should be stable and easily reproduced for each round of multi-tag SELEX, because the multi-tag SELEX process involves multiple rounds of binding, selection, and amplification to enrich the nucleic acid molecules. In addition, the nucleic acids that exhibit specific binding to the target molecule have to be present in the initial library. Thus, it is advantageous to produce a highly diverse nucleic acid pool. Because the starting library is not guaranteed to contain aptamers to the target molecule, the multi-tag SELEX process for a single target may need to be repeated with different starting libraries. Aptamer selection using multi-tag SELEX is unpredictable. Even when all of the factors are optimized for successful aptamer selection, the multi-tag SELEX process does not always yield viable aptamers for every target molecule.

In some embodiments, selection of an aptamer may be accomplished by applying a multi-tag SELEX process against a molecule to obtain aptamers that selectively target an epitope on the molecule. The molecule may be an isolated molecule, a purified molecule, a recombinant molecule, or a naturally occurring molecule. In addition, the molecule may be expressed with a tag to aid in isolating the molecule and bound aptamers. Useful tags include those known to one of ordinary skill in the art, and include, but are not limited to, human influenza hemagglutinin (HA), polyhistidine (His), maltose binding protein (MBP), glutathione-s-transferase (GST), c-myc peptide (Myc), Vesicular Somatitis Virus (VSV), streptavidin (SA), and FLAG.

In addition, the multi-tag SELEX process may include an approach that includes selection of the aptamer library against more than one molecule. In these embodiments, the molecules used for selection may be isoforms of the same molecule to enrich for aptamers against molecules having low solubility and/or stability, such as cytoplasmic proteins. For example, the isoforms may include a bacterial expressed molecule, a molecule expressed in yeast, and/or a molecule expressed by mammalian cells. As described in detail in the Examples below, a multi-tag SELEX process was used to generate a panel of RNA aptamers that are able to bind to integrase, and are secreted from the nucleus into the cytoplasm when incorporated into the terminal loop of an shRNA molecule.

In some embodiments, the multi-tag SELEX method may be performed as described by Zhou et al with the following modifications. 2'F-RNA aptamers may be selected from a library of randomized sequences. The library of randomized sequences may include a plurality of RNA oligonucleotides each having a sequence of 5'-TAATACGACTCAC-TATAGGGAGGACGATGCGGGC-30N-GGTGGCGCGA-GAGGTG-3' (SEQ ID NO:6). In other embodiments, the RNA oligonucleotides may have other randomized sequences from about 20 nucleotides in length to about 50 nucleotides in length, inclusive. This sequence includes a 5' T7 promoter, a 30N variable middle region and a 3' constant region. 30N represents 30 nucleotide (nt) sequences formed by equimolar incorporation of A, G, C, and U at each position. The randomized library may be transcribed into synthetic DNA templates with NTPs (2'F UTP, 2'F CTP, GTP, ATP) using methods known to those of ordinary skill in the art that include an RNA polymerase having reduced fidelity to increase the complexity of the library. For example, T4 RNA polymerase may be used for transcription of the synthetic DNA sequences. In addition, 2'F-Py RNAs may be used to increase the nuclease resistance. Multi-tag SELEX selection rounds may include more than one target molecule, as described above. For example, the selection rounds may include two bacterially expressed proteins and a mammalian expressed protein. As demonstrated in the Examples below, multi-tag SELEX was performed with His-tagged and MBP-tagged bacterially expressed proteins as well as a mammalian expressed FLAG-tag protein. In some embodiments, these proteins may be integrase, such as HIV integrase.

In some embodiments, the multi-tag SELEX method includes multiple rounds of selection by contacting the molecule with the library. In each round, the library may be combined with the same molecule or, the library may be combined with a different molecule. For example, in the early rounds of aptamer selection, two molecules may be used alternatively for in vitro selection. These molecules may or may not be tagged (e.g., with MBP or His). The early selection rounds may occur in any suitable buffer known to one of ordinary skill in the art. For example, the suitable buffer may be a binding buffer (e.g., PBS W/O Ca2+ and Mg2+, 5 mM MgCl2, 0.01% BSA). As the selection rounds progress, the concentration of one or more ingredients of the binding buffer may be modified to increase stringency of each round of selection. For example, the concentrations of NaCl and tRNA may be gradually increased with each round of selection (or alternate rounds of selection) and the concentration of aptamer RNA may be gradually decreased with each round of selection (or alternate rounds of selection). Aptamers which bound to the target molecule during the rounds of selection may be sequenced using one or more methods know to one of ordinary skill in the art, such as high throughput deep sequencing and sequence analysis.

According to the embodiments described herein, the aptamer component of the RNA compositions, aptamer-shRNA fusions and/or the aptamer-miRNA fusions is an aptamer that targets and specifically binds to an enzymatic protein, (e.g., integrase) that is expressed by cells infected with HIV. Other proteins that may be targeted by the aptamer component include, but are not limited to, gag, gag-pol fusion protein precursor, pro (protease), reverse transcriptase (RT), env, tat (Trans-Activator of Transcription), rev, nef (negative factor), vpr, vpu (membrane phosphoprotein), vif, and any other suitable HIV associated-protein. In some embodiments, the aptamer component binds to and inhibits activity of RT.

In one embodiment, the aptamer component of the RNA compositions, aptamer-shRNA fusions and/or the aptamer-miRNA fusions described herein is an aptamer that binds HIV-integrase. Examples of HIV-integrase aptamers, according to the embodiments described herein, are shown in FIGS. 2B and 3A-3K. Oligonucleotide sequences that may be useful to generate certain HIV-integrase aptamers are provided in Table 1. Examples of additional anti-HIV aptamers can be found in Zhou et al., Nucleic Acids Res, 2009. 37(9): p. 3094-109, which is hereby incorporated by reference in its entirety as if fully set forth herein.

TABLE 1

Oligonucleotides

| Target | Oligo Name | Oligo Sequence |
|---|---|---|
| Aptamer Library | | |
| | | TAATACGACTCACTATAGGGAGGACGATGC GGGCnnnnnnnnnnnnnnnnnnnnnnnnnnnnnnnGG TGGCGC GAGAGGTG (SEQ ID NO: 6) |
| Forward primer T7 promoter + library constant region | | TAATACGACTCACTATAGGGAGGACGATGC GG (SEQ ID NO: 7) |
| Library reverse primer | | CACCTCTCGCGCCACC (SEQ ID NO: 8) |
| For RNA Expression | | |
| shLuc | JR0450 | CACCGCTTACGCTGAGTACTTCGAAATTGAA GCTTGTTTCGAAGTACTCAGCGTAAG (SEQ ID NO: 9) |
| | JR0451 | AAAACTTACGCTGAGTACTTCGAAACAAGCT TCAATTTCGAAGTACTCAGCGTAAGC (SEQ ID NO: 10) |
| shS1 | JR0535 | caccGCGGAGACAGCGACGAAGAGCattgaagct tgtGCTCTTCGTCGCTGTCTCCGC (SEQ ID NO: 11) |
| | JR0536 | aaaaGCGGAGACAGCGACGAAGAGCacaagctt caatGCTCTTCGTCGCTGTCTCCGC (SEQ ID NO: 12) |
| S1R1 | JR0500 | caccGATGCGGGCCGTATGGGTGAGCCCGTT AAGATTGCGCGTGGTGGCGCGAG (SEQ ID NO: 13) |
| | JR0501 | aaaaCTCGCGCCACCACGCGCAATCTTAACG GGCTCACCCATACGGCCCGCATC (SEQ ID NO: 14) |
| S3R1 | JR0502 | caccGCGGGCCCTAGACGCGCTGCCGTGGA GGAGGAGGTTGGTGGCGCGAGAGGTG (SEQ ID NO: 15) |
| | JR0503 | aaaaCACCTCTCGCGCCACCAACCTCCTCCT CCACGGCAGCGCGTCTAGGGCCCGC (SEQ ID NO: 16) |
| S3R3 | JR0504 | caccGGGAGGACGATGCGGGCCGTCGTATG CTGCGCCATGGGGTGGACTGGGTGGCGCG A (SEQ ID NO: 17) |
| | JR0505 | aaaaTCGCGCCACCCAGTCCACCCCATGGC GCAGCATACGACGGCCCGCATCGTCCTCCC (SEQ ID NO: 18) |
| shLuc-S1R1 | JR0452 | caccGCTTACGCTGAGTACTTCGAAAtATGCG GGCCGTATGGGTGAGCCCGTTAAGATTGCG CGTGGTGGC GCGAGAGgTTTCGAAGTACTCAGCGTAAG (SEQ ID NO: 19) |

TABLE 1-continued

Oligonucleotides

| Target | Oligo Name | Oligo Sequence |
|---|---|---|
| | JRO453 | aaaaCTTACGCTGAGTACTTCGAAAcCTCTCG CGCCACCACGCGCAATCTTAACGGGCTCAC CCATACGGCC CGCATaTTTCGAAGTACTCAGCGTAAGC (SEQ ID NO: 20) |
| shLuc-S3R1 | JRO478 | caccGCTTACGCTGAGTACTTCGAAtGCGGGC CCTAGACGCGCTGCCGTGGAGGAGGAGGTT GGTGGCGC GAGAGGTGgTTCGAAGTACTCAGCGTAAG (SEQ ID NO: 21) |
| | JRO479 | aaaaCTTACGCTGAGTACTTCGAAcCACCTCT CGCGCCACCAACCTCCTCCTCCACGGCAGC GCGTCTAGG GCCCGCaTT (SEQ ID NO: 22) |
| shLuc-S3R3 | JRO480 | caccGCTTACGCTGAGTACTTCGAAacaaGGAG GACGATGCGGGCCGTCGTATGCTGCGCCAT GGGGTGGA CTGGGTGGCGCGAagTTCGAAGTACTCAGCG TAAG (SEQ ID NO: 23) |
| | JRO481 | aaaaCTTACGCTGAGTACTTCGAActTCGCGC CACCCAGTCCACCCCATGGCGCAGCATACG ACGGCCCGC ATCGTCCTCCttgtTTCGAAGTACTCAGCGTAA GC (SEQ ID NO: 24) |
| shLuc-S3R4 | JRO531 | caccGCTTACGCTGAGTACTTCGAAGGAGGAC GATGCGGGCTATCGCAGCTcTcGCGCCGATG GAGGAGGT GGTGGCGCGAGAGGTGTTCGAAGTACTCAG CGTAAG (SEQ ID NO: 25) |
| | JRO532 | aaaaCTTACGCTGAGTACTTCGAACACCTCTC GCGCCACCACCTCCTCCATCGGCGCgAgAG CTGCGATAG CCCGCATCGTCCTCCTTCGAAGTACTCAGCG TAAGC (SEQ ID NO: 26) |
| shLuc-S4R6 | JRO482 | caccGCTTACGCTGAGTACTTCGAAtCGGGCG CCAATGGGGACCGTCCTATTTGGGATGTCG GTGGCGCGA AATgTTCGAAGTACTCAGCGTAAG (SEQ ID NO: 27) |
| | JRO483 | aaaaCTTACGCTGAGTACTTCGAAcATTTCGC GCCACCGACATCCCAAATAGGACGGTCCCC ATTGGCGCCC GaTTCGAAGTACTCAGCGTAAGC (SEQ ID NO: 28) |
| shLuc-S4R2 | JRO484 | CACCGCTTACGCTGAGTACTTCGAATGGAGG ACGATGCGGGCACCTGGCCCCGAAAAATTT CGGGTTGAG CTGGTGGCGCGAGAGGTGGTTCGAAGTACT CAGCGTAAG (SEQ ID NO: 29) |
| | JRO485 | AAAACTTACGCTGAGTACTTCGAACCACCTC TCGCGCCACCAGCTCAACCCGAAATTTTTCG GGGCCAGGT GCCCGCATCGTCCTCCATTCGAAGTACTCA GCGTAAGC (SEQ ID NO: 30) |
| shS1-S3R3 | JRO529 | caccGCGGAGACAGCGACGAAGAGCataaGGA GGACGATGCGGGCCGTCGTATGCTGCGCCA TGGGGTGG ACTGGGTGGCGCGAgagaGCTCTTCGTCGCT GTCTCCGC (SEQ ID NO: 31) |
| | JRO530 | aaaaGCGGAGACAGCGACGAAGAGCtctcTCG CGCCACCCAGTCCACCCCATGGCGCAGCAT ACGACGGC CCGATCGTCCTCCttatGCTCTTCGTCGCTG TCTCCGC (SEQ ID NO: 32) |

Mobility Assay

| T7-S1R1 | JRO469 | TAATACGACTCACTATAGGGAGGACGATGCG GGCCGTATGGGTGAGCCCGTTAAGATTGCG CGTGGTGGCGCGAGAGG (SEQ ID NO: 33) |

TABLE 1-continued

Oligonucleotides

| Target | Oligo Name | Oligo Sequence |
|---|---|---|
| | JR0493 | CCTCTCGCGCCACCACGCGCAATCTTAACG GGCTCACCCATACGGCccgcatcgtcctccctatagtg agtcgtatta (SEQ ID NO: 34) |
| T7-shLuc-S1R1 | JR0512 | taatacgactcactataggGCTTACGCTGAGTACTTC GAAAtATGCGGGCCGTATGGGTGAGCCCGTT AAGATTG CGCGTGGTGGCGCGAGAGgTTTCGAAGTAC TCAGCGTAAG (SEQ ID NO: 35) |
| | JR0514 | CTTACGCTGAGTACTTCGAAACCTCTCGCGC CACCACGCGCAATCTTAACGGGCTCACCCAT ACGGCCCGC ATATTTCGAAGTACTCAGCGTAAGCCCTATA GTGAGTCGTATTA (SEQ ID NO: 36) |
| T7-S3R3 | JR0527 | TAATACGACTCACTATAGGgaggacgatgcgggcc gtcgtatgctgcgccatggggtggactgggtggcgcgagagag (SEQ ID NO: 37) |
| | JR0528 | ctctctcgcgccacccagtccacccccatggcgcagcatacgac ggcccgcatcgtcctcCCTATAGTGAGTCGTATTA (SEQ ID NO: 38) |

Northern Blot Probes

| | | |
|---|---|---|
| Luciferase probe | JR0541 | CTTACGCTGAGTACTTCGAAAT (SEQ ID NO: 39) |
| S1 R1 probe | JR0456 | TCTTAACGGGCTCACCCATA (SEQ ID NO: 40) | shRNA Component and the miRNA Component

In some embodiments, the RNA compositions and/or aptamer-shRNA fusions includes an shRNA component, such as an shRNA molecule, that is expressed intracellularly as part of a therapeutic payload. In other embodiments, the RNA compositions and/or aptamer-miRNA fusions includes an miRNA component, such as an miRNA molecule, that is expressed intracellularly as part of a therapeutic payload. The shRNA component and/or the miRNA component may mimic pri-microRNA or pre-microRNA. Pre-miRNAs are exported to the cytoplasm by Exportin 5 that recognize the 3' two base overhangs of the stem-loop structures (Okada, et al., 2009; Lee et al., 2011). Some pre-miRNAs contain large loops; however, these pre-miRNAs are still efficiently exported to the cytoplasm, cleaved by Dicer, loaded into RNA Induced Silencing Complex (RISC), and silence their target mRNAs (Feng, et al., 2012; Winter et al., 2013). Similarly, shRNAs and miRNAs may be processed by Drosha and may be exported from the nucleus by exportin 5. Once exported to the cytoplasm, the pre-shRNA, shRNA-aptamer fusion, and/or the pre-miRNA may be processed by Dicer to release the shRNA or the miRNA and the aptamer. Once released, the miRNA or the shRNA is loaded on to the RISC to suppress translation of the mRNA targeted by the shRNA or the miRNA. In these embodiments, the aptamer may be incorporated into the shRNA or the miRNA such as a loop structure. The shRNA and the miRNA loop structures include a large loop and a terminal loop.

As mentioned above, HIV proceeds through several stages within an infected cell. Integrase is localized to the cytoplasm of infected cells throughout many of these stages. In this way, transporting aptamers to the cytoplasm, for example by using shRNA and/or miRNA, may inhibit the enzymatic activity of HIV integrase throughout these several stages. In some embodiments, the target proteins may be proteins having low solubility and/or proteins that are unstable. Unstable proteins may refer to those proteins which have three-dimensional structures which change. In certain embodiments, cytoplasmic proteins may also have low solubility and/or be unstable.

In some embodiments, the shRNA component and/or the miRNA component acts as a therapeutic agent to suppress expression of a target protein or peptide associated a pathological moiety such as a HIV-associated protein (e.g., HIV trans-activator of transcription (HIV-Tat), HIV reverse transcriptase (HIV-Rev)), a free HIV (e.g., HIV, CMV), or a protein associated with a particular disease. In this case, the shRNA component and/or the miRNA component serves to silence translation of the target protein by directing RISC to degrade the precursor mRNA. In certain embodiments, the RNA composition, the aptamer-shRNA fusion, and/or the aptamer-miRNA fusion may include more than one shRNA molecule. In these embodiments, the shRNA molecules and/or the miRNA molecules may target the same molecule, or different molecules that may or may not be associated with HIV.

Aptamer Fusions

According to some embodiments, aptamer fusions (e.g., aptamer-shRNA fusions, and/or aptamer-miRNA fusions) are provided herein. The aptamer-fusion may include an aptamer component fused to an shRNA component and/or an miRNA component. As used herein, the terms "fused", "fused to," or "fusion" refers to two or more entities or the state of two or more entities which are linked by a direct or indirect covalent or non-covalent interaction. In some embodiments, an association is covalent. In some embodiments, a covalent association is mediated by a linker moiety. In some embodiments, an association is non-covalent (e.g. charge interactions, affinity interactions, metal coordination, physical adsorption, host-guest interactions, hydrophobic interactions, PI stacking interactions, hydrogen bonding interactions such as with "sticky sequences," van der Waals interactions, magnetic interactions, electrostatic interactions, dipole-dipole interactions, etc).

In some embodiments, the aptamer fusions comprise one aptamer. In other embodiments, the aptamer fusions comprise more than one aptamer. For example, the aptamer-shRNA fusions may comprise two aptamers, three aptamers, four aptamers, five aptamers, 10 aptamers, 15 aptamers, 20 aptamers, or more than 20 aptamers. In these other embodiments, each aptamer may bind to a different target molecule, different locations on the same target molecule, or a combination thereof.

In some embodiments, the aptamer fusions comprise one shRNA. In other embodiments, the aptamer fusions comprise more than one shRNA. For example, the aptamer-shRNA fusions may comprise two shRNAs, three shRNAs, four shRNAs, five shRNAs, 10 shRNAs, 15 shRNAs, 20 shRNAs, or more than 20 shRNAs. In these other embodiments, each shRNA may target a different molecule, by DNA, mRNA, other polynucleic acids, or a combination thereof.

In some embodiments, the aptamer fusions comprise one miRNA. In other embodiments, the aptamer fusions comprise more than one miRNA. For example, the aptamer-miRNA fusions may comprise two miRNAs, three miRNAs, four miRNAs, five miRNAs, 10 miRNAs, 15 miRNAs, 20 miRNAs, or more than 20 miRNAs. In these other embodiments, each miRNA may target a different molecule, by DNA, mRNA, other polynucleic acids, or a combination thereof.

According to some embodiments, the aptamer fusions may include one or more therapeutic agents to form a therapeutic aptamer fusion. A "therapeutic agent" as used herein is an atom, molecule, or compound that is useful in the treatment of a HIV or other conditions described herein. Examples of therapeutic agents that may be fused to the aptamer include, but are not limited to, nucleic acid molecules (e.g., mRNA molecules or cDNA molecules), encoding expression of therapeutic antibodies and fragments thereof, toxins, enzymes (e.g., enzymes to cleave prodrugs to a cytotoxic agent within the HIV-infected cell), nucleases, hormones, immunomodulators, and photoactive agents. Other examples of therapeutic agents that may be fused to the aptamer include, but are not limited to nucleic acid molecules (e.g., RNAi molecules such as siRNA or shRNA) silencing expressing of, and/or reducing expression of HIV-associated molecules such as enzymes, capsid components, envelope components, glycoproteins, and other proteins associated with propagating an HIV infection within a host.

In certain embodiments, the aptamer is fused to a nucleic acid molecule which acts as the therapeutic agent. In some embodiments, the nucleic acid molecule that is fused to the aptamer is an RNA molecule. RNA molecules that may be fused to the aptamer in accordance with the embodiments described herein may include, but are not limited to, ribosomal RNA (rRNA), messenger RNA (mRNA), transfer RNA (tRNA), small nuclear RNA (snRNA), small nucleolar RNA (snoRNA), small cytoplasmic RNA (scRNA), micro RNA (miRNA), small interfering RNA (siRNA), and small hairpin RNA (shRNA). In some embodiments, the shRNA component described above may also be a therapeutic shRNA.

In one embodiment, the nucleic acid molecule is an RNA interference molecule (e.g., an siRNA, an shRNA, or an miRNA molecule) that, when expressed by a cell, suppress or silences expression of one or more HIV-associated genes or of any protein or peptide that is associated with HIV by targeting an mRNA molecule. In one embodiment, the RNA interference molecule is an siRNA, shRNA, miRNA or other RNA molecule which targets an mRNA molecule which encodes gag, gag-pol precursor, pro, RT, env, tat, rev, nef, vpr, vpu, vif, or any other RNA molecule that inhibits expression of a protein that is associated with HIV.

In some embodiments, the aptamer and the shRNA or the miRNA of the fusion may target a protein and an mRNA. In these embodiments, the aptamer and the shRNA or the miRNA may target the same gene, for example, by targeting the protein (e.g., with the aptamer) and the corresponding mRNA (e.g., with the shRNA or the miRNA), two different genes using the example described above, or one protein and one non-coding RNA using the example described above. While one aptamer fusion may be designed to bind targets, more than one aptamer fusion may also be designed. When more than one aptamer fusion is designed, multiplexed vectors may be used to express the multiple fusions from a single transcript. Multiplex vectors have been described by others (Chung et al., 2014).

In another embodiment, the nucleic acid molecule is an mRNA molecule that is expressed intracellularly as part of a therapeutic or diagnostic payload. Alternatively, the secondary mRNA component may include a cDNA molecule. Further, the secondary mRNA component may express a full wild type protein or peptide in a target cell, or may express at least the biologically active portion of the protein or peptide. When expressed within the target cell, the mRNA molecule acts as a therapeutic agent by expressing a protein or peptide that is missing or altered in the target cell, a cytotoxic protein or peptide to kill the target cell, an apoptotic triggering protein or peptide, or any other anti-HIV protein or peptide.

With intrinsically low immunogenic properties, multiplexing ability and a small size, RNA based reagents such as shRNAs, miRNAs, ribozymes and RNA decoys are advantageous components for combinatorial therapy using anti-HIV vectors. Many RNA based reagents of the embodiments described herein target the HIV genes or the HIV genome by base-pairing to nucleic acids that can be attenuated by point mutation(s) in the target site. Additional RNA based reagents that are independent of base-pairing can be included in combinatorial therapy to enhance the anti-HIV gene therapy strategies described herein.

Anti-HIV agents that may be used in accordance with the embodiments described herein are often cytotoxic or cytostatic in nature. In some embodiments the anti-HIV agents that may be used as therapeutic agents in accordance with the embodiments of the disclosure include, but are not limited to non-nucleoside reverse transcriptase inhibitors, nucleoside reverse transcriptase inhibitors, protease inhibitors, fusion inhibitors, CCR5 antagonists/entry inhibitors, and integrase strand transfer inhibitors.

Toxins that may be used as therapeutic agents in accordance with the embodiments of the disclosure include, but are not limited to, ricin, abrin, ribonuclease (RNase), DNase I, Staphylococcal enterotoxin-A, pokeweed antiHIV protein, gelonin, diphtheria toxin, *Pseudomonas* exotoxin, and *Pseudomonas* endotoxin.

According to other embodiments, the aptamers described herein may be fused to one or more diagnostic agents (or "imaging agents"), forming a diagnostic aptamer fusion. The diagnostic aptamer fusion may to target and visualize HIV-infected cells in vivo via an imaging method (e.g., positron emission tomography (PET), computer assisted tomography (CAT), single photon emission computerized tomography, x-ray, fluoroscopy, and magnetic resonance imaging (MRI)). As such, the diagnostic aptamer fusion may be used in methods for diagnosing, monitoring and/or visualizing a disease related to infection with HIV.

In some embodiments, a diagnostic or imaging agent may include, but is not limited to a fluorescent, luminescent, or magnetic protein, peptide or derivatives thereof (e.g., genetically engineered variants). Fluorescent proteins that may be used include, but are not limited to, green fluorescent protein (GFP), enhanced GFP (EGFP), red, blue, yellow, cyan, and sapphire fluorescent proteins, and reef coral fluorescent protein. Luminescent proteins that may be used include, but are not limited to, luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9.sup.th edition, 2002; and The Handbook—A Guide to Fluorescent Probes and Labeling Technologies, Invitrogen, 10th edition, available at the Invitrogen web site; both of which are hereby incorporated by reference as if fully set forth herein).

Enzymes that may be used as an additional diagnostic agent in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

In other embodiments, the aptamers may be fused to both a therapeutic and a diagnostic agent. Therefore, any of the above diagnostic and therapeutic agents may be used in combination to form an aptamer fusion expressed by HIV-infected cells to deliver both a diagnostic and a therapeutic payload with a single dose.

RNA Compositions

According to some embodiments, RNA compositions are provided herein. The RNA composition may include an aptamer component, an shRNA component, an miRNA component, other components described herein, or a combination thereof. In some embodiments, the RNA compositions comprise one aptamer and either an shRNA component or an miRNA component. In other embodiments, the RNA compositions comprise more than one aptamer. For example, the RNA compositions may comprise two aptamers, three aptamers, four aptamers, five aptamers, 10 aptamers, 15 aptamers, 20 aptamers, or more than 20 aptamers. In these other embodiments, each aptamer may bind to a different target molecule, different locations on the same target molecule, or a combination thereof.

In some embodiments, the RNA compositions comprise one shRNA. In other embodiments, the RNA compositions comprise more than one shRNA. For example, the aptamer-shRNA fusions may comprise two shRNAs, three shRNAs, four shRNAs, five shRNAs, 10 shRNAs, 15 shRNAs, 20 shRNAs, or more than 20 shRNAs. In these other embodiments, each shRNA may target a different molecule, by DNA, mRNA, other polynucleic acids, or a combination thereof.

In some embodiments, the RNA compositions comprise one miRNA. In other embodiments, the RNA compositions comprise more than one miRNA. For example, the aptamer-miRNA fusions may comprise two miRNAs, three miRNAs, four miRNAs, five miRNAs, 10 miRNAs, 15 miRNAs, 20 miRNAs, or more than 20 miRNAs. In these other embodiments, each miRNA may target a different molecule, by DNA, mRNA, other polynucleic acids, or a combination thereof.

According to some embodiments, the RNA compositions may include one or more therapeutic agents described herein. In certain embodiments, the RNA compositions include one or more nucleic acid molecules described herein with reference to aptamers and aptamer fusions. The RNA compositions may target a protein and an mRNA, and components of the RNA compositions may be expressed intracellularly as part of a therapeutic or diagnostic payload. Similar to aptamers and fusions, RNA based reagents such as shRNAs, mRNAs, ribozymes and RNA decoys are advantageous components for combinatorial therapy using anti-HIV vectors. Additional anti-HIV agents that may be used in accordance with the embodiments described herein are often cytotoxic or cytostatic in nature, and/or, more generally, toxins may be used as therapeutic agents in accordance with the embodiments of the disclosure. According to other embodiments, the RNA compositions described herein may include one or more diagnostic agents described herein. In other embodiments, the RNA compositions may include both a therapeutic and a diagnostic agent. Therefore, any of the above diagnostic and therapeutic agents may be used in combination with RNA compositions expressed by, or delivered to, HIV-infected cells.

Therapeutic Uses of Aptamer Fusions and RNA Compositions

The RNA compositions, aptamers, aptamer fusions the aptamer-therapeutic agent fusions, the aptamer-imaging agent fusions, and combinations thereof described herein have at least a dual function that provides a basis for treating HIV. According to some embodiments, the aptamers may be used on their own to inhibit or suppress proliferation and survival of HIV-infected cells, and may also be used to eradicate existing HIV-infected cells. In accordance with the embodiments described herein, methods for suppressing HIV-infected cell proliferation, eradicating HIV-infected cells, and treating HIV are provided. HIV and HIV-infected cells that may be treated using the methods described herein include, acute infection, chronic HIV infection such as clinical latency, or AIDS (acquired immunodeficiency syndrome).

"Treating" or "treatment" of a condition, such as HIV, may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. For example, an aptamer or an aptamer fusion such as those described herein may be used to treat HIV, wherein the treatment refers to suppression of HIV-infected cell proliferation rate, an increase in HIV-infected cell death, or a decrease in HIV viral load. The treatments described herein may be used in any suitable subject, including a human subject or any mammalian or avian subject that needs treatment in accordance with the methods described herein (e.g., dogs, cats, horses, rabbits, mice, rats, pigs, cows).

The methods for treating HIV include administering a therapeutically effective amount of a therapeutic composition. An "effective amount," "therapeutically effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The therapeutic composition may include, among other things, an aptamer, a therapeutic agent, an aptamer-therapeutic agent, an aptamer-shRNA, an aptamer-miRNA, an imaging agent, an aptamer-shRNA-therapeutic agent, an aptamer-shRNA-imaging agent, an aptamer-miRNA-imaging agent, an aptamer-miRNA-therapeutic agent, or a combination thereof. Aptamers, shRNAs, miRNAs, therapeutic agents, imaging agents, aptamer-shRNAs, aptamer-miRNAs, aptamer-therapeutic agents, an aptamer-miRNA-imaging agents, an aptamer-miRNA-therapeutic agents, aptamer-shRNA-therapeutic agents, and aptamer-shRNA-imaging agents suitable for use according to the embodiments described herein may include, but are not limited to, those described above and in the Examples below. For example, in some embodiments, an RNA aptamer that may be used as part of the therapeutic composition may include a sequence illustrated in FIGS. 2B, and 3A-3K.

The therapeutic composition may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The therapeutic compositions described herein may also include one or more materials suitable for delivering gene therapy to the suitable subject. A suitable material for gene therapy may refer to any material useful for delivering gene therapy known in the art, but not limited to vectors (e.g., viral, bacterial, or a combination thereof), chemical transfection agents (e.g., calcium phosphate, lipid, or protein complexes. Calcium phosphate, DEAE-dextran, liposomes, and lipoplexes (for oral delivery of gene) surfactants and perfluro chemical liquids for aerosol delivery of gene), lipid vectors (e.g., vector and a lipid solution to form a liposome), physical transfection agents (e.g., agents useful with electroporation, microinjection, ballistic particles, micro-injections, aerosol, electroporation, gene guns, and/or a combination thereof), genetically modified cells, and/or a combination thereof.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, micro-injections, aerosol, electroporation, gene guns, subarachnoid, subcapsular, subcutaneous, transmucosal, transtracheal, and/or a combination thereof.

According to the embodiments described herein, the pharmaceutical composition may optionally include, in addition to the one or more aptamer or aptamer-shRNA fusions, one or more additional therapeutic agents, such as an anti-cancer agent, antibiotic, anti-HIV agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, beta.-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitors of DNA, RNA, or protein synthesis.

In addition to their independent function for treating HIV, aptamer-shRNA fusions may also serve as a HIV-infected cell specific delivery mechanism to deliver a therapeutic or diagnostic payload to a particular location with the HIV-infected cell, such as the cytoplasm. Therefore, according to some embodiments, methods for delivering a therapeutic payload (or a therapeutic agent) to the cytoplasm of an HIV-infected cell are provided. Such methods may include a step of expressing the aptamer-shRNA fusion and/or the aptamer-miRNA fusion in an HIV-infected cell, wherein the aptamer-shRNA and/or the aptamer-miRNA fusion comprises an aptamer component, such as an HIV-integrase aptamer, and a therapeutic agent component (i.e., the therapeutic payload), such as shRNA, miRNA, and/or other therapeutic agents described herein. As described above, the aptamer component may be any suitable aptamer, for example, a nucleic acid aptamer. In one embodiment, the nucleic acid aptamer is an RNA molecule expressed by an HIV-infected cell and that specifically binds a protein associated with HIV infection, such as HIV integrase, or other molecule, resulting in suppression or inhibition of viral replication.

In some embodiments, methods for treating a disease are provided. Such methods may include administering a therapeutically effective dose of a pharmaceutical composition to a subject suffering from a disease, wherein the pharmaceutical composition includes one or more aptamer-shRNA fusions and/or one or more aptamer-miRNA fusions as described in detail above, or other aptamers having different RNA molecules fused to an shRNA and/or an miRNA. The disease may be chronic HIV infection, chronic infectious disease affecting a particular cell type, or any genetic disease that is associated with a mutated, altered, missing, or overexpressed, gene or protein.

Cancers and tumor types that may be treated in accordance with the embodiments described herein include but are not limited to bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma (B cell and T cell) and leukemia, melanoma, ovarian cancer, pancreatic cancer, pituitary cancer, prostate cancer, rectal cancer, renal cancer, sarcoma, testicular cancer, thyroid cancer, and uterine cancer. In addition, the methods may be used to treat tumors that are malignant (e.g., cancers) or benign (e.g., hyperplasia, cyst, pseudocyst, hamartoma, and benign neoplasm).

Genetic disorders that may be treated in accordance with the embodiments described herein include, but are not limited to, muscular dystrophy, hemophilia, Huntington's disease, alpha-1 antitrypsin deficiency, Alzheimer's disease, various forms of breast cancer (e.g., BRCA1), cystic fibrosis, galactosemia, congenital hyperthyroidism, maple syrup urine disease, neurofibromatosis I, phenylketonuria, sickle cell disease, and Smith-Lemli-Opitz (SLO-RSH) syndrome, familial hypercholesterolemia, polycystic kidney disease, hereditary spherocytosis, Marfan syndrome, Tay-Sachs disease, mucopolysacchariddoses, and glycogen storage diseases.

Virus and virally-infected cells that may be treated in accordance with the embodiments described herein include, but are not limited to, hepatitis, papillomavirus, herpes simplex virus (HSV), cytomegalovirus (CMV), Epstein-Barr HIV (EBV), Smallpox HIV, and human or simian immunodeficiency HIV (HIV/SHIV).

In some embodiments, the pharmaceutical composition may also include a pharmaceutically acceptable carrier. A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The compositions and methods described herein may be used in combination with one or more additional treatment methods. In one embodiment, the aptamer-shRNA fusion and/or the aptamer-miRNA treatment may be combined with a treatment involving siRNA delivery. This way, one could effectively silence a mutated gene with an aptamer-siRNA fusion and inhibit activity of the expressed protein or peptide using an aptamer-shRNA described herein. In other embodiments, the aptamers may be used in combination with other HIV treatments, such as ART. In this way, one could prevent propagation of HIV in a patient using a multi-pronged approach which prevents activity of certain HIV proteins, and/or reduces and/or inhibits expression thereof.

Aptamers, such as nucleic acid aptamers, represent a new and potentially potent class of anti-HIV drugs. RNA aptamers are selected from random sequence pools of RNAs under conditions that provide highly specific, tight binding to targeted molecules. (Ramalingam, et al., 2011; Ditzler, et al., 2011). The low nanomolar binding affinities and binding specificity of aptamers to their targets have made them versatile tools for diagnostics, in vivo imaging, and therapeutics (Whatley, et al., 2013; Shum, Zhou and Rossi, 2013). It was previously demonstrated that an anti-HIV-1 gp120 aptamer can neutralize HIV-1 infection and is also capable of delivering anti-HIV siRNAs into HIV-1 infected cells (Duclair, et al., 2015; Zhou, et al., 2015). As described in the Examples below, the use of an HIV integrase aptamer and shRNA for intracellular trafficking of the aptamer is provided. This approach may be used in vivo to generate a therapeutic or prophylactic agent that, when administered, reduces or eliminates propagation of the HIV virus in infected cells.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. For example, although the Examples describe studies related to aptamer-shRNA fusions using aptamers to HIV integrase, once skilled in the art would understand that any aptamer may be fused to any applicable shRNA molecule and/or miRNA molecule based on the methods described below in order to bind to, reduce activity of, and/or target for degradation, a protein in a target cell. Non-limiting examples of aptamers, shRNA molecules, and miRNA molecules that may be used are described above. Further, all references cited in the disclosure are hereby incorporated by reference in their entirety, as if fully set forth herein.

EXAMPLES

Aptamers that are identified using systematic evolution of ligands by multi-tag exponential enrichment (SELEX) as an in vitro selection strategy can adopt complex structures to bind target proteins with high affinities and specificities, in particular, target proteins having low solubility and/or stability. As described above, aptamers may be selected to recognize a wide variety of targets from small molecules to proteins and nucleic acids in cultured cells and whole organisms (Ulrich et al. 2002; Wang et al. 2000; Blank et al. 2001; Daniels et al. 2003; Hicke et al. 2001; Wilson & Szostak 1999). The Examples below describes a cell-based multi-tag SELEX assay for the identification of HIV integrase binding aptamers, conjugation of these aptamers to shRNA, and the therapeutic delivery of these aptamer-shRNA fusions into cells.

In the Examples described below, a 2'-fluropyrimidine-RNA (2'F-RNA) combinatorial library was generated using a polymerase, rather than PCR, and a modified oligonucleotide library template. This combinatorial library was used to isolate RNA aptamers against two bacterially expressed and one mammalian expressed tagged integrase (IN) proteins (His-tag IN, MBP-tag IN, and FLAG-tag IN, respectively). The aptamers selectively bound to IN in the cytoplasm. Selected aptamers are candidates for use as aptamer-shRNA fusions and delivery for targeted inhibition of HIV integrase.

Example 1: Selection of Anti-Integrase Aptamer with Multi-Tag SELEX

Materials and Methods
Vectors:

To construct a maltose binding protein-integrase fusion (MBP-IN) expression vector (pJR166), an NdeI and Bam HI fragment containing the IN coding region was released from pEt-15b-IN (Jenkins, et al., 1996) and cloned into pMAL-c5X (NEB, New England Biolabs, Ispwich, Mass. 01938, USA). To generate a FLAG tagged IN mammalian expression vector, a human codon optimized integrase coding sequence was synthesized according to the amino acid sequence of p pEt-15b-IN and cloned into a pCDNA3 vector (Thermofisher, Grand Island, N.Y. 14072, USA) containing an N terminal 2×FLAG tag (pJR188).

Aptamer-shRNA Expression in Mammalian Cells:

For expression of shRNAs and aptamers in mammalian cells, a plasmid (pJR255) containing a U6 promoter for inducing expression of an shRNA, an aptamer, or an shRNA-aptamer fusion was constructed. The vector also contains a CMV promoter controlled mCherry visible marker. Two BbsI sites were inserted directly downstream of the U6 promoter to generate GTGG and TTTT overhangs upon cleavage. pJR255 was used to induce expression of shRNA and aptamers in HEK 293 cells and Ghost3 X4/R5 cells. Because CMV promoter-driven mCherry showed very weak signal in CEM cells, a similar plasmid (pJR288) was constructed that replaced the CMV promoter with the Ef1α promoter. For construction of various U6 driven shRNAs, aptamer or shRNA-aptamer fusion, 1 nmole each of oligonucleotide pairs containing CACC and AAAA overhangs (Table 1) was mixed in 1×T4 Ligase buffer (NEB), heated to 95° C. for 3 min, slowly cooled to room temperature, then ligated to BbsI cut of pJR255 or pJR288.

Production and Purification of Fusion Proteins:

HIS tagged HIV-1 Integrase (HIS-IN) expression vector was provided by Dr. Robert Craigie (NIDDK, NIH) (Jenkins, et al., 1996). E. coli strain C3016 bacterial cells (NEB, Ipswich, Mass. 01938, USA) were transformed with the HIS-IN plasmid. A single positive colony was picked to inoculate 250 ml of SOB medium containing 100 mg/ml of Ampicillin. The culture was grown overnight in 37° C. shaker (200 rpm). Induction was performed by mixing 250 ml of fresh SOB containing 2 mM IPTG and incubating another 3 hours at 22° C. HIS-IN was purified from bacterial cells with Ni-NTA agarose (Qiagen, Valencia, Calif., 91355, USA). using the manufacturer's protocol for protein purification in a native conformation. To increase the purity of the eluted protein, beads were washed first with buffer containing 300 mM NaCl and 50 mM Imidazole followed by a second wash with buffer containing 500 mM of NaCl and 30 mM imidazole. Eluted HIS-IN was dialyzed overnight at 4° C. with two changes of 500 ml PBS. Induction and lysis of MBP-IN follow a similar protocol. MBP-IN was purified with pMAL protein fusion and purification system (NEB, Ipswich, Mass. 01938, USA). Eluted fusion protein was dialyzed against 2 changes of 500 ml of PBS at 4° C. overnight. Purity and concentration of HIS-IN and MBP-IN fusion proteins was quantified by serial dilution and PAGE analysis using a BSA standard. FLAG tagged IN with associated cellular proteins complexes was isolated from HEK293 cells using the M2 anti-FLAG affinity gel according to the manufacturer's protocol (Sigma-Aldrich, St. Louis, Mo. 63178, USA).

Selection, Identification, and Structure Prediction of Aptamers using Multi-Tag SELEX (systemic evolution of ligands by exponential enrichment): The SELEX cycle was performed as described by Zhou et al with the following modifications. 2'F-RNA aptamers were selected from randomized sequences. A random library of RNA oligonucleotides which have a sequence of 5'-TAATACGACTCAC-TATAGGGAGGACGATGCGGGC-30N-GGTGGCGCGAGAGGTG-3' (SEQ ID NO:6) containing a 5' T7 promoter sequence, a 30N variable middle region and a 3' constant region was constructed by in vitro transcription of synthetic DNA templates with NTPs (2'F UTP, 2'F CTP, GTP, ATP, Epicentre Biotechnologies, Madison, Wis.). The library was generated from an oligonucleotide library that contained a 5' T7 promoter sequence, a 30N variable middle region and a 3' constant region (Table 1). 30N represents 30 nucleotide (nt) sequences formed by equimolar incorporation of A, G, C, and U at each position. T4 RNA polymerase was used to increase the complexity of the library. To increase the nuclease resistance, 2'F-Py RNAs were used. In addition, RT-PCR reactions were limited to 10 cycles of amplification. The RNA library was generated by Megashortscript T7 transcription kit (Thermofisher Scientific, Waltham, Mass., USA) using the gel purified RT-PCR product as a template. The selection rounds included two bacterially expressed IN proteins with His-tag and MBP-tag as well as a mammalian expressed FLAG-tag IN.

In each cycle of selection, RNA pools were folded in 200 µl of binding buffer (PBS pH7.4 plus 1 mM $CaCl_2$, 2.7 mM KCl, 2 mM $MgCl_2$) by heating to 95° C. for 3 min followed by slow cooling to 37° C. The folded RNA pools were then pre-cleared by incubating with HAWP filter (0.45 µm pore size, 13 mm diameter, EMD Millipore, Concord, Mass., USA) for 30 min. The tagged IN proteins were then incubated with the pre-cleared RNA pool in phosphate buffer (pH7.4) using progressively increased NaCl concentrations in SELEX cycles (50 mM in cycle 1-2, 100 mM in cycle 3-4, 147 mM in cycle 5 and up) and incubated for an additional 15 min at 37° C. In the first selection cycle, 1.5 nmol of RNA and 0.24 nmol of protein (RNA to protein ratio of 6.5:1) were used for binding reaction. As selection cycle progressed, protein concentration was gradually decreased to 0.12 nmol. Starting from cycle 3, an increasing amount of tRNA (20 µg in cycle 3-4, 40 µg in cycle 5-6, 80 µg in cycle 7 and up) was added as nonspecific competitor. The RNA-protein complexes were isolated by passing the reaction through a HAWP filter, followed by 1 ml washes with binding buffer. Membrane bound RNAs were eluted by 200 µl of elution buffer (7 M urea and 5 mM EDTA) at 95° C. for 5 min, followed by phenol/chloroform extraction. An additional round of selection was carried out with immunoprecipitated FLAG-IN complexes expressed from HEK293 cells. For selection by FLAG-IN, FLAG-IN complexes were purified from 1 mg of HEK293 cell lysate with 200 µl of M2 affinity gel beads. RT-PCR products of the final three cycles of selection and the sample binding to FLAG-IN complexes were subject to high throughput deep sequencing (Illumina). Sequence analysis was performed as described. Secondary structure predictions of aptamers were predicted using MFOLD (Zuker 2003), available at http://www.bioinfo.rpi.edu/applications/mfold/ using a salt correction algorithm and temperature correction for 25° C.

Results and Discussion

Selection of Anti-Integrase Aptamer with Multi-Tag SELEX:

The anti-integrase aptamer that targets the integration step was selected to be used with combinatorial therapy to treat HIV patients. SELEX was used to isolate RNA aptamers that bind to HIV integrase (IN). A bacterially expressed HIS-tagged mutant integrase (F185K/C280-S) that retains DNA integration activity but has much improved solubility (Jenkins, et al., 1996) was used for aptamers library enrichment. Salt concentrations of less than 147 mM of sodium chloride was used for the enrichment process because the aptamers will eventually be expressed in T cells for anti-HIV gene therapy when administered to patients. At this salt concentration, the integrase protein becomes poorly soluble and very unstable especially when the tag was removed from the expressed fusion (data not shown and FIGS. 1A and 1B, and data not shown). Therefore, the HIS-tagged fusion protein was used for enrichment.

To minimize the enrichment of aptamers that bind to HIS-tag rather than integrase two additional tagged integrase fusions were used for aptamer selections. First, an MBP-tagged IN (MBP-IN) was expressed in E. coli. Second, a FLAG-tagged IN (FLAG-IN) was expressed in human cells in a physiologically relevant environment. Integrase interacts with a number of cellular proteins (Cherepanov, et al., 2003; Llano, et al., 2006; Zheng, et al., 2011). FLAG-IN that complexed with cellular proteins presents a more native conformation that should facilitate the isolation of functional aptamers.

Figure 1C:
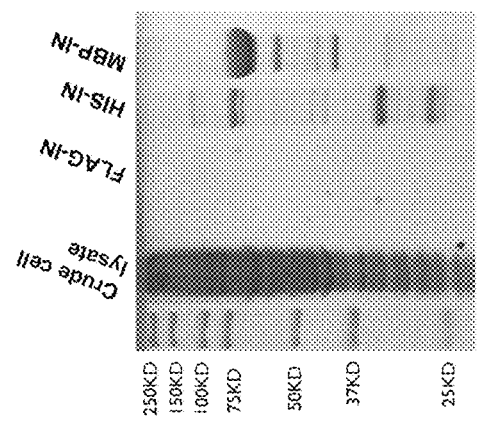
Figure 1A:
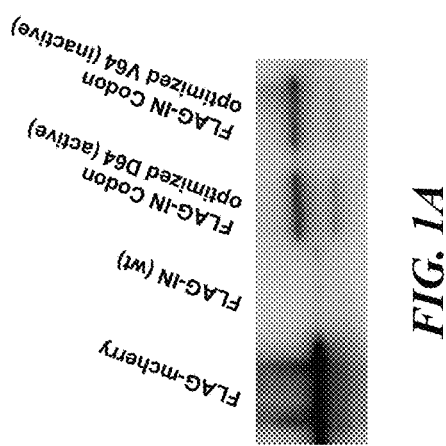
Figure 1E:
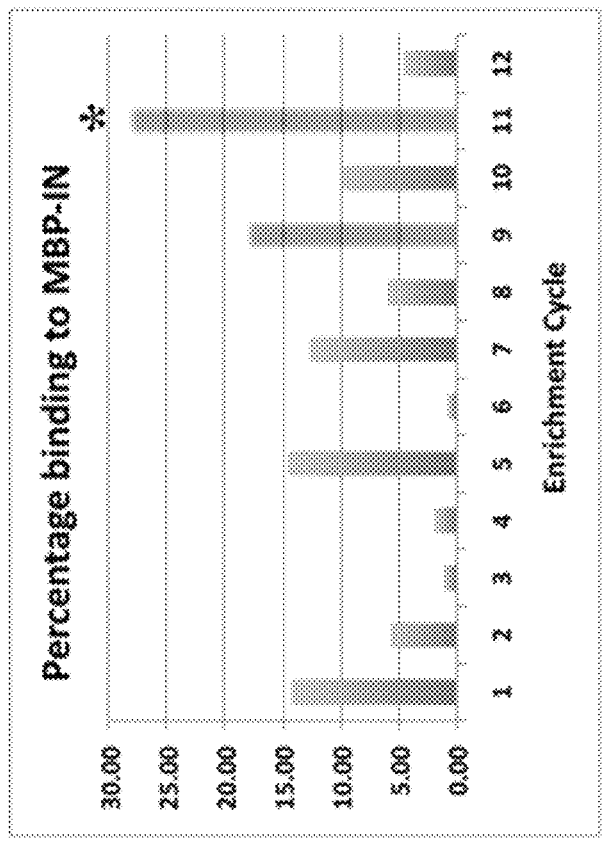
Figure 1D:
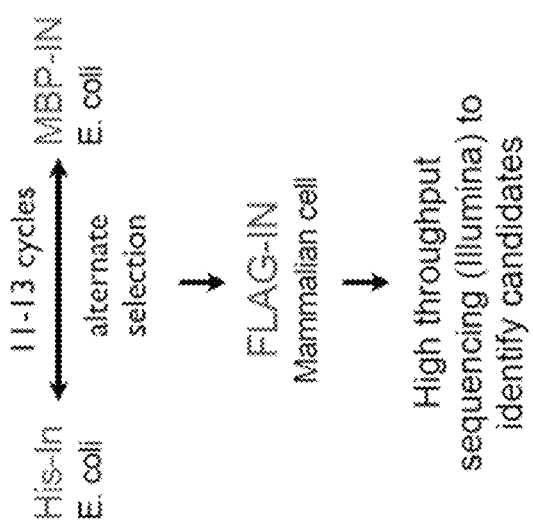
Figure 10:
FIG. 10 illustrates plasmids used in functional test of expressed aptamers according to some embodiments. Both pJR255 and pJR288 contain a U6 promoter to drive the expression of aptamers, shRNAs, or shRNA-aptamer fusions. Oligonucleotide pairs with CACC and AAAA overhangs were cloned to Bbs-1 cut sites. Vectors contain a Neomycin (G418) resistance cassette and a mCherry visible marker induced by either CMV (pJR255) or EF1a-HTLV (pJR288) promoter.

Consistent with previous reports, wild-type Integrase had low expression levels in mammalian cells (Cherepanov, et al., 2000). To increase expression, the wild-type integrase was codon optimized and expression in mammalian cells increased by more than 10-fold in yield of the protein (FIG. 1A). An inactive mutant D64V of the codon optimized integrase was generated since over-expression of the active integrase could be toxic to cells. Similar yields for both active and inactive forms were obtained from transient expression in cells (FIG. 1A). Accordingly, the transiently expressed active form was used for enrichment. A high proportion (74%) of active FLAG-IN was purified from transfected HEK 293 cells (FIG. 1B). However, the yield was insufficient to allow the use of purified complexes in the early selection cycles that typically requires 10 to 20 µg of purified protein (FIG. 1C). Therefore, bacteria expressed HIS-IN and MBP-IN (FIGS. 10A and 10B) was used alternately in the early selection cycles while FLAG-IN complexes purified from human cells were reserved for the final round of selection (FIG. 1D). Enrichment of the library was monitored by an increase in the percentage of binding to MBP-IN (FIG. 1E). Samples from cycles just reaching the plateau (typically cycle 11 to 13) were subjected to an additional cycle of enrichment using the cellular complexes that co-immunoprecipitated with FLAG-IN (FIG. 1E). Samples of the final four cycles of selection were subjected to high throughput sequencing (Illumina). Four independent selections were performed (S1-S4). Selection 2 did not yield any candidate aptamers that were substantially enriched and was rejected.

Figure 2A:
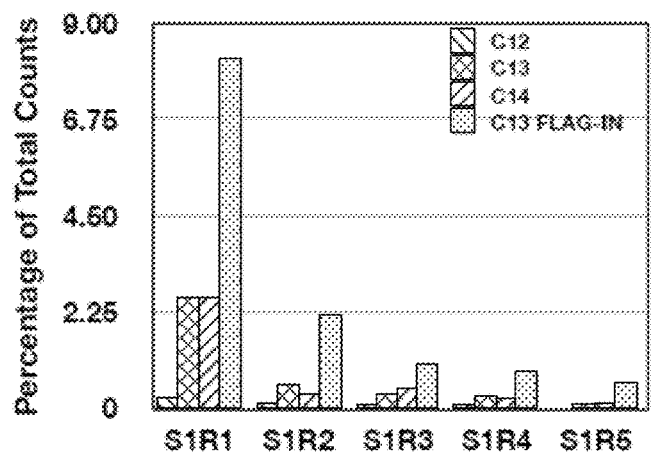
FIGS. 2A and B illustrate that similar aptamers were isolated in three independent selections according to some embodiments. (A) Change of abundance of aptamers during the last 4 cycles of enrichment. In some embodiments, FLAG-IN further enriched the aptamer. In addition, one aptamer (S1R1, S3R2, and S4R1 with identical sequence) dominated in all three selections. A steeper slope of increasing stringency was used for selection 3 (S3) and S4 cycles with the plateau reached at cycle 11, two cycles earlier than S1. (B) Alignment of the 15 most abundant aptamers. Sequences of the variable region of the aptamers are shown. Aptamers having identical sequences are highlighted (red or blue) and the single base difference between S1R1 and S3R5 (red T and blue G) are shown.
Figure 2A:
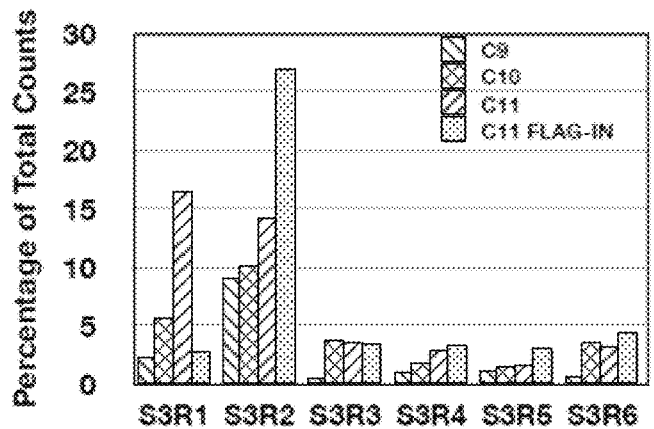
Figure 2A:
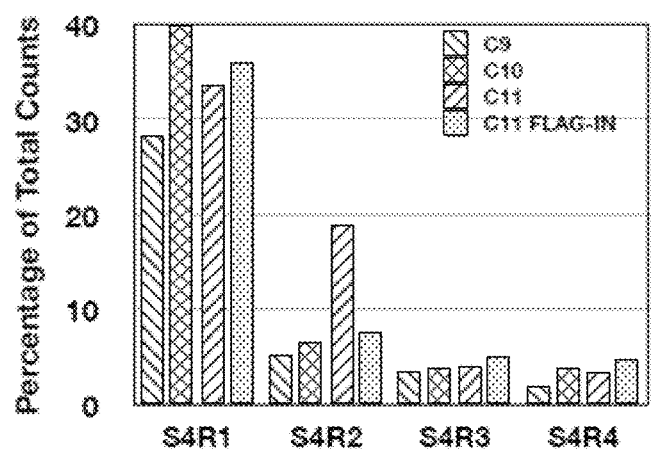
Figures 3G, 3H, 3I:
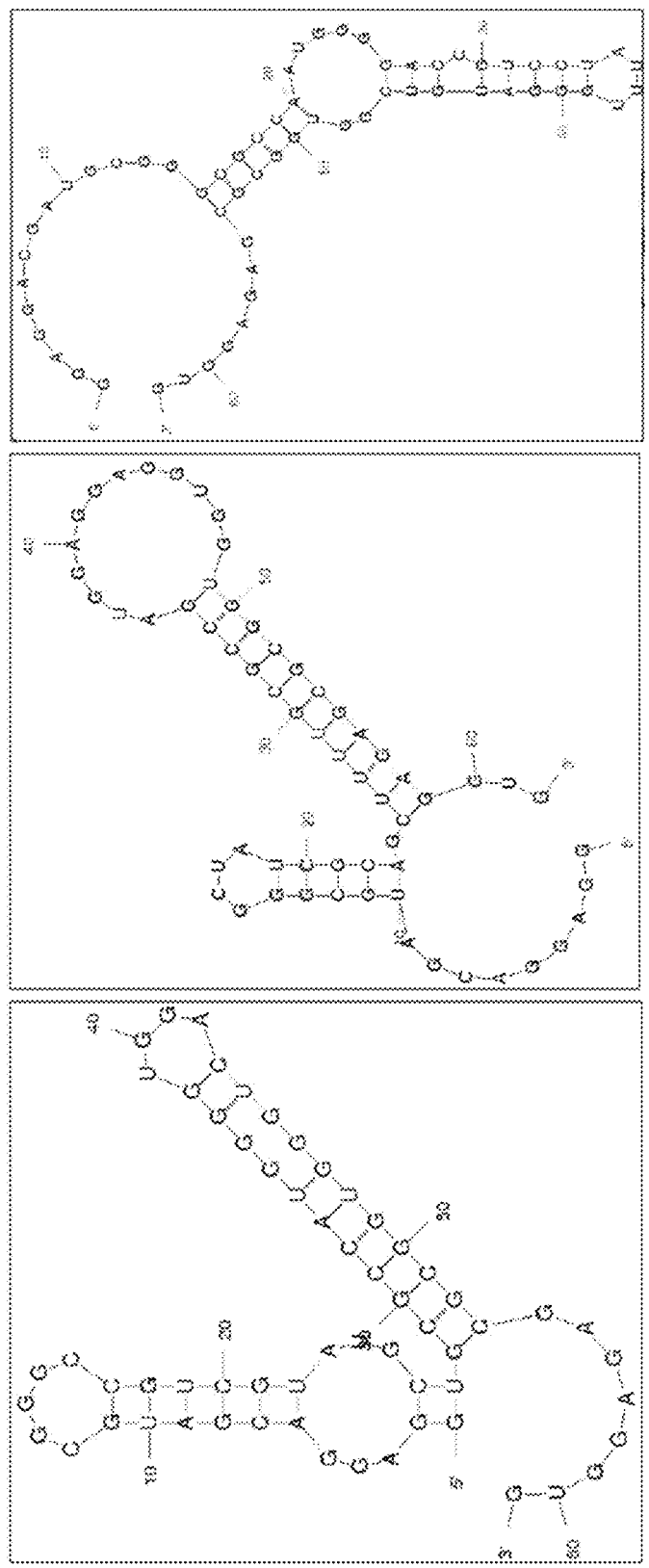

The most abundant aptamer isolated from first selection was designated as S1R1 (Selection 1, aptameR 1). The sequence of S1R1 is identical to that of S3R2 and S4R1. This aptamer is the most abundant that represented 8.1%, 26.6% and 35.7% of total reads in three independent selections S1, S3 and S4 respectively (FIGS. 2A and 2B). In addition, aptamers S3R5 and S4R4 differed from S1R1 by only one base and shared the same predicted secondary structure (FIG. 2B and FIG. 3A). Moreover, aptamers S1R2, S1R3, S1R4, S1R5 and S4R3 also share similar predicted secondary structures as S1R1, having two stem-loops separated by 4 to 10 single stranded spacer nucleotides (FIGS. 3, B, C, D, E, and K). Overall, aptamers with the predicted two stem-loop structure represented the majority of aptamers isolated, suggesting that aptamers with these structures might have high affinity to an exposed domain of Integrase.

As explained above, the multi-tag SELEX method was developed to select and stably express RNA aptamers against the HIV integrase and reverse transcriptase. By incorporating the aptamers as the terminal loop of a shRNA, long-term inhibition of HIV replication in a cell culture system was achieved. The SELEX method has been useful for isolating RNA aptamers against specific protein targets. Typically, aptamers with high binding affinity are selected by binding to a single soluble protein. Applying this approach to unstable or low solubility proteins such as the HIV integrase has been technically challenging. Contrary to current SELEX, multi-tag SELEX includes selecting aptamers using multiple tagged proteins in alternate cycles. Tags such as MBP, HIS and FLAG can improve solubility and/or stability of the tagged proteins and thus facilitate purification and selection. Varying the capture method is a longstanding approach to reduce background. Multiple tagged proteins were used in alternate selection cycles in a modified SELEX protocol, we termed multi-tag SELEX. This method allows the selection of aptamers against low solubility or unstable proteins while minimize non-specific binding to the tags. In most cases, target proteins expressed in mammalian cells is preferable over bacterially expressed ones. HIV integrase undergoes various post-translational modifications such as phosphorylation, acetylation and sumoylation in mammalian cells (45). This increases the likelihood of obtaining functional aptamers against modified IN protein. Furthermore, the integrase should be in its native conformation and therefore, be more likely to form complexes with other cellular proteins. This increases the chance of obtaining aptamers against IN protein epitopes available in host cells. (Zheng and Yao, 2013). Ideally, selection should be alternated among all three tagged proteins. However, the limited yield of FLAG-IN restricted the use of FLAG-tagged Integrase to only one selection cycle. Nevertheless, using multi-tag SELEX, RNA aptamers that target HIV integrase under physiological salt concentration were isolated. This strategy should see general applications for other difficult and specific targets, such as a functional domain of a protein that may have low solubility. This method also allows selection of more physiological relevant aptamers.

Example 2: Functional Assay for Integrase Binding Aptamers

Materials and Methods

Vectors:

The vectors used in this Example were designed and produced as described above with reference to Example 1.

Gel Mobility Shift, Binding Assay, and Northern Analysis:

A binding assay to assess library enrichment was carried out as follows. 5 µg of aptamer RNAs from each cycle were first treated with Antarctic Phosphatase (NEB), followed by phenol extraction and ethanol precipitation. Dephosphorylated RNA pellets were resuspended in PBS and their concentrations were determined by nanodrop spectrometer. 10 pmol of aptamer RNA was end labeled with $^{32}$P ATP, adjusted to a concentration of 200 nM with PBS, and purified using a G25 column (GE Life Sciences). Half of the $^{32}$P labeled aptamer RNA was folded by heating (95° C. for 3 min) and slow cooling (37° C. on heat block). 1 pmol of folded RNA was incubated with 10 pmol of MBP tagged Integrase and 10 pmol of tRNA at 37° C. for 20 min. The reactions were passed through nitrocellulose filters (0.45 μm pore size, 13 mm diameter, EMD Millipore, Concord, Mass., USA) which were then washed with 1 ml PBS. Radioactivity of filters containing aptamer-protein complexes was determined by scintillation counter using 1 pmole of labeled RNA as standard.

The gel mobility shift assay was carried out as described (Zhou, et al, 2009). RNA aptamers were transcribed from annealed oligonucleotide pairs (Table 1) containing T7 promoter sequences using Megashortscript T7 transcription kit (Thermofisher Scientific, Waltham, Mass., USA). Percentage binding was determined by Image J (http://imagej.nih.gov/ij/index.html). $^{32}$P labeled and folded aptamers (final concentration of 2 nM) were incubated with HIS-IN protein (final concentration of 0, 20, 40, 80, 160 and 320 nM) at 37° C. for 30 min. The complexes were then separated by 5% native polyacrylamide gel. Autoradiographs were acquired via Typhoon phosphorimaging system (GE Healtcare Life Science, Pittsburgh Pa. 15264, USA). Digital images were imported and analyzed by ImageJ software (http://image-j.nih.gov/ij/index.html). 50 percent binding values were determined by the Prism 6 software (GraphPad Software Inc) using non-linear curve regression. Northern analysis of total or fractionated RNAs was carried out as described (Castanott, et al., 2009) using probes listed in primer list (Table 1). Quantification of relative band intensity was measured and calculated using Image J software.

Results and Discussion

Figure 11A:
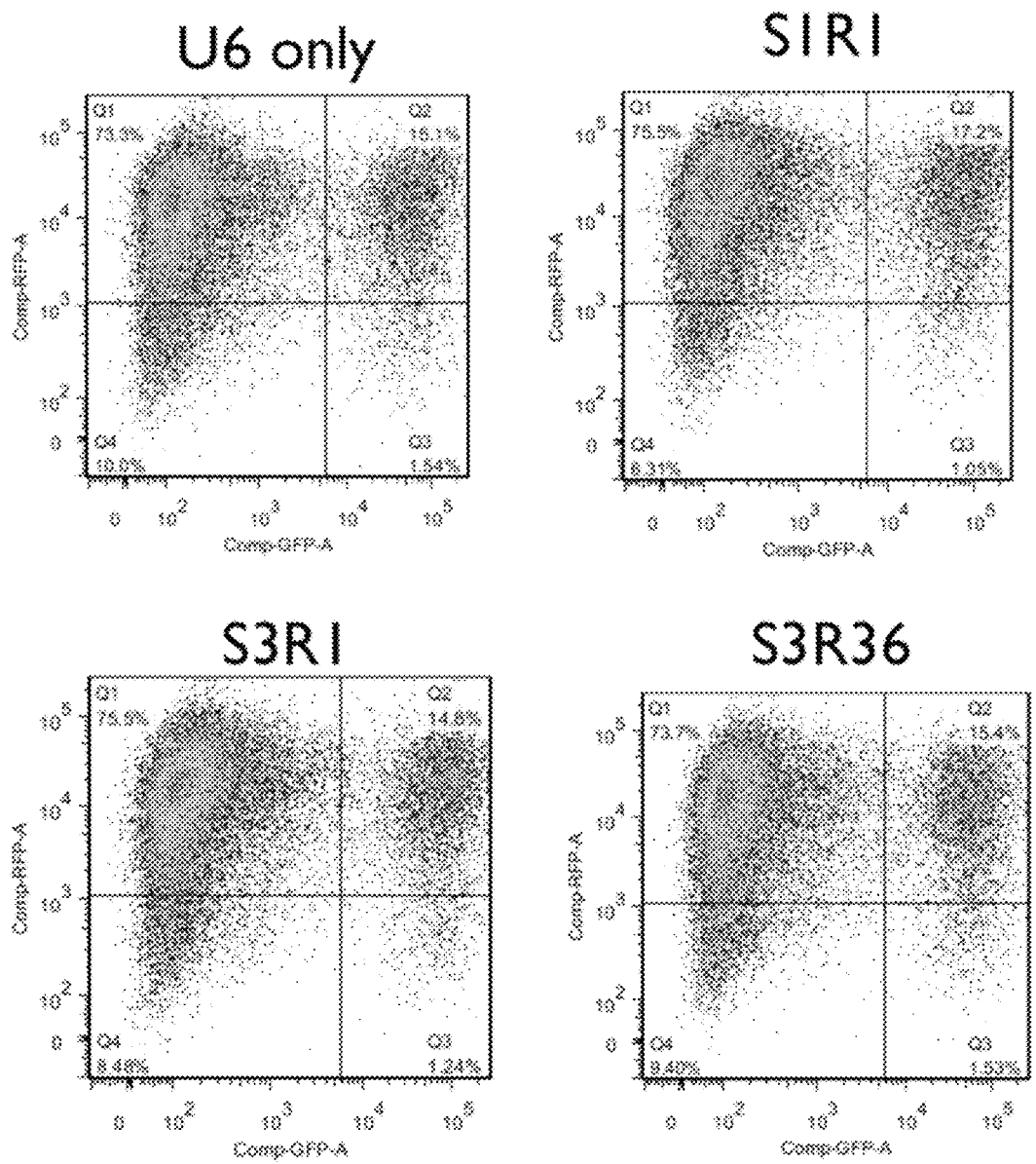
FIGS. 11A-11C illustrate that aptamers expressed from the U6 promoter showed no inhibition in single cycle infection by lentivirus HIV7-GFP according to some embodiments. (A) FACS data gated with mCherry and GFP signals are shown. (B) Quantification of FACS data. The percentage of double positive (Q2) over the total GFP positive (Q2+Q3) was compared to the U6 only control (100%). (C) Another quantification of FACS analysis. All three shLuc-Aptamer fusions exhibited moderate but consistent inhibition of lentiviral integration.
Figure 11B:
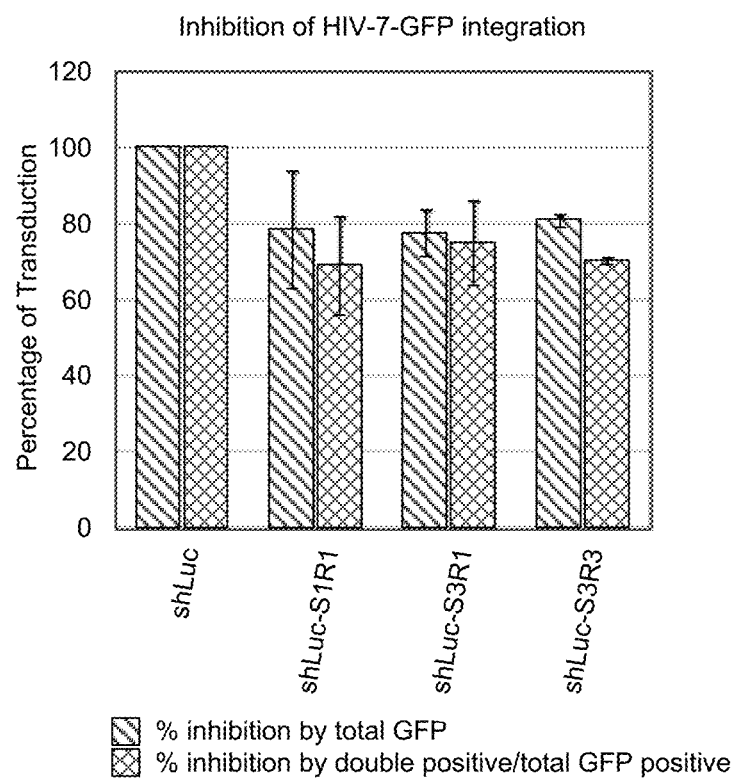
Figure 11C:
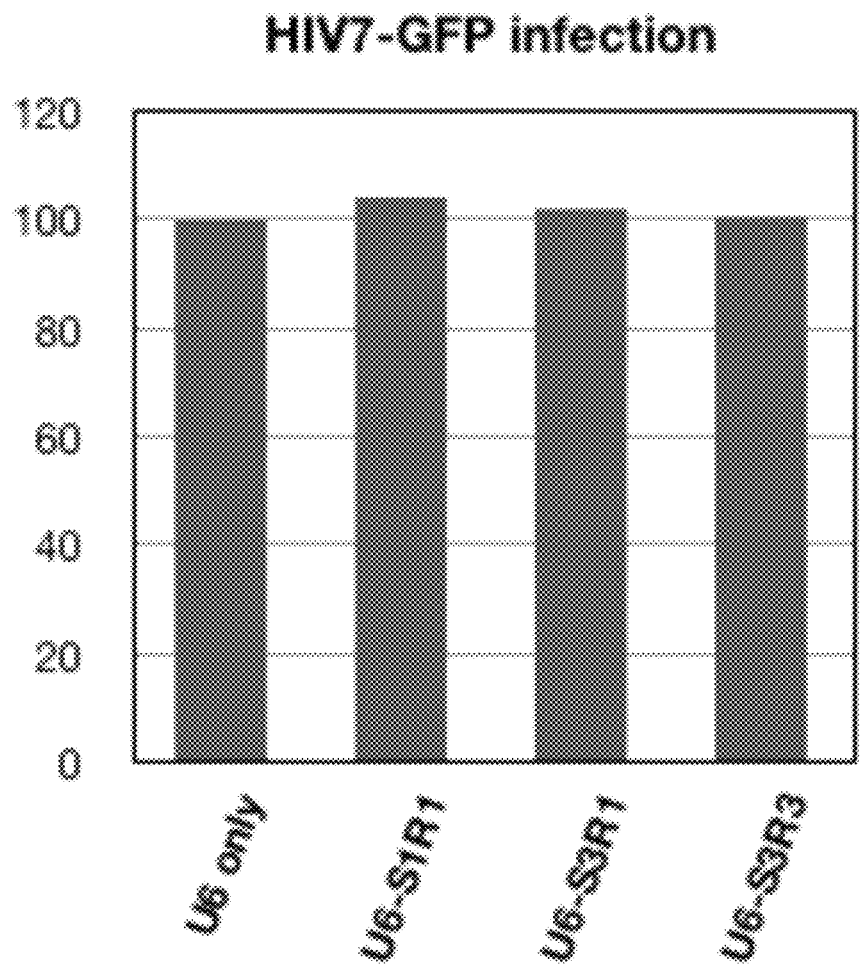
Figure 12B:
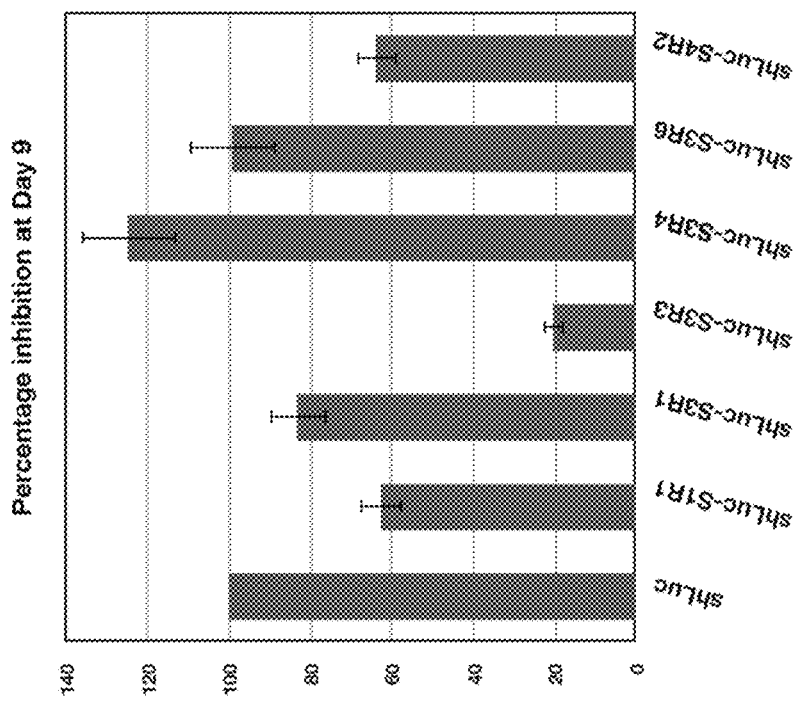
FIGS. 12A and 12B illustrate a comparison of efficacy of other aptamers in multi-cycle infection according to some embodiments. Ghost3 cells expressing shLuc-aptamer fusions were infected with Ba-L virus. P24 levels were monitored for 9 days. (A) Change of virus concentration in cultures measured by P24 assay. Data of single representative assay with average of triplicate samples is shown. Error bar is not shown because of extensive overlapping. (B) Inhibition of HIV replication at Day 9 post-infection. Average and standard deviation of two independent assays are shown.
Figure 12A:
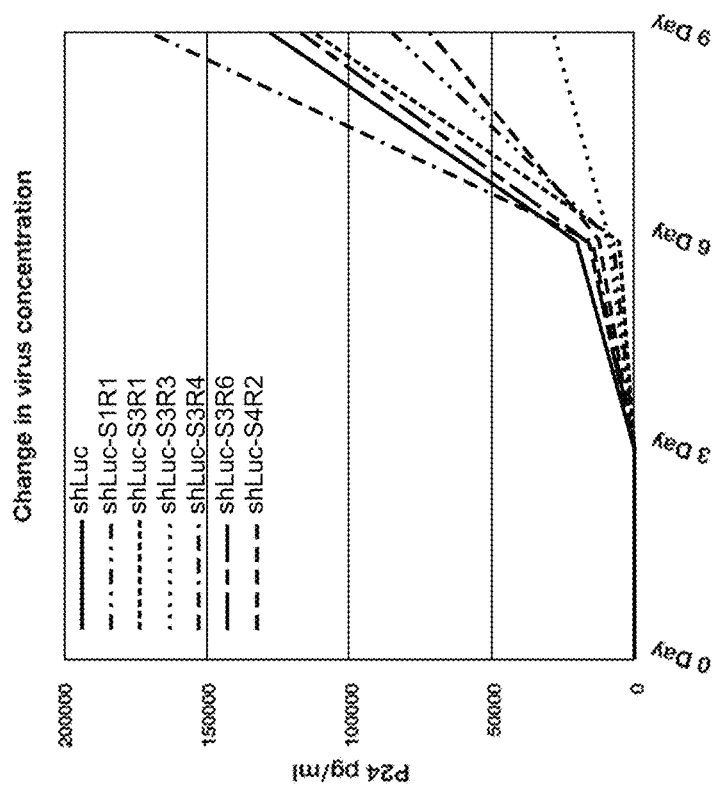
Figure 13:
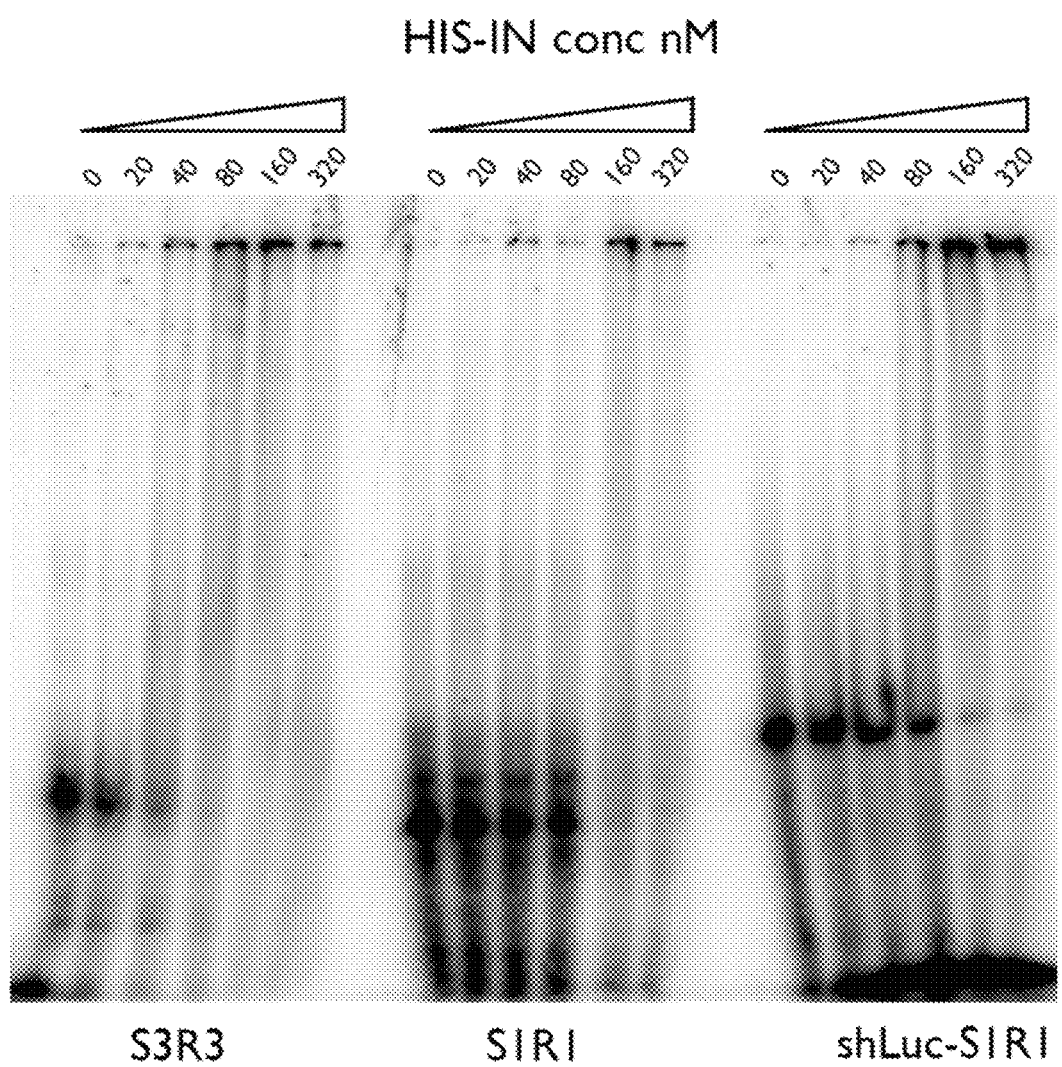
FIG. 13 illustrates that the S3R3 aptamer had higher binding affinity to HIS-IN than S1R1 even though S1R1 was more abundant in the final rounds of selection according to some embodiments. A single gel shift experiment is shown. The number in the text is the average of two independent experiments.

A direct functional assay was used to test the inhibitory effect of the aptamer candidates for combinational gene therapy in T cells or hematopoietic stem cells (HSC). To this end, plasmids (pJR255) consisting of: 1) a U6 promoter for inducing the expression of the aptamers, 2) a G418 resistant cassette for selection, and 3) an mCherry marker for cell purification and functional analysis were generated. (FIG. 11). RNAs expressed from U6 (pol III) promoter lack nucleus export signals and stay in the nucleus (18,19,20,21). Integrase functions primarily in the nucleus. These nuclear aptamers may be effective against its functions The aptamers with a distinct secondary structure, S1R1, S3R1 and S3R3, were tested for resistance to infection with the self-inactivating (Sin) lentiHIV vector (HIV-7-GFP) (Yam, et al., 2002). Stable HEK293 lines were established by transfecting an empty plasmid backbone (negative control) or plasmids that expressing S1R1, S3R1 or S3R3, selected for G418 resistance and sorted for mCherry positive signals. Each population of cells was transduced with lentiHIV particles at an MOI of 0.3. The transduced cells were analyzed by FACS 10 days after transduction to minimize the effects of GFP from nonintegrated viral DNA. If an aptamer exerts any inhibition of HIV integrase, the percentage of GFP and mCherry double-positive cells should be reduced compared to the control. By this measure, FACS data showed that all three aptamers expressed directly from the U6 promoter did not inhibit HIV-7GFP integration (FIG. 12).

Example 3: Incorporation of Aptamers Into shRNA Loops Aids Cytoplasmic Export

Materials and Methods
Vectors:
The vectors used in this Example were designed and produced as described above with reference to Example 1.
Luciferase Assay:
A HEK293 cell clone stably expressing firefly luciferase was transfected with the plasmids expressing the shLuc or the shLuc-aptamer fusions. Cells were harvested two or three days post-transfection and their firefly luciferase activities were determined by the Luciferase Assay System (Promega, Madison, Wis., USA).
Gel Mobility Shift, Binding Assay, and Northern Analysis:
The shift and assays were performed as described above with reference to Example 2.

Results and Discussion

As mentioned above, pre-miRNAs are exported to the cytoplasm by Exportin 5 that recognize the 3' two base overhangs of the stem-loop structures (Okada, et al., 2009; Lee, et al., 2011). Some pre-miRNAs contain a large loop; however, these pre-miRNAs are still efficiently exported to the cytoplasm, cleaved by Dicer and loaded into RNA Induced Silencing Complex (RISC) and they silence their target mRNAs (Feng, et al., 2012; Winter, et al., 2013).

Figure 4A:
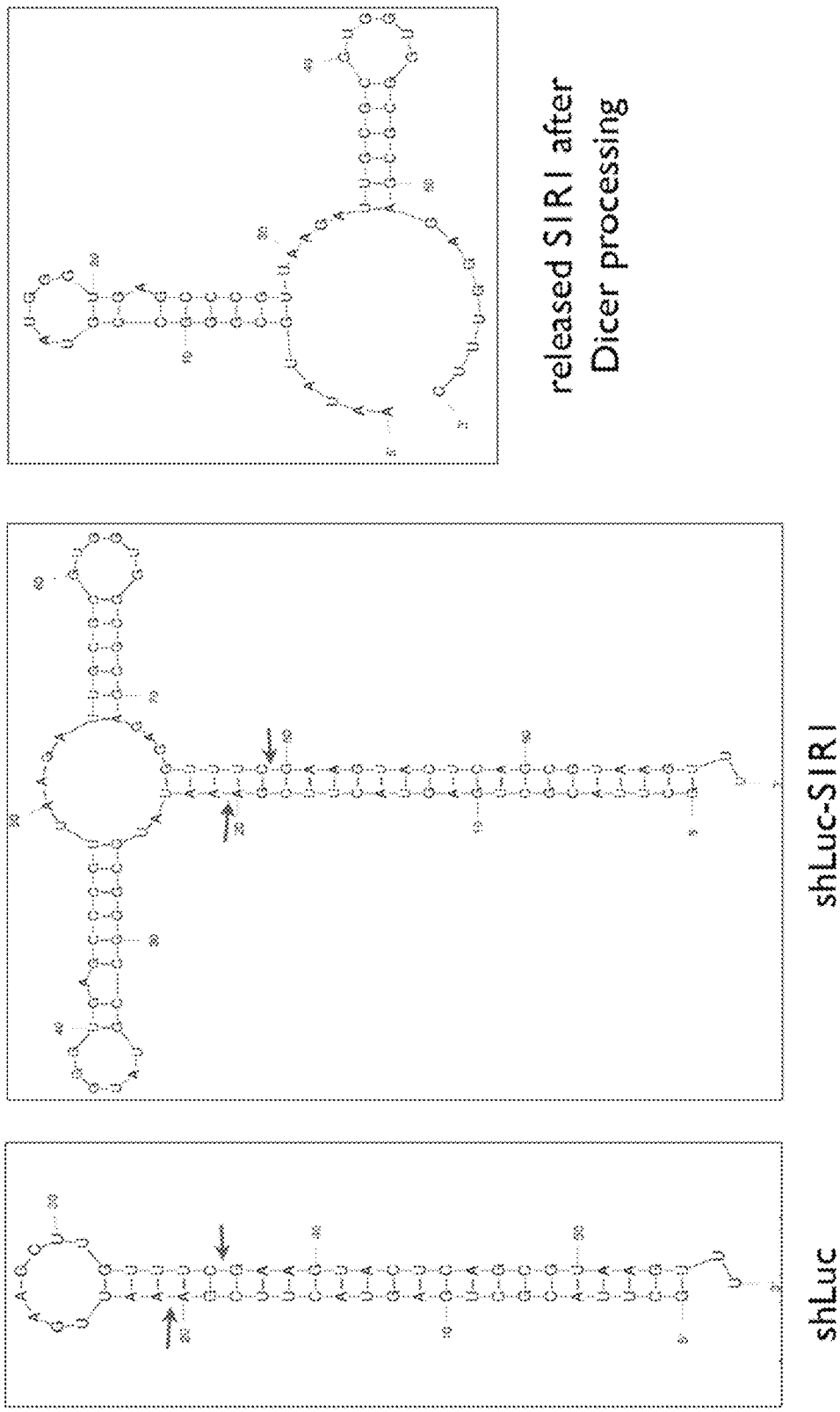
FIGS. 4A-4D illustrate that an shRNA-aptamer fusion can inhibit expression of a target gene according to some embodiments. (A) Predicted secondary structures of shLuc, shLuc-S1R1 and the released S1R1. Secondary structures were predicted by M-fold (18). Potential Dicer cleavage sites are marked by arrows. (B) Percentage inhibition of firefly luciferase expression by shNS (NonSpecific), shLuc and shLuc-S1R1 fusion at Day 2 or Day 3 after transfection. Average and standard deviation of three independent experiments. (C) Inhibit of other shLuc-aptamer fusions at Day 3 after transfection. Average and standard deviation of two independent experiments. (D) Northern blot showing processing, distribution and stability of shLuc and shLuc-S1R1 fusion. Probes are listed to the right of the panels. RNAs and their corresponding sizes were listed on the left of the panels. Box at top panel highlights mature siRNA against luciferase. tRNA and U6 RNA were used as quality control for fractionation.
Figure 4C:
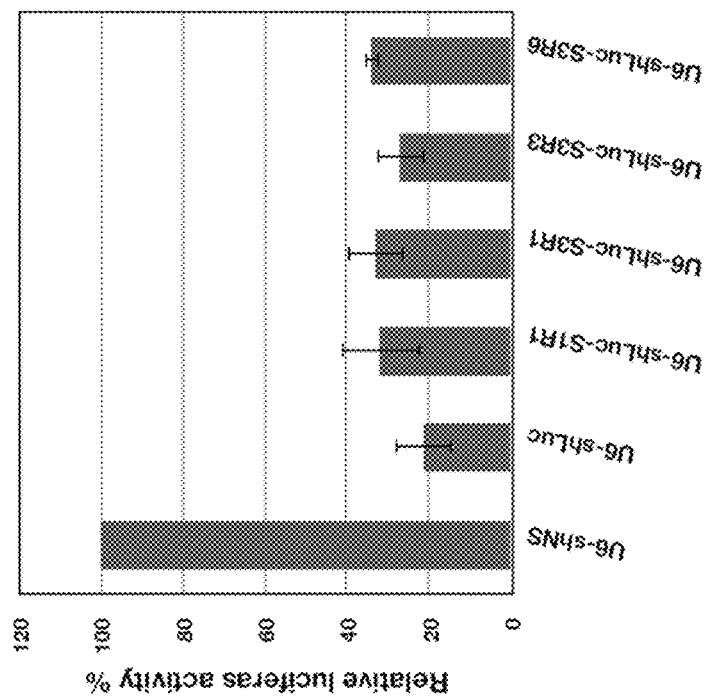
Figure 4B:
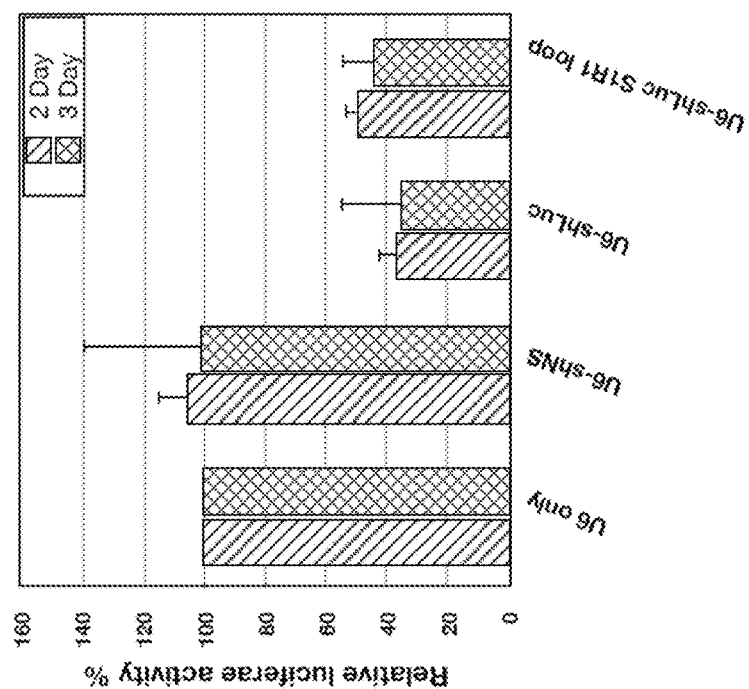
Figure 4D:
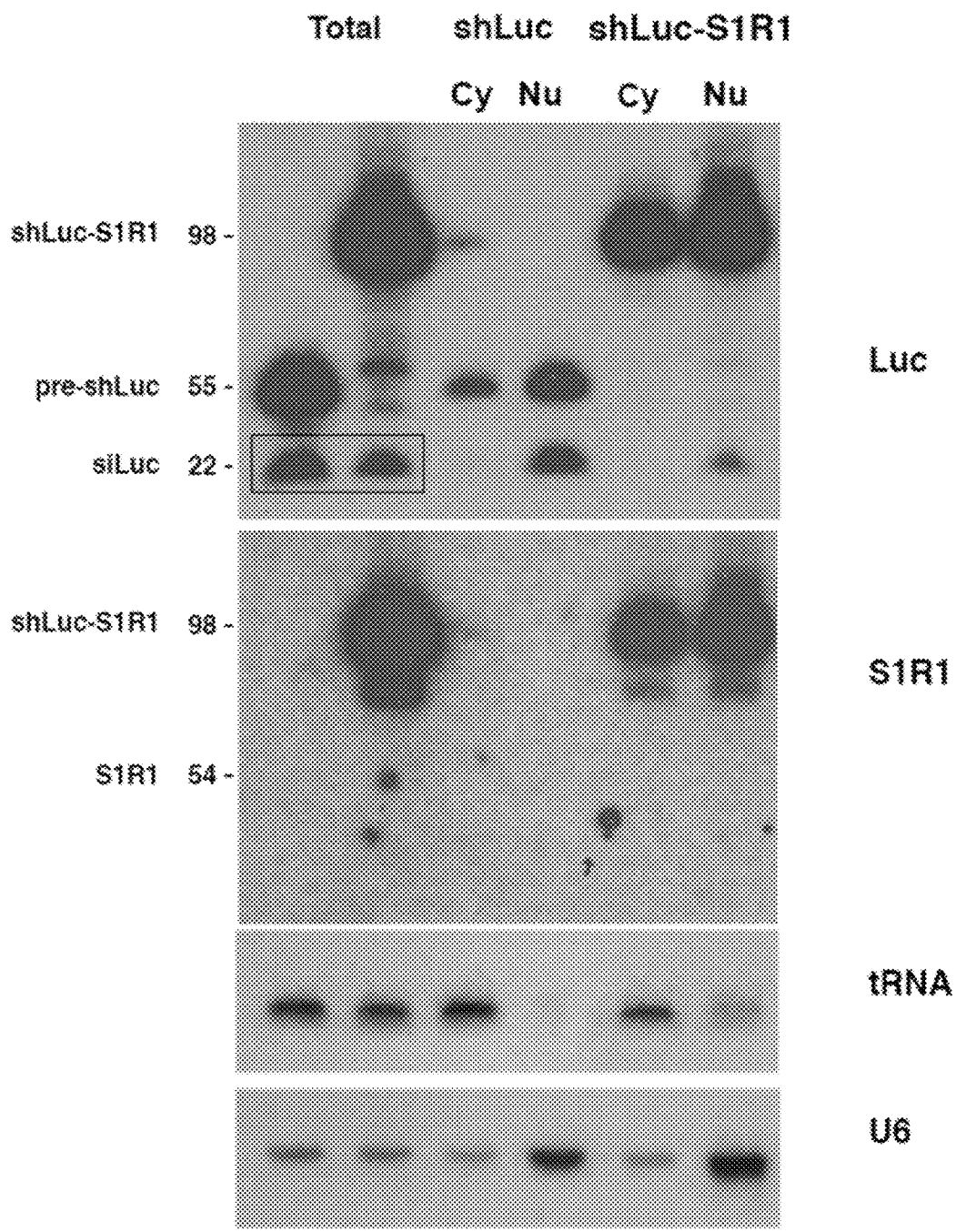

Using a luciferase assay, export of the shRNA-aptamer fusion into the cytoplasm was tested. A HEK293 clone that stably expressed a firefly luciferase gene was transfected with constructs containing 1) U6 promoter only, 2) U6 promoter inducing a nonspecific shRNA (shNS), 3) U6 promoter inducing shRNA targeting luciferase with an artificial 10 bases loop (shLuc) (Li and Rossi, 2005) and 4) shLuc with the aptamer S1R1 as the loop (shLuc-S1R1) (FIG. 4A). The shLuc-S1R1 showed substantial inhibit of luciferase activity. The shLuc with the 10 base loop was slightly stronger at inhibit of luciferase activity. (FIG. 4B). Similar results were observed in shLuc incorporated with other aptamers S3R1, S3R3 and S3R6 (FIG. 4C). These results indicated that the shLuc-aptamer fusions like a canonical shRNA that could be processed by Dicer to release the siLuc RNA, resulting in knockdown of the luciferase target. Northern blot analyses on fractionated samples were performed to further assess the distribution and processing of the shLuc-aptamer fusion. When detecting the luciferase guide strand, both shLuc and shLuc-S1R1 showed similar steady state levels (FIG. 4D, top panel). Moreover, both shLuc and shLuc-S1R1 showed similar distributions between the nucleus and the cytoplasm, indicating that the large S1R1 loop neither destabilized the shRNA-aptamer fusion nor hindered nuclear export.

Consistent with the observed 20% weaker inhibit of luciferase activity, 25% less processed siRNA was detected from shLuc-S1R1 than from shLuc (FIG. 4D top panel box), indicating that the large S1R1 loop moderately inhibited Dicer processing. The same blot was probed with a S1R1 probe to further determine the fate of the aptamer S1R1 released from the shLuc-S1R1 fusion. When detected by the S1R1 probe, the shLuc-S1R1 fusion was distributed in both the nucleus and the cytoplasm, similar to that detected by the luciferase probe. However, the released S1R1 aptamer was not detectable by the S1R1 probe (FIG. 4D middle panel), suggesting that the S1R1 aptamer released by Dicer processing was rapidly degraded, similar to the terminal loops and the passenger strand of miRNAs. These results showed that aptamers incorporated into the loop of an shRNA could be exported to the cytoplasm and the shRNA-aptamer fusion but not the released aptamer could be maintained at a high steady state level. In contrast, the released aptamer did not accumulate to detectable levels.

Another challenge for using aptamers in anti-HIV gene therapy is the lack of sustained expression of the therapeutic genes, especially in the cytoplasm of host cells where multiple steps of the HIV replication cycle occur. Currently, most nucleic acid aptamers are administered extracellularly to block interaction of surface receptor and HIV proteins. Some aptamers can be internalized together with the receptors. However, this method allows certain levels of delivery and may be subject to cyclical variation. A sustained high level of RNA aptamer can be achieved by Pol III promoter driven expression. However, without an intrinsic nuclear export signal, Pol III transcripts stay in the nucleus thereby limiting their application for targeting nuclear proteins such as transcription factors (Lee, et al., 2008).

By incorporating the aptamer into the terminal loop of an shRNA, the U6 promoter driven shRNA-aptamer fusions persisted at a high level in the nucleus and the cytoplasm. A portion of the fusion is processed by Dicer, resulting in knockdown of target genes. We could not detect the released aptamer moiety in a Northern blot assay, consistent with the rapid degradation of uncapped and unprotected RNA in the cytoplasm. However, the shRNA-aptamer fusions targeting either IN or RT exhibited a stronger inhibition than the aptamer alone. The mechanism of this enhancement is not clear. In principle, several factors or a combination of them could contribute to a stronger inhibition. The shRNAs facilitated the export of the fusions to the cytoplasm where newly translated viral polyproteins might be more susceptible to aptamer binding. The stronger inhibition observed in multiple infection cycle than in single infection cycle suggested that this might be one of the mechanisms. The stem structure of an shRNA is very stable. It could have stabilized the active aptamer structures and/or increased the steady-state levels of the primary transcript. Importantly, the integrase aptamer S3R3 showed a strong synergy with an shRNA targeting the tat-rev region and together the shS1-S3R3 fusion exhibited a very strong and prolonged inhibition of HIV replication in-cell cultures.

Example 4: shRNA-aptamer Fusions Effectively Inhibit Lentivirus Integration

Materials and Methods
Vectors:
The vectors used in this Example were designed and produced as described above with reference to Example 1.
HIV Challenge Methods and Associated In Vitro Cell Culture:
Ghost 3+CXCR4+CCR5 cells, HIV NL4-3 and Ba-L strains were obtained from the NIH AIDS Reagent Program. Ghost cells and HEK293 cells (ATCC CRL-1573) were grown on DMEM supplemented with 10% FBS and 1 mM Glutamine. CCRF-CEM (ATCC CRM-CCL-119) cells were grown in RPMI supplemented with 10% FBS and 1 mM Glutamine. HEK293 and Ghost cells were transfected with Lipofectamine 2000 according to the manufacturer's protocol (ThermoFisher, Waltham, Mass., USA). To generate stable HEK293 cell lines, 2 million cells were transfected with pJR255-based plasmids that express aptamers alone, shLuc, or shLuc-aptamer fusions. Transfected cells were selected with G418 (Gold Biotechnology, St. Louis, Mo., USA) for 10 to 14 days, followed by Fluorescent Activated Cell Sorting (FACS) to isolated mCherry positive cells. Typically, the brightest 10 to 30% of cells were collected. Second FACS was performed 7 to 10 days after the first sort to isolate stable cell populations. Cells isolated from second sort (typically 40 to 60% of cells) had a very stable mCherry signal and were used for lentivirus or HIV challenge experiments. Ghost cells were already G418 resistant, therefore, no selection step was performed. 0.5M cells were transfected with pJR255 based plasmids that express shLuc, aptamer alone or shLuc-aptamer fusions. Transfected cells were sorted 7 days after transfection. Compared to HEK293 cells, the percentage of mCherry positive cells was much lower because no drug selection was applied. Typically, the brightest 5 to 10% of cells were collected. A second sort was performed 14 days later. If a decrease in mCherry signal was observed, a third sort was performed.

To generate stable CCRF-CEM cell lines, 2 million cells were transfected with pJR288-based plasmids, that express shLuc, shLuc-S1R1, shLuc-S3R1 and shLuc-S3R3, by electroporation using the Nucleofactor kit according to the manufacturer's protocol (Lonza, Basel, Switzerland). G418 selection and FACS were performed similar to that of HEK293 cells.

For the lentivirus challenge, $5 \times 10^4$ HEK293 cells stably expressing the aptamer alone, the shRNA alone or the shRNA-aptamer fusions were transduced with HIV7-GFP lentivirus particles at an MOI of 0.3 in 500 µl cell culture medium. Cells were harvested 10 days post-transduction and analyzed by FACS. For an initial HIV challenge, $5 \times 10^4$ Ghost(3)X4/R5 cells stably expressing shRNA alone or shRNA-aptamer fusions were infected with HIV-1 Ba-L strain at an MOI of 0.02 in 500 µl medium. The HIV concentration of cells in culture was determined using a P24 assay with an Alliance HIV-1 P24 ELISA kit. (PerkinElmer, Waltham, Mass., USA). For a long term HIV challenge, $1 \times 10^5$ CCRF-CEM cells stably expressing shRNA or shRNA-aptamer fusions were infected with HIV-1 NL4-3 viruses at MOI of 0.02 in 500 µl medium. Three days after infection, cells were collected by centrifugation at 200×g for 3 min and resuspended in 1 ml fresh medium. Between week one to week six post-infection, 500 µl of cell culture was collected for analysis and replenished with 500 µl fresh medium. To maintain an unsaturated cell density, 50% of the cells were replaced with fresh medium in mid-week.

Results and Discussion

Figure 5B:
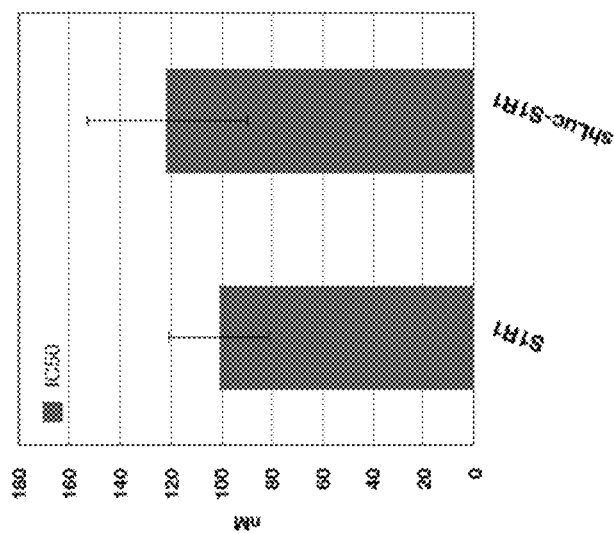
FIGS. 5A-5D illustrate that a shLuc-aptamer fusion causes weak but consistent inhibition of single cycle lentivirus infection according to some embodiments. (A) Mobility shift assay comparing aptamer S1R1 alone and shLuc-S1R1 fusion. (B) Quantification of affinity of S1R1 and shLuc-S1R1 to HIS-IN. Binding of S1R1 is the average of three independent assays while that of shLuc-S1R1 is the average of two independent assays. (C) FACS analysis of HEK293 cells expressing shLuc alone or shLuc-aptamer fusions infected by HIV7-GFP lentivirus at MOI of 0.3. (D) Quantification of FACS analysis. Percentage of double positive (Q2) over total GFP positive (Q2+Q3) was compared to shLuc only control (100%). Average and standard deviation of three independent assays is shown.
Figure 5A:
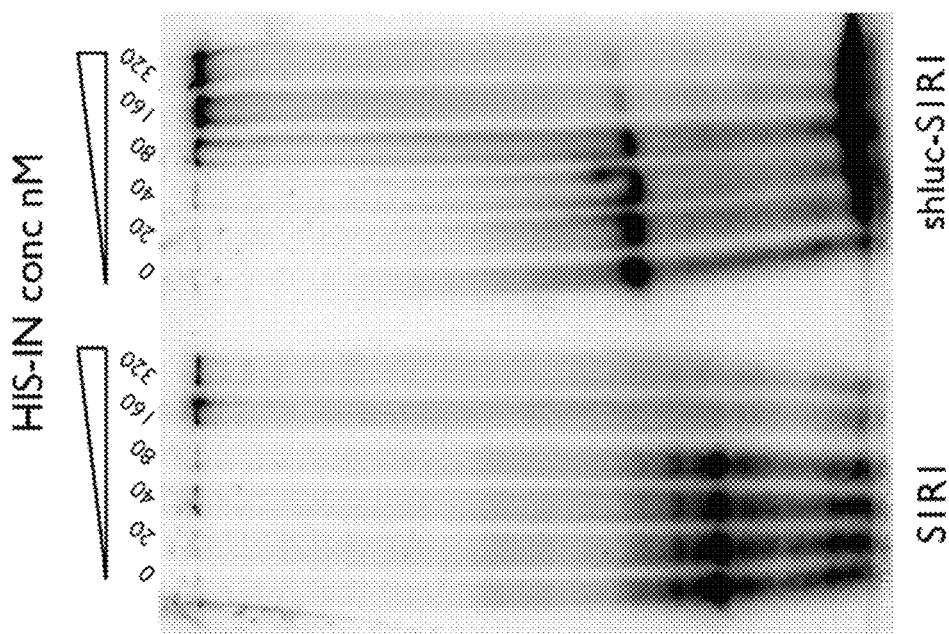
Figure 5C:
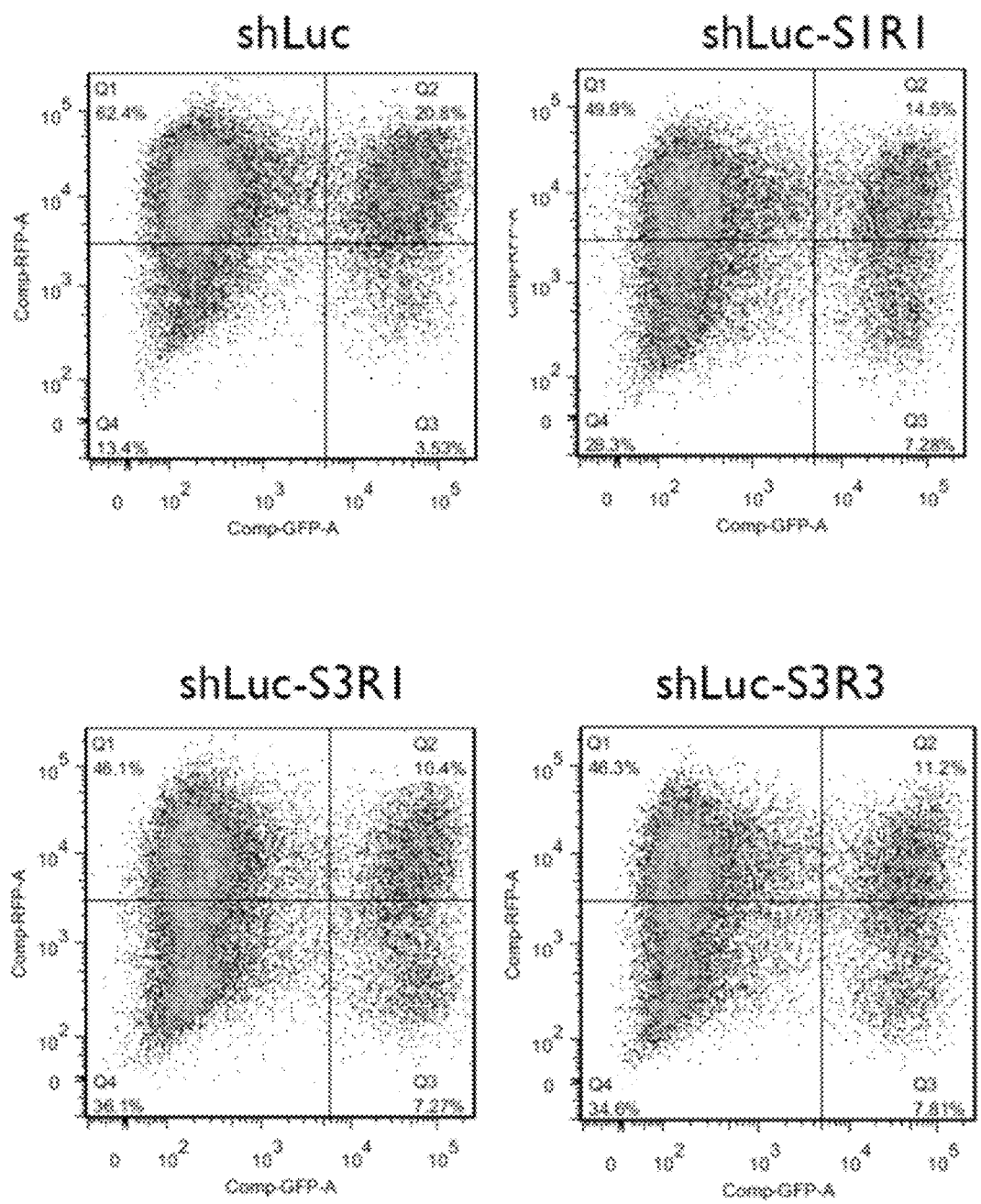
Figure 5D:
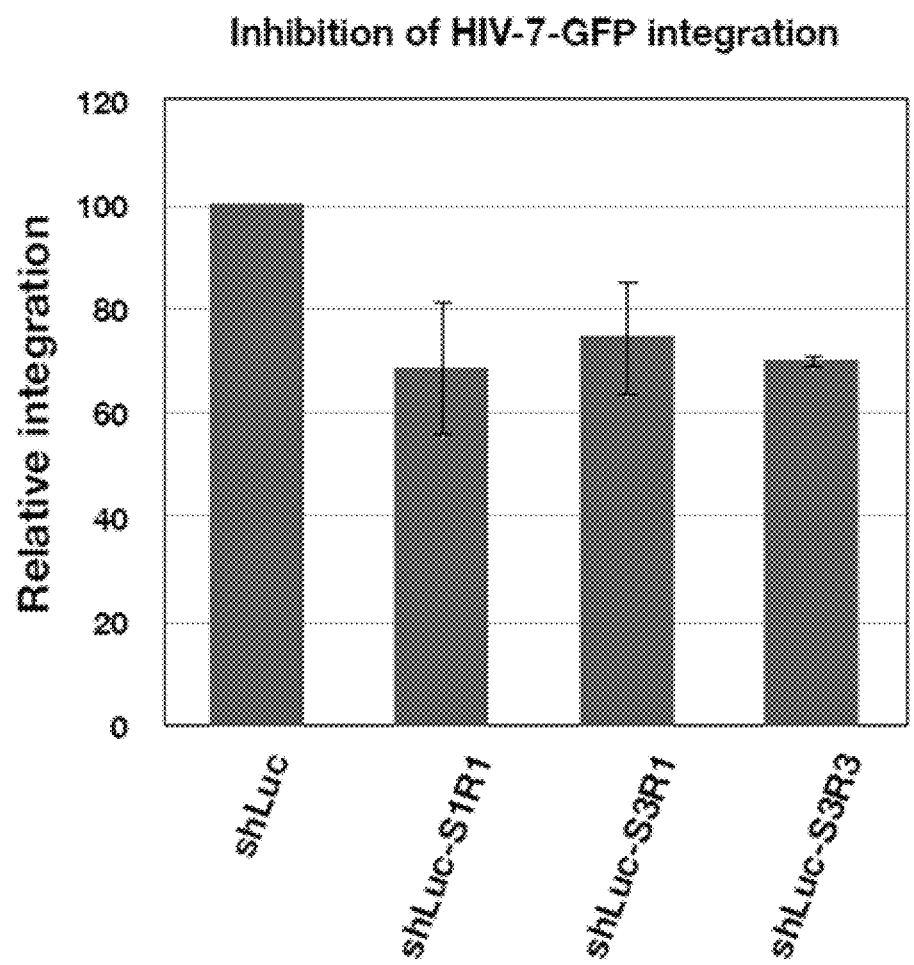

Despite an undetectable steady state level of released aptamer from the shRNA-aptamer fusion, the high level of shLuc-aptamer fusion may still bind to and inhibit integrase function. The stem of the shRNA affected the binding affinity of the aptamer using a gel mobility assay (FIG. 5A) to test this possibility. The binding affinity of S1R1 to HIS-IN was 101 nM+/−20 while that of shLuc-S1R1 was 121 nM+/−32 (P=0.8536) (FIG. 5B), suggesting that the addition of the shLuc stem did not appreciably alter the binding of the aptamer 51R1 to integrase. The shLuc-S1R1 and other fusions were tested using a functional assay to determine if there was any anti-HIV activity. Stable HEK293 cell lines expressing the shLuc alone, fusions of shLuc-S1R1, shLuc-S3R1 and shLuc-S3R3 were generated. When infected by lentivirus particle HIV-7-GFP, all three shLuc-aptamers fusions showed moderate but consistent inhibition of GFP expression, ranging from 20% to 30% (FIGS. 5C and 5D). This was an improvement compared to aptamer alone driven by the same U6 promoter (FIG. 12). These results indicated that when expressed from U6 promoter, the shRNA-aptamer fusions have higher anti-HIV activity than the aptamers alone. As such, aptamers incorporated into the terminal loop of an shRNA can be exported to the cytoplasm. The shRNA-aptamer fusions are cleaved by Dicer as shown by inhibit of the target luciferase. Released aptamer moiety was not detected in a Northern blot assay. This is consistent with rapid degradation of uncapped and unprotected RNA in the cytoplasm.

Figure 6B:
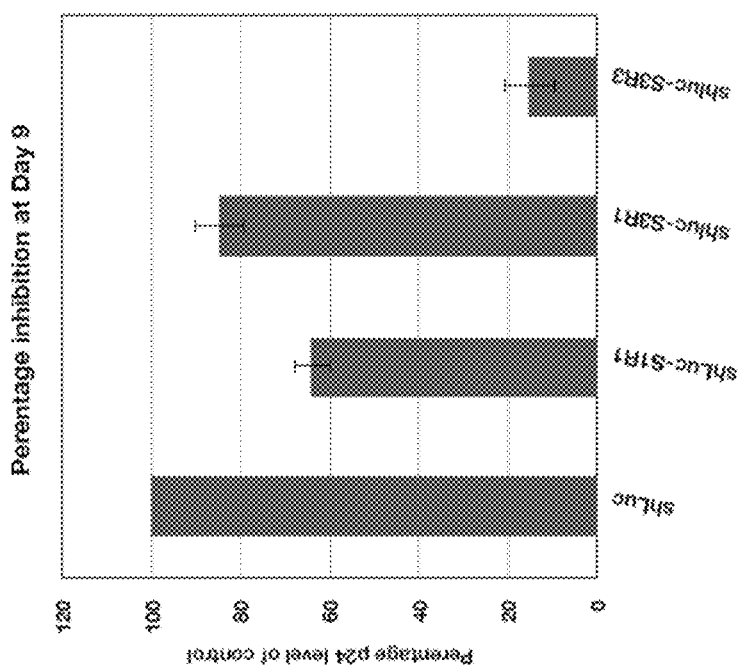
FIGS. 6A-6D illustrate that shLuc-aptamer fusions exhibit stronger inhibition of HIV replication in multiple cycle infection according to some embodiments. (A) shLuc-aptamer fusions inhibited Ba-L strain virus replication in Ghost3 cells. The change in virus concentration in Ghost3 cells infected with Ba-L virus was monitored by P24 assays. Data from a single representative assay using triplicate samples is shown as independent experiments exhibited large variation in the absolute value of P24 concentration. (B) Inhibition of HIV replication at Day9 post-infection. Percentage inhibition is represented by relative P24 concentration compared to an shLuc control. (C) An expressed shLuc RT aptamer fusion (shLuc-70.15) exhibited stronger inhibition compared to an expressed RT aptamer (70.15) alone. (D) Inhibition of HIV replication at day 9 post-infection. (A) and (C) illustrate a single representative experiment performed with triplicate samples. (B) and (D) illustrate percentage inhibition of relative p24 concentration to shLuc control. Averages and standard deviations of two (D) or three (B) independent biological assays are shown.
Figure 6A:
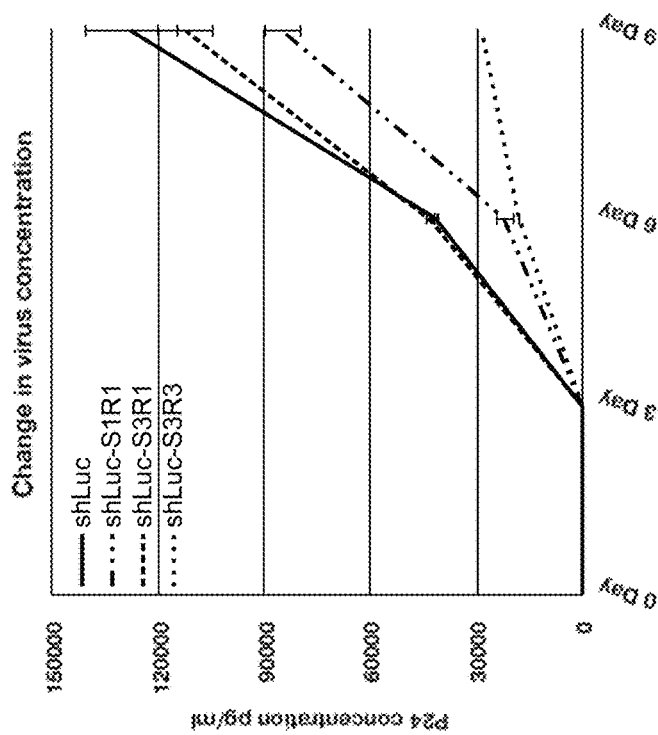

To test if the shRNA-fusions can exert inhibition during subsequent infection cycles using replication competent HIV, stable Ghost3+CXCR4+CCR5 cell lines expressing the shLuc alone and the shLuc-S1R1, shLuc-S3R1 and shLuc-53R3 fusions were generated (abbreviated as Ghost3 cells in following text) (Morner, et al., 1999). The Ghost3 lines were infected with the M-tropic HIV-1 Ba-L strain at a MOI of 0.02. The HIV concentration in cultures was monitored by P24 assay for 9 days. While shLuc-S1R1 and shLuc-S3R1 showed similar inhibition as single cycle (20 to 30% inhibition), shLuc-S3R3 consistently showed close to 85% inhibition towards replication competent HIV (FIGS. 6A and 6B). Thus, the shRNA-aptamer fusions may be more effective at inhibiting integrase when administered using multiple infection cycles. As such, shRNA-aptamer fusions exhibited inhibitory activity against HIV.

Figure 6D:
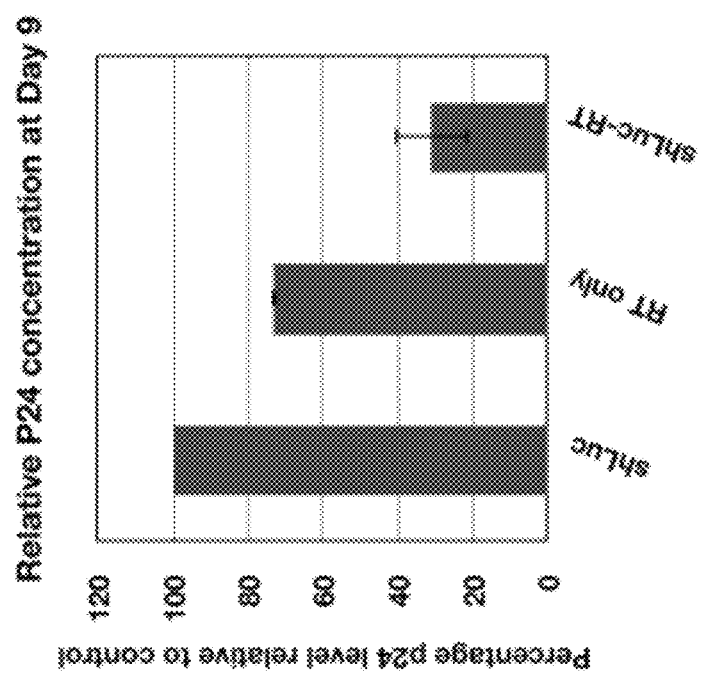
Figure 6C:
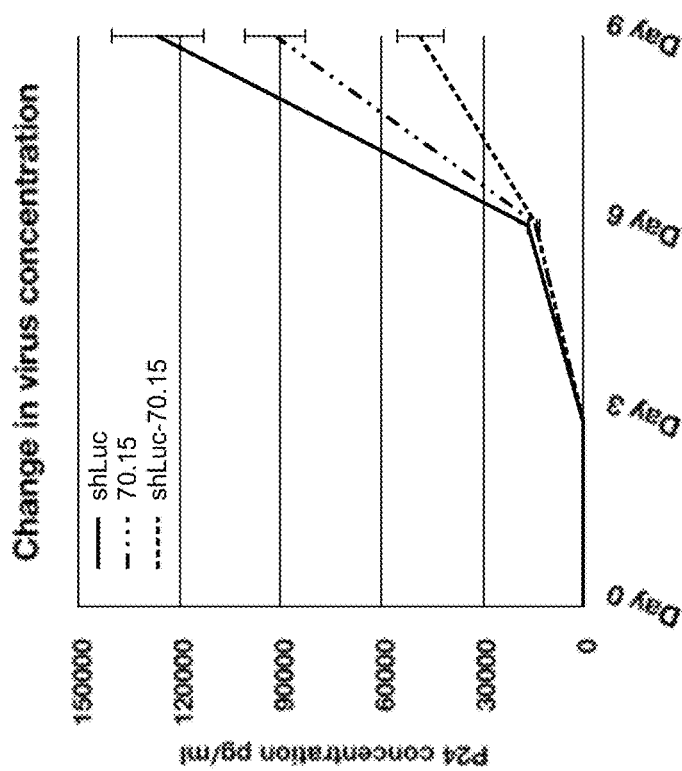

A fusion of shLuc and an RT aptamer (shLuc-70.15) was constructed (41). Stable Ghost3 cells expressing shLuc, 70.15 or shLuc-70.15 fusion were challenged with a Ba-L strain HIV. The p24 concentration in cultures were monitored for 9 days. Similar to the results using IN aptamers, the expressed shLuc-70.15 fusion exhibited stronger HIV inhibition compared to the RT aptamer alone (FIGS. 6C and 6D). This suggests that fusing an shRNA to an aptamer enhances the shRNA efficacy. In addition, this strategy may be useful for targeting cytoplasmic proteins, such as those functioning primarily in the cytoplasm.

Example 5: Aptamer S3R3 Synergizes with a shRNA Targeting HIV Tat-Rev and has Similar Efficacy as the Integrase Inhibitor Raltegravir Materials and Methods
Vectors:
The vectors used in this Example were designed and produced as described above with reference to Example 1.
HIV Challenge Methods and Associated In Vitro Cell Culture:
The challenge methods and associated cell culture were performed as described above with reference to Example 4.
Results and Discussion
Using the same HIV challenge methods as described in Example 4, the efficacy of the other candidate aptamers S3R4, S3R6 and S4R2 was tested. S3R3 remained the most effective in inhibiting proliferation of HIV-1 in Ghost3 cells, consistently showing 80 to 85% less p24 than the control (FIG. 12). Moreover, S3R3 showed a higher affinity (47 nM+/−3) toward HIS-IN than S1R1 (101 nM+/−20) (FIG. 14). Further studies focused on S3R3.

Figure 7B:
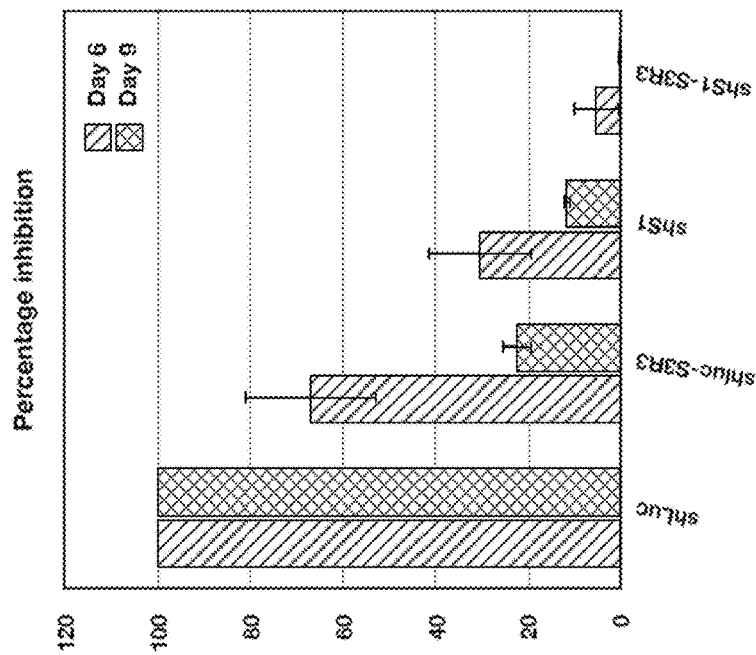
FIGS. 7A-7D illustrate that the shS1-S3R3 fusion has an efficacy comparable to the integrase inhibitor Raltegravir according to some embodiments. (A) and (B) shS1 and aptamer S3R3 (shS1-S3R3) showed synergistic inhibition against Ba-L HIV replication in Ghost3 cells. (A) The change in virus concentration of Ghost3 cells infected with Ba-L virus was monitored by P24 assays. (B) Percentage inhibition is represented by relative P24 concentration compared to the shLuc control is shown at Day 6 and Day 9 post-infection. (C) and (D). shS1-S3R3 showed an efficacy comparable to the integrase inhibitor Raltegravir. (C) Change in virus concentration in Ghost3 cells infected with Ba-L virus. (D) Inhibition of HIV replication at Day 9 post-infection. A single representative experiment with triplicate samples is shown in (A) and (C). The Y-axis is a semi-log scale, therefore, only positive error is shown. In (B) and (D), the average and standard deviation of two independent assays is shown.
Figure 7A:
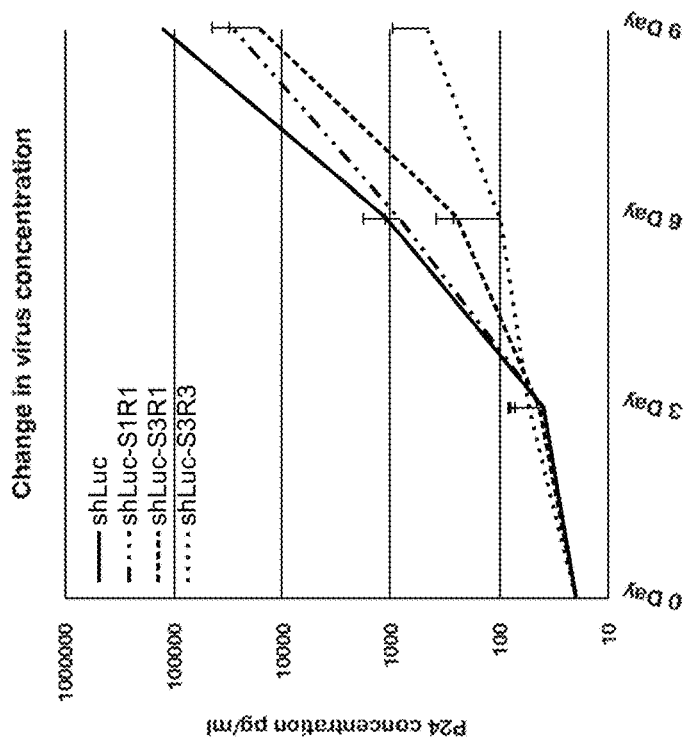

First, the anti-HIV activities of S3R3 were compared to that of an shRNA directed against the HIV Tat-Rev region (shS1). Stable Ghost3 cells expressing shS1 were generated and infected with the HIV Ba-L strain at a MOI of 0.02 for 9 days. P24 levels were compared to those from cells expressing the shLuc control and shLuc-S3R3. shS1 cells showed 2-fold stronger inhibition than shLuc-S3R3 at day 6. However, the difference was less at day 9 when shLuc-S3R3 showed 78% inhibition while shS1 showed 88% inhibition (FIGS. 7A and B). To test if a fusion RNA of shS1 and S3R3 exhibited synergy in inhibiting HIV propagation, a similar plasmid expressing a fusion of shS1 and S3R3 fusion RNA (shS1-S3R3) was constructed.

Stable Ghost3 cells lines were generated and then challenged with HIV-1 Ba-L strain. Although the individual RNA provided 80-90% inhibition of HIV replication, the combined shS1-53R3 fusion RNA resulted in a 100-fold stronger inhibition at Day 9 (FIGS. 7A and B).

Figure 7D:
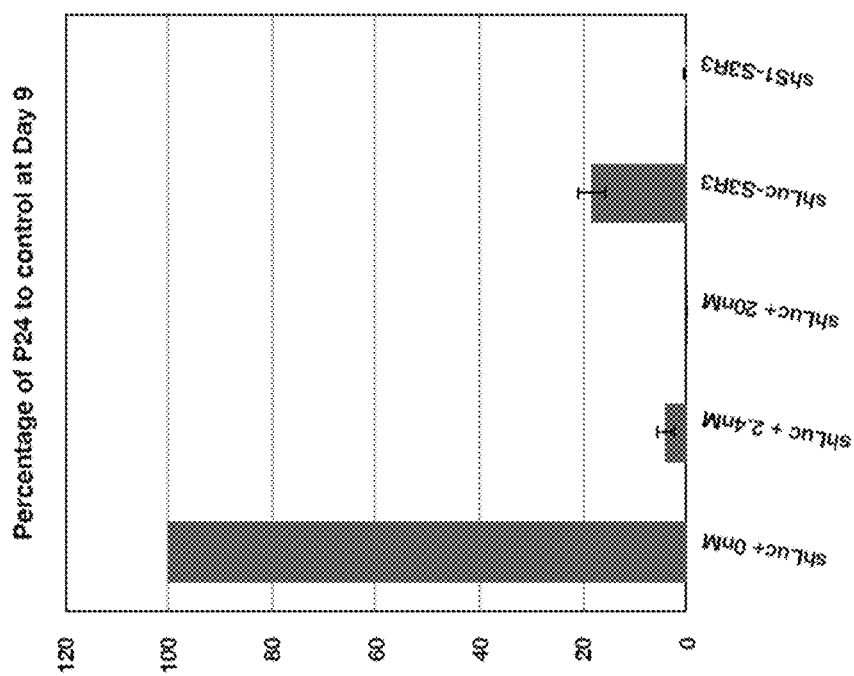
Figure 7C:
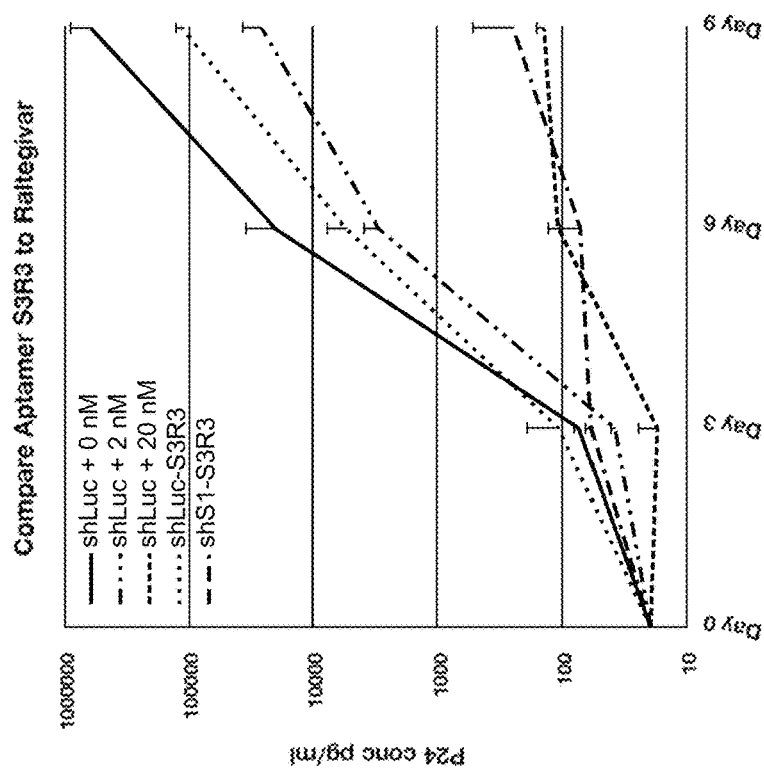

To further assess the potency of the aptamer S3R3, the efficacy of shLuc-S3R3 and the shS1-53R3 was compared to the FDA approved anti-Integrase drug Raltegravir. HIV Ba-L proliferation in Ghost3 cells expressing shLuc-S3R3 was compared to proliferation of control cells expressing shLuc in the present or absent of Raltegravir. Two concentrations of Raltegravir 2 nM and 20 nM, which corresponded to IC50 and IC95 in 10% FBS cell culture were tested. As previously observed, shLuc-S3R3 showed 80 to 85% inhibition at Day 9 compared to 96% inhibition for 2 nM and >99% inhibition for 20 nM Raltegravir (FIGS. 7, C and D). These results showed that S3R3 alone possessed anti-HIV activity was weaker than a low dose of Raltegravir. On the other hand, the combination of shS1 and S3R3 (shS1-53R3) showed very strong inhibition with a p24 level comparable to those treated with Raltegravir (FIGS. 7C and 7D). As such, combining anti-HIV shRNA and anti-Integrase aptamers could be a very effective strategy for gene therapy against HIV. Moreover, the integrase aptamer S3R3 had strong synergy with an shRNA targeting the tat-rev region and, together the shS1-53R3 fusion, strongly inhibited HIV replication in multi-cycle infection.

Example 6: Aptamer S3R3 is Effective in Long-Term Inhibition of HIV Replication

Figure 8B:
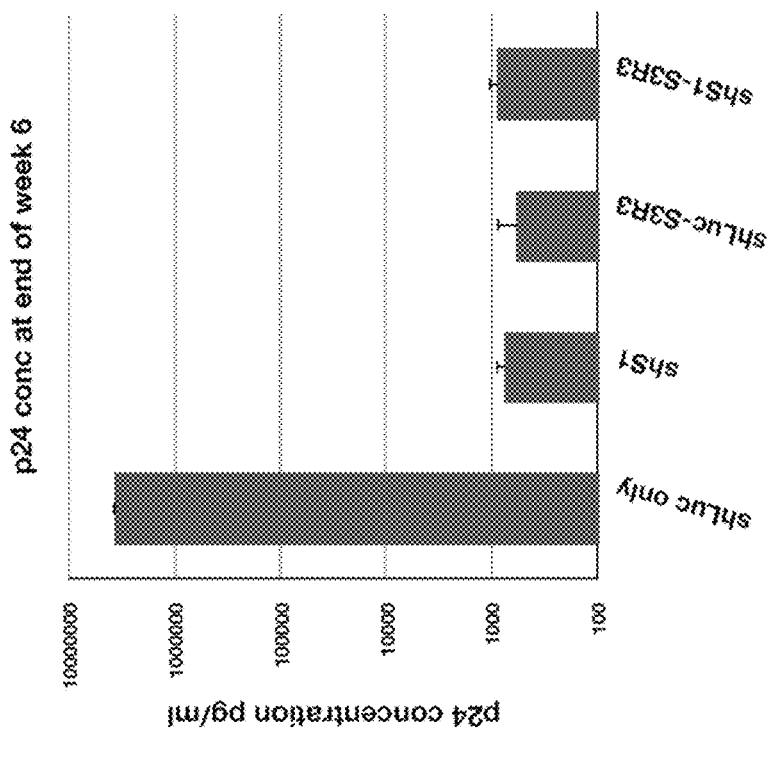
FIGS. 8A and 8B illustrate that shRNA-aptamer fusions showed long-term resistance to HIV replication in T cells according to some embodiments. (A) NL4-3 strain HIV virus growth in indicated CEM cell lines was monitored using P24 assays. (B) P24 concentration at the end of week 6 post infection. The Y-axis is a semi-log scale, therefore, only positive error is shown. The average and standard deviation of two independent assays is shown.
Figure 8A:
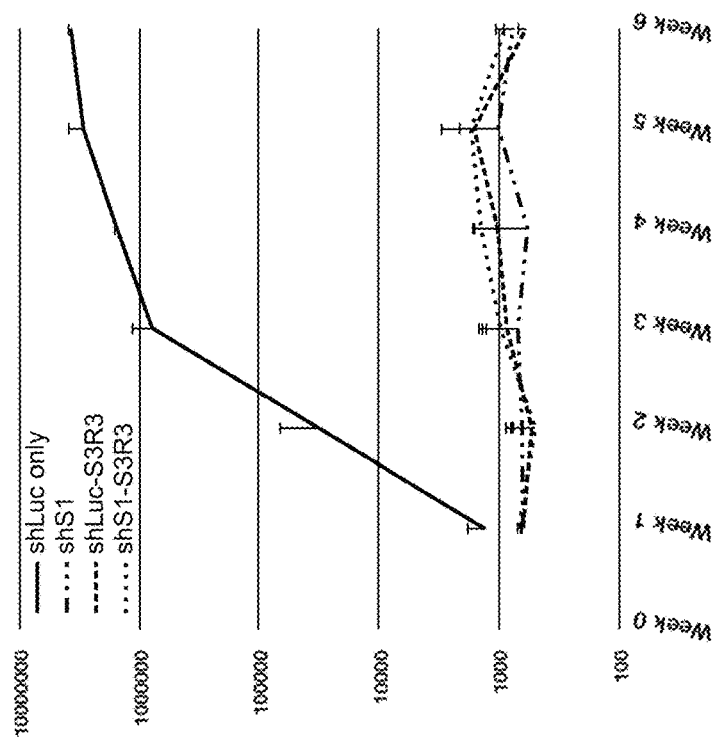
Figure 9B:
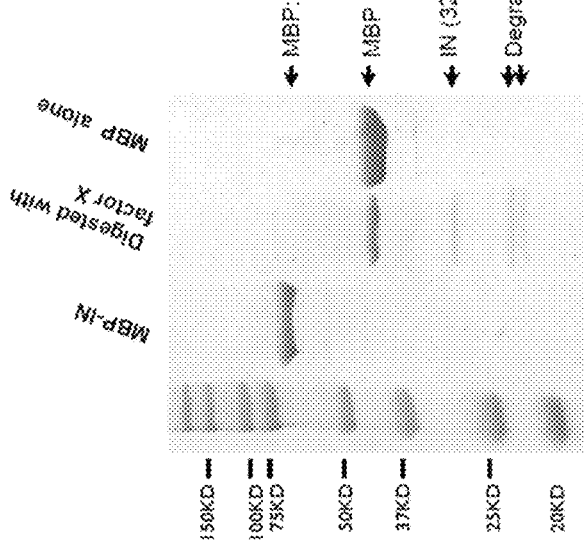
FIGS. 9A and 9B illustrates purification of HIS-IN and MBP-IN fusion proteins according to some embodiments. (A) Coomassie blue stained gel showing fractions of HIS-IN eluted from Ni-agarose column at 500 mM NaCl. When this purified protein was dialyzed against PBS, a substantial amount of protein was precipitated. (B) Coomassie blue stained gel showing purified MBP-IN fusion before and after digestion by factor X protease. More than half of the IN protein was degraded after the MBP moiety was separated. MBP alone served as positive control.
Figure 9A:
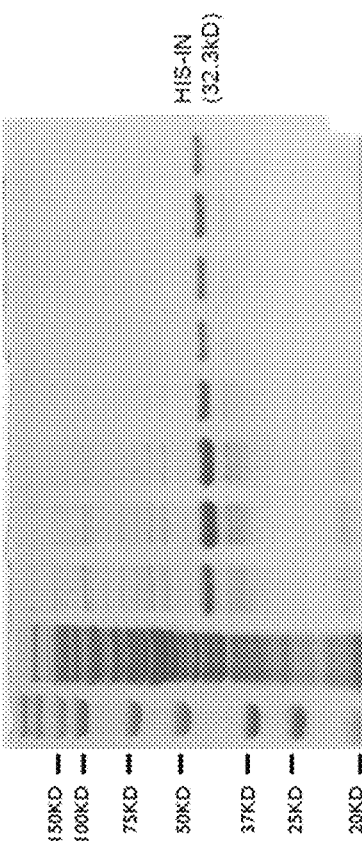

Materials and Methods
HIV Challenge Methods and Associated In Vitro Cell Culture:
The challenge methods and associated cell culture were performed as described above with reference to Example 4.
Results and Discussion
The long-term efficacy of shRNA-aptamer fusions in CD4 positive T cells was tested using CEM cells stably expressing shLuc, shLuc-S3R3, shS1 or shS1-S3R3. These stable CEM cells were generated as described above. 1×10$^5$ stable cells were infected with T-tropic HIV pNL4-3 at a MOI of 0.01. HIV concentrations were monitored for six weeks by p24 assay (FIG. 8). Aptamer alone (shLuc-S3R3) and shRNA alone (shS1) showed similar efficacy as the combination (shS1-S3R3). In all cases, the viral concentration was more than three orders of magnitude lower than that of control (shLuc) and did not increase over the observed 6 weeks. This inhibition was much stronger than that observed in Ghost3 cells (compare FIG. 8 to FIG. 7). Aptamer S3R3 was selected against integrase derived from pNL4-3 strain. This might explain a much stronger inhibition in this assay than in the short-term assays that challenged by the Ba-L strain. Alternatively, the fusions might exhibit higher potency in its natural host of T cells than in the engineered Ghost3 cell. In summary, anti-integrase aptamer expressed as an shRNA-aptamer fusion can confer long term resistance to HIV-1 replication in T cells. This strategy of expressing an aptamer into the terminal loop of an shRNA can be applicable for gene therapy against HIV and can potentially be adopted to treat other diseases.

Aptamers with high affinity to HIV-1 integrase were isolated using the multi-tag SELEX and identified using high throughput sequencing. This method is advantageous for selecting aptamers that target unstable or poorly soluble proteins, particularly under physiologically relevant conditions. In addition, stably expressed shRNA-aptamer fusions can confer long-term inhibition of HIV replication. Moreover, the efficacy of the anti-integrase aptamer could be enhanced by combining the aptamer with the shRNA against Tat-Rev (shS1). This combinatorial strategy allows both sequence based and structural based targeting using only one shRNA-aptamer fusion. In addition, the shRNA and aptamer combination allows flexibility in targeting either the same gene (protein and mRNA), two genes (one protein and one mRNA) or one protein plus one non-coding RNA. Moreover, by using multiplexed vectors (Chung, et al., 2014), multiple shRNA-aptamer fusions can be expressed from a single transcript. This allows inhibition of multiple targets at once and will be particular useful to combat the rapidly evolving HIV.

REFERENCES

The references, patents and published patent applications listed below, and all references cited in the specification above are hereby incorporated by reference in their entirety, as if fully set forth herein.
1. Leibman, R. S. and Riley, J. L. (2015) Engineering T Cells to Functionally Cure HIV-1 Infection. *Mol Ther,* 23, 1149-1159.
2. DiGiusto, D. L. (2015) Stem cell gene therapy for HIV: strategies to inhibit HIV entry and replication. *Curr HIV/AIDS Rep,* 12, 79-87.
3. Pernet, O., Yadav, S. S. and An, D. S. (2016) Stem cell-based therapies for HIV/AIDS. *Adv Drug Deliv Rev,* 103, 187-201.
4. Li, M. J., Kim, J., Li, S., Zaia, J., Yee, J. K., Anderson, J., Akkina, R. and Rossi, J. J. (2005) Long-term inhibition of HIV-1 infection in primary hematopoietic cells by lenti-HIV vector delivery of a triple combination of anti-HIV shRNA, anti-CCR5 ribozyme, and a nucleolar-localizing TAR decoy. *Mol Ther,* 12, 900-909.
5. Asparuhova, M. B., Barde, I., Trono, D., Schranz, K. and SchUmperli, D. (2008) Development and characterization of a triple combination gene therapy vector inhibiting HIV-1 multiplication. *J Gene Med,* 10, 1059-1070.
6. Anderson, J. S., Javien, J., Nolta, J. A. and Bauer, G. (2009) Preintegration HIV-1 Inhibition by a Combination LentiHIV Vector Containing a Chimeric TRIM5α Protein, a CCR5 shRNA, and a TAR Decoy. *Mol Ther,* 17, 2103-2114.
7. Chung, J., Scherer, L. J., Gu, A., Gardner, A. M., Torres-Coronado, M., Epps, E. W., Digiusto, D. L. and Rossi, J. J. (2014) Optimized lentiHIV vectors for HIV gene therapy: multiplexed expression of small RNAs and inclusion of MGMT(P140K) drug resistance gene. *Mol Ther,* 22, 952-963.
8. Tuerk, C. and Gold, L. (1990) Systematic evolution of ligands by exponential enrichment: RNA ligands to bacteriophage T4 DNA polymerase. *Science,* 249, 505-510.
9. Ellington, A. D. and Szostak, J. W. (1992) Selection in vitro of single-stranded DNA molecules that fold into specific ligand-binding structures. *Nature,* 355, 850-852.
10. Zhou, J., Swiderski, P., Li, H., Zhang, J., Neff, C. P., Akkina, R. and Rossi, J. J. (2009) Selection, characterization and application of new RNA HIV gp 120 aptamers for facile delivery of Dicer substrate siRNAs into HIV infected cells. *Nucleic Acids Res,* 37, 3094-3109.
11. Ramalingam, D., Duclair, S., Datta, S. A., Ellington, A., Rein, A. and Prasad, V. R. (2011) RNA aptamers directed to human immunodeficiency HIV type 1 Gag polyprotein bind to the matrix and nucleocapsid domains and inhibit HIV production. *J Virol,* 85, 305-314.
12. Ditzler, M. A., Bose, D., Shkriabai, N., Marchand, B., Sarafianos, S. G., Kvaratskhelia, M. and Burke, D. H. (2011) Broad-spectrum aptamer inhibitors of HIV reverse transcriptase closely mimic natural substrates. *Nucleic Acids Res,* 39, 8237-8247.
13. Whatley, A. S., Ditzler, M. A., Lange, M. J., Biondi, E., Sawyer, A. W., Chang, J. L., Franken, J. D. and Burke, D. H. (2013) Potent Inhibition of HIV-1 Reverse Transcriptase and Replication by Nonpseudoknot, "UCAA-motif" RNA Aptamers. Mol Ther Nucleic Acids, 2, e71.
14. Shum, K. T., Zhou, J. and Rossi, J. J. (2013) Aptamer-based therapeutics: new approaches to combat human HIV diseases. Pharmaceuticals (Basel), 6, 1507-1542.
15. Duclair, S., Gautam, A., Ellington, A. and Prasad, V. R. (2015) High-affinity RNA Aptamers Against the HIV-1 Protease Inhibit Both In Vitro Protease Activity and Late Events of HIV Replication. Mol Ther Nucleic Acids, 4, e228.
16. Kruspe, S., Mittelberger, F., Szameit, K. and Hahn, U. (2014) Aptamers as drug delivery vehicles. ChemMedChem, 9, 1998-2011.
17. Zhou, J. and Rossi, J. (2017) Aptamers as targeted therapeutics: current potential and challenges. Nat Rev Drug Discov, 16, 181-202.
18. Good, P. D., Krikos, A. J., Li, S. X., Bertrand, E., Lee, N. S., Giver, L., Ellington, A., Zaia, J. A., Rossi, J. J. and Engelke, D. R. (1997) Expression of small, therapeutic RNAs in human cell nuclei. Gene Ther, 4, 45-54.
19. Bertrand, E., Castanotto, D., Zhou, C., Carbonnelle, C., Lee, N. S., Good, P., Chatterjee, S., Grange, T., Pictet, R., et al. (1997) The expression cassette determines the functional activity of ribozymes in mammalian cells by controlling their intracellular localization. RNA, 3, 75-88.
20. Paul, C. P., Good, P. D., Li, S. X., Kleihauer, A., Rossi, J. J. and Engelke, D. R. (2003) Localized expression of small RNA inhibitors in human cells. Mol Ther, 7, 237-247.
21. Lee, N. S., Kim, D. H., Alluin, J., Robbins, M., Gu, S., Li, H., Kim, J., Salvaterra, P. M. and Rossi, J. J. (2008) Functional and intracellular localization properties of U6 promoter-expressed siRNAs, shRNAs, and chimeric VA1 shRNAs in mammalian cells. RNA, 14, 1823-1833.
22. Adachi, A., Gendelman, H. E., Koenig, S., Folks, T., Willey, R., Rabson, A. and Martin, M. A. (1986) Production of acquired immunodeficiency syndrome-associated retrovirus in human and nonhuman cells transfected with an infectious molecular clone. J Virol, 59, 284-291.
23. Jenkins, T. M., Engelman, A., Ghirlando, R. and Craigie, R. (1996) A soluble active mutant of HIV-1 integrase: involvement of both the core and carboxyl-terminal domains in multimerization. J Biol Chem, 271, 7712-7718.
24. Zhou, J., Satheesan, S., Li, H., Weinberg, M. S., Morris, K. V., Burnett, J. C. and Rossi, J. J. (2015) Cell-specific RNA aptamer against human CCR5 specifically targets HIV-1 susceptible cells and inhibits HIV-1 infectivity. Chem Biol, 22, 379-390.
25. Zuker, M. (2003) Mfold web server for nucleic acid folding and hybridization prediction. Nucleic Acids Res, 31, 3406-3415.
26. Castanotto, D., Lingeman, R., Riggs, A. D. and Rossi, J. J. (2009) CRM1 mediates nuclear-cytoplasmic shuttling of mature microRNAs. Proc Natl Acad Sci USA, 106, 21655-21659.
27. Mörner, A., Björndal, A., Albert, J., Kewalramani, V. N., Littman, D. R., Inoue, R., Thorstensson, R., Fenyö, E. M. and Bjtiding, E. (1999) Primary human immunodeficiency virus type 2 (HIV-2) isolates, like HIV-1 isolates, frequently use CCR5 but show promiscuity in coreceptor usage. J Virol, 73, 2343-2349.
28. Gartner, S., Markovits, P., Markovitz, D. M., Kaplan, M. H., Gallo, R. C. and Popovic, M. (1986) The role of mononuclear phagocytes in HTLV-III/LAV infection. Science, 233, 215-219.
29. Yam, P. Y., Li, S., Wu, J., Hu, J., Zaia, J. A. and Yee, J. K. (2002) Design of HIV vectors for efficient gene delivery into human hematopoietic cells. Mol Ther, 5, 479-484.
30. DiGiusto, D. L., Krishnan, A., Li, L., Li, H., Li, S., Rao, A., Mi, S., Yam, P., Stinson, S., et al. (2010) RNA-based gene therapy for HIV with lentiHIV vector-modified CD34(+) cells in patients undergoing transplantation for AIDS-related lymphoma. Sci Transl Med, 2, 36ra43.
31. Cherepanov, P., Maertens, G., Proost, P., Devreese, B., Van Beeumen, J., Engelborghs, Y., De Clercq, E. and Debyser, Z. (2003) HIV-1 integrase forms stable tetramers and associates with LEDGF/p75 protein in human cells. J Biol Chem, 278, 372-381.
32. Llano, M., Vanegas, M., Hutchins, N., Thompson, D., Delgado, S. and Poeschla,
33. E. M. (2006) Identification and characterization of the chromatin-binding domains of the HIV-1 integrase interactor LEDGF/p75. J Mol Biol, 360, 760-773.
34. Zheng, Y., Ao, Z., Wang, B., Jayappa, K. D. and Yao, X. (2011) Host Protein Ku70 Binds and Protects HIV-1 Integrase from Proteasomal Degradation and Is Required for HIV Replication. J Biol Chem, 286, 17722-17735.
35. Arhel, N. and Kirchhoff, F. (2010) Host proteins involved in HIV infection: new therapeutic targets. Biochim Biophys Acta, 1802, 313-321.
36. Cherepanov, P., Pluymers, W., Claeys, A., Proost, P., De Clercq, E. and Debyser, Z. (2000) High-level expression of active HIV-1 integrase from a synthetic gene in human cells. FASEB J, 14, 1389-1399.
37. Okada, C., Yamashita, E., Lee, S. J., Shibata, S., Katahira, J., Nakagawa, A., Yoneda, Y. and Tsukihara, T. (2009) A high-resolution structure of the pre-microRNA nuclear export machinery. Science, 326, 1275-1279.
38. Lee, S. J., Jiko, C., Yamashita, E. and Tsukihara, T. (2011) Selective nuclear export mechanism of small RNAs. Curr Opin Struct Biol, 21, 101-108.
39. Feng, Y., Zhang, X., Graves, P. and Zeng, Y. (2012) A comprehensive analysis of precursor microRNA cleavage by human Dicer. RNA, 18, 2083-2092.
40. Winter, J., Link, S., Witzigmann, D., Hildenbrand, C., Previti, C. and Diederichs, S. (2013) Loop-miRs: active microRNAs generated from single-stranded loop regions. Nucleic Acids Res, 41, 5503-5512.
41. Li, M. J. and Rossi, J. J. (2005) LentiHIV vector delivery of recombinant small interfering RNA expression cassettes. Methods Enzymol, 392, 218-226.
42. Lange, M. J., Sharma, T. K., Whatley, A. S., Landon, L. A., Tempesta, M. A., Johnson, M. C. and Burke, D. H. (2012) Robust suppression of HIV replication by intracellularly expressed reverse transcriptase aptamers is independent of ribozyme processing. Mol Ther, 20, 2304-2314.
43. Aagaard, L. A., Zhang, J., von Eije, K. J., Li, H., Saetrom, P., Amarzguioui, M. and Rossi, J. J. (2008) Engineering and optimization of the miR-106b cluster for ectopic expression of multiplexed anti-HIV RNAs. Gene Ther, 15, 1536-1549.
44. Summa, V., Petrocchi, A., Bonelli, F., Crescenzi, B., Donghi, M., Ferrara, M., Fiore, F., Gardelli, C., Gonzalez Paz, O., et al. (2008) Discovery of raltegravir, a potent, selective orally bioavailable HIV-integrase inhibitor for the treatment of HIV-AIDS infection. J Med Chem, 51, 5843-5855.
45. Temesgen, Z. and Siraj, D. S. (2008) Raltegravir: first in class HIV integrase inhibitor. Ther Clin Risk Manag, 4, 493-500.
46. Zheng, Y. and Yao, X. (2013) Posttranslational modifications of HIV-1 integrase by various cellular proteins during HIV replication. HIVes, 5, 1787-1801.
47. Mi, J., Zhang, X., Rabbani, Z. N., Liu, Y., Su, Z., Vujaskovic, Z., Kontos, C. D., Sullenger, B. A. and Clary, B. M. (2006) H1 RNA polymerase III promoter-driven expression of an RNA aptamer leads to high-level inhibition of intracellular protein activity. Nucleic Acids Res, 34, 3577-3584.
48. Choi, Y. S., Hur, J., Lee, H. K. and Jeong, S. (2009) The RNA aptamer disrupts protein-protein interaction between beta-catenin and nuclear factor-kappaB p50 and regulates the expression of C-reactive protein. FEBS Lett, 583, 1415-1421.
49. Salamanca, H. H., Antonyak, M. A., Cerione, R. A., Shi, H. and Lis, J. T. (2014) Inhibiting heat shock factor 1 in human cancer cells with a potent RNA aptamer. PLoS One, 9, e96330.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain embodiments of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Reference herein to "one embodiment," "an embodiment," or similar formulations means that a particular feature of a composition, a composition, a method, or a characteristic described in connection with the embodiment can be included in at least one embodiment of the present technology. Thus, the appearances of such phrases or formulations herein are not necessarily all referring to the same embodiment. Furthermore, various particular features, compositions, methods, or characteristics may be combined in any suitable manner in one or more embodiments.

From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. An RNA composition comprising:
   an RNA aptamer molecule comprising a nucleotide sequence of CGTATGGGTGAGCCCGTTAAGATT-GCGCGT (SEQ ID NO:1) that targets an enzymatic protein; and
   an shRNA molecule that transports the RNA aptamer to a desired location, wherein the RNA aptamer molecule and the shRNA molecule are fused together.

2. The RNA composition claim 1, wherein the RNA aptamer binds to and inhibits activity of the enzymatic protein.

3. The RNA composition of claim 2, wherein the enzymatic protein is integrase.

4. The RNA composition claim 3, wherein the integrase an HIV integrase.

5. The RNA composition of claim 2, wherein the enzymatic protein is a reverse transcriptase.

6. The RNA composition of claim 1, wherein the shRNA is an anti-HIV shRNA.

7. The RNA composition of claim 6, wherein the anti-HIV shRNA is an anti-HIV Tat-Rev shRNA.

8. The RNA composition of claim 1, wherein the RNA aptamer is part of a pharmaceutical composition which further comprises a pharmaceutical carrier.

9. A method of delivering a therapeutic agent to an HIV-infected cell comprising:
   contacting the HIV-infected cell with an RNA composition, wherein the RNA composition comprises an RNA aptamer component fused to a therapeutic agent component comprising an shRNA molecule; and wherein the RNA aptamer comprises a nucleotide sequence of CGTATGGGTGAGCCCGTTAAGATTGCGCGT (SEQ ID NO:1) and binds an enzymatic protein expressed by non-host DNA or non-host RNA, resulting in inhibition of activity of the enzymatic protein.

10. The method of claim 9, wherein the shRNA molecule is an anti-HIV shRNA.

11. The method of claim 9, wherein the enzymatic protein is an HIV integrase.

12. The method of claim 9, wherein binding the enzymatic protein with the RNA aptamer is accomplished by administering the RNA composition to a subject intravenously (i.v).

13. A pharmaceutical composition:
comprising an RNA composition, wherein the RNA composition comprises an RNA aptamer having a nucleotide sequence of CGTATGGGTGAGCCCGTTAAGATTGCGCGT (SEQ ID NO:1) that specifically binds an enzymatic protein fused to an shRNA molecule, and a pharmaceutically acceptable carrier.

* * * * *